(12) United States Patent
Schreiter et al.

(10) Patent No.: US 12,105,122 B2
(45) Date of Patent: Oct. 1, 2024

(54) VOLTAGE INDICATORS

(71) Applicant: HOWARD HUGHES MEDICAL INSTITUTE, Chevy Chase, MD (US)

(72) Inventors: Eric R. Schreiter, Ashburn, VA (US); Ahmed Abdelfattah, Ashburn, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 147 days.

(21) Appl. No.: 18/160,764

(22) Filed: Jan. 27, 2023

(65) Prior Publication Data

US 2023/0296649 A1  Sep. 21, 2023

Related U.S. Application Data

(63) Continuation of application No. 16/872,188, filed on May 11, 2020, now Pat. No. 11,598,792.

(60) Provisional application No. 62/845,643, filed on May 9, 2019.

(51) Int. Cl.
| | |
|---|---|
| *G01R 15/22* | (2006.01) |
| *C07K 14/195* | (2006.01) |
| *C07K 14/435* | (2006.01) |
| *G01N 21/64* | (2006.01) |
| *G01R 19/00* | (2006.01) |

(52) U.S. Cl.
CPC ......... *G01R 15/22* (2013.01); *G01R 19/0084* (2013.01); *C07K 14/195* (2013.01); *C07K 14/43504* (2013.01); *C07K 2319/60* (2013.01); *G01N 21/6486* (2013.01)

(58) Field of Classification Search
CPC ............... G01R 15/22; G01R 19/0084; C07K 14/43504; C07K 2319/60; C07K 2319/03; C07K 2319/33; C07K 2319/61; C07K 14/195; G01N 21/6486; C12Y 308/01005
USPC ........................................................ 324/96
See application file for complete search history.

(56) References Cited

U.S. PATENT DOCUMENTS

| | | | |
|---|---|---|---|
| 2016/0176931 A1* | 6/2016 | Kim ................ | C07K 14/00 435/367 |
| 2018/0118793 A1* | 5/2018 | Spudich ............ | A61P 27/02 |
| 2022/0056100 A1* | 2/2022 | Spudich ............ | C07K 14/705 |

OTHER PUBLICATIONS

Zheng, Qinsi, et al. "Rational Design of Fluorogenic and Spontaneously Blinking Labels for Super-Resolution Imaging," ACS Cent. Sci. 2019, 5, 1602-1613.
Grimm, Jonathan B., et al. "A general method to optimize and functionalize red-shifted rhodamine dyes," Nat Methods Aug. 2020; 17(8): 815-821.

* cited by examiner

*Primary Examiner* — Raul J Rios Russo
(74) *Attorney, Agent, or Firm* — Stites & Harbison, PLLC; Mandy Wilson Decker

(57) ABSTRACT

A voltage indicator includes a polypeptide sequence comprising a voltage-sensitive opsin domain and a capture protein domain arranged and disposed to capture a fluorescent dye ligand. When the fluorescent dye ligand is captured and the voltage indicator is bound to a cell membrane, an increase in voltage across the cell membrane causes an increase in fluorescent emission.

20 Claims, 58 Drawing Sheets
Specification includes a Sequence Listing.

FIG. 4

FIG. 5A
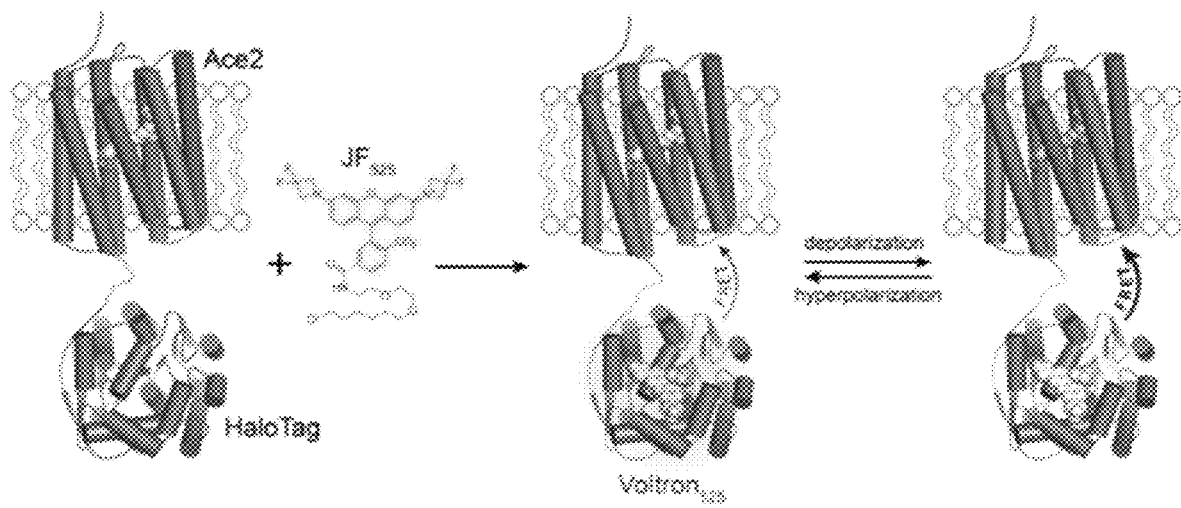
FIG. 5B
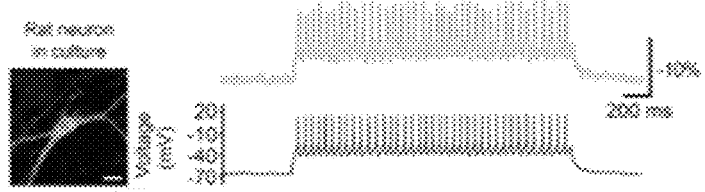
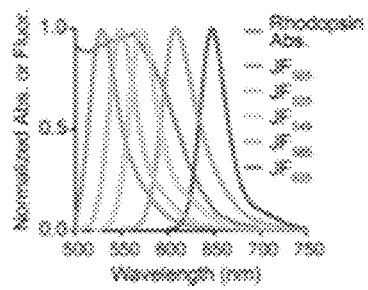
FIG. 5C　　　　　　　　FIG. 5D
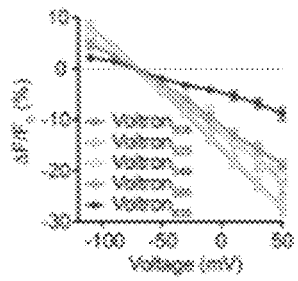
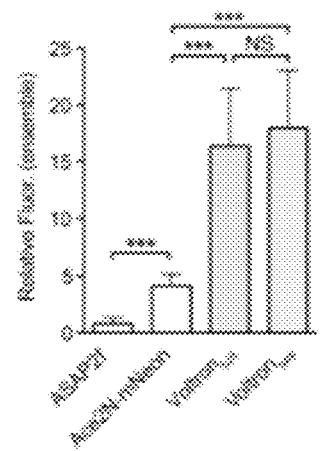
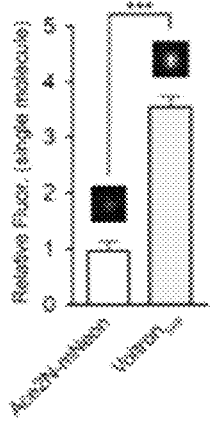
FIG. 5E　　　　　FIG. 5F　　　　　FIG. 5G

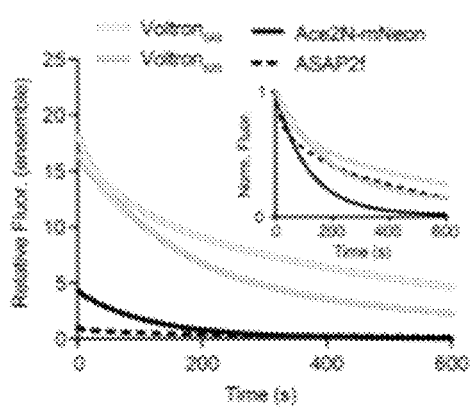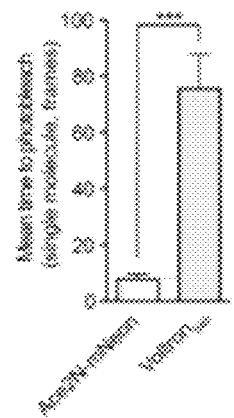
FIG. 5H  FIG. 5I
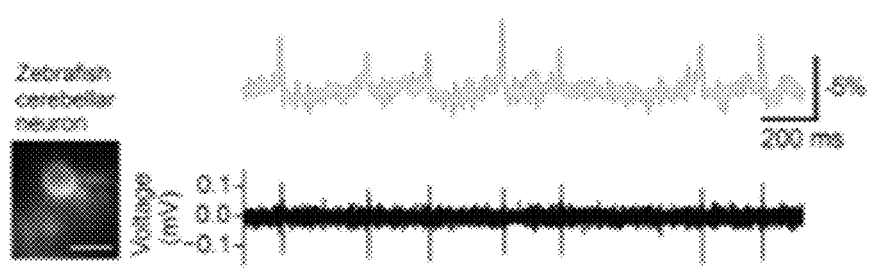
FIG. 5J
FIG. 5K

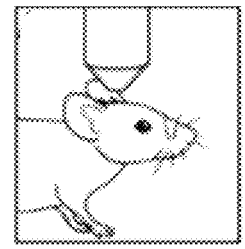 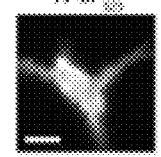
FIG. 6A  FIG. 6B
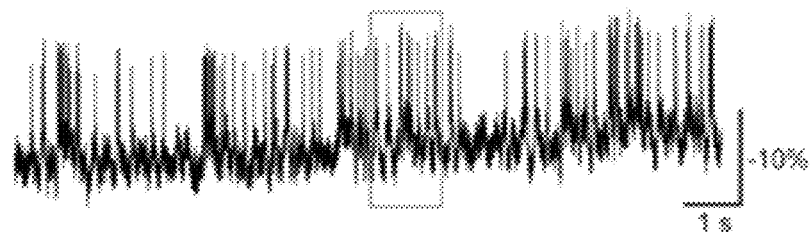
FIG. 6C
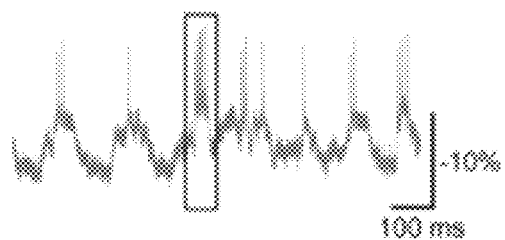 
FIG. 6D  FIG. 6E
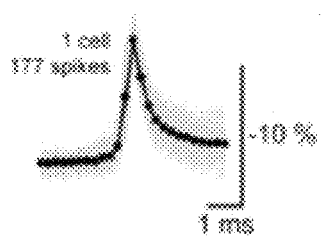 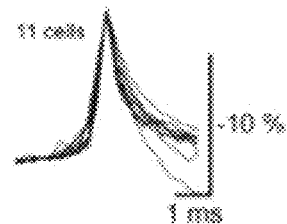
FIG. 6F  FIG. 6G
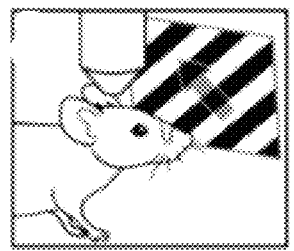
FIG. 6H

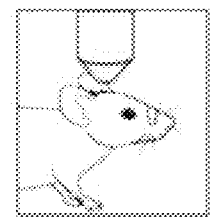
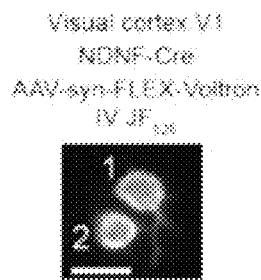
FIG. 7A    FIG. 7B
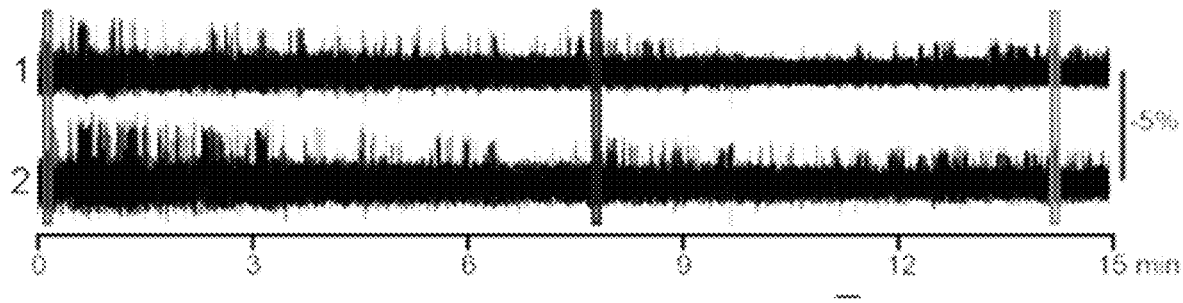
FIG. 7C
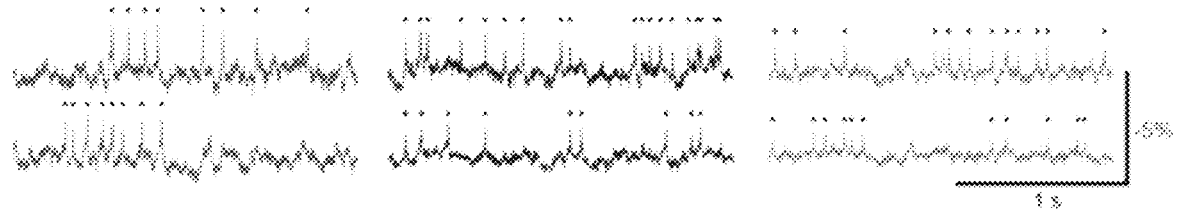
FIG. 7D
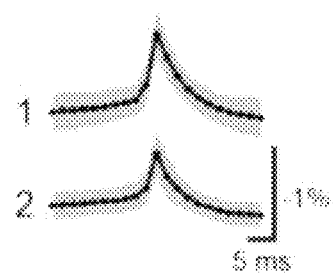
FIG. 7E

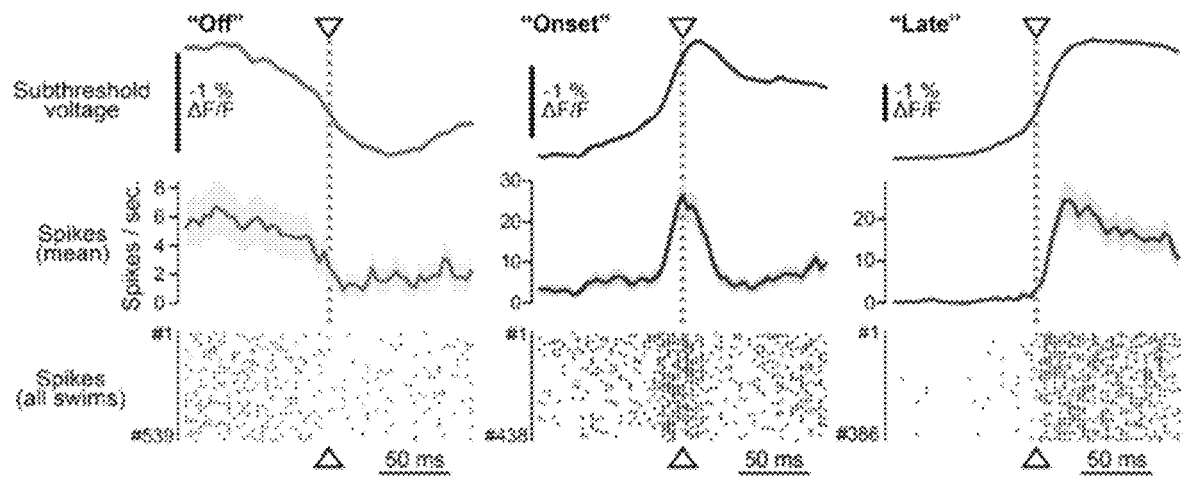
FIG. 8D
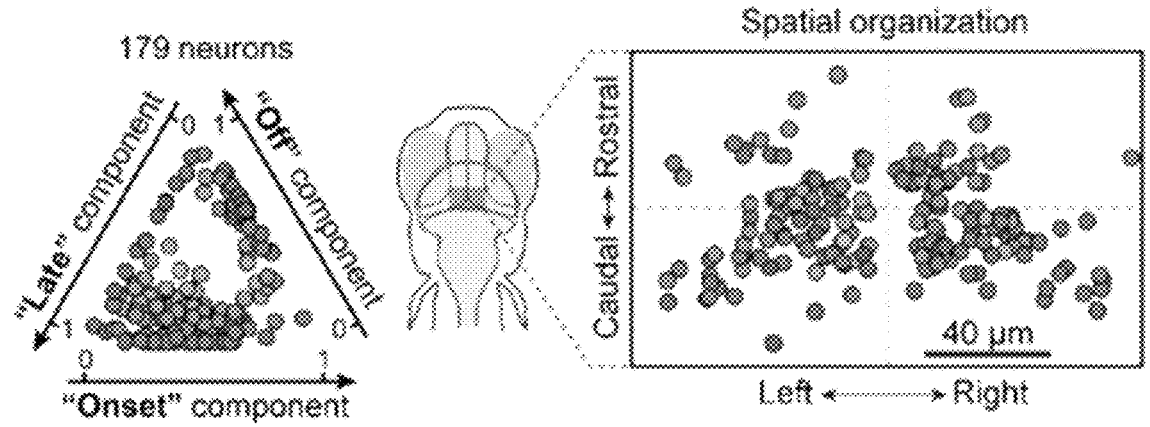
FIG. 8E
FIG. 8F
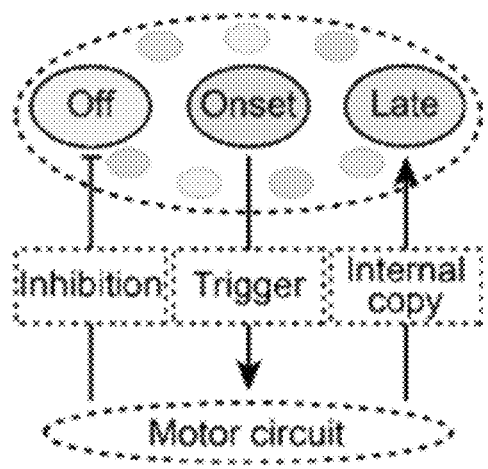
FIG. 8G

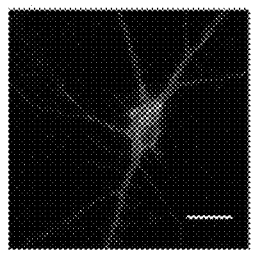 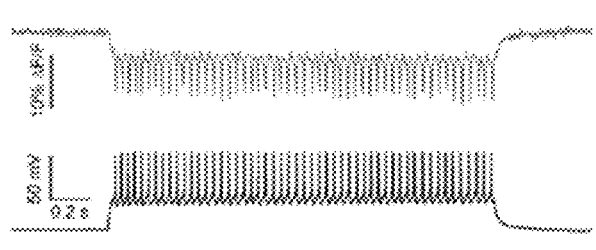 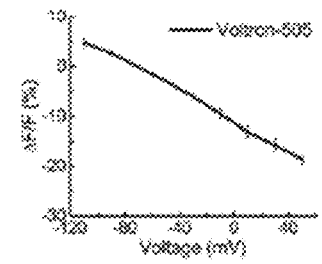
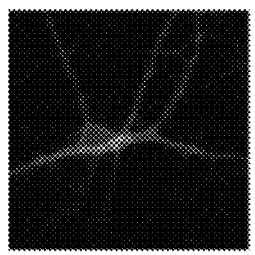 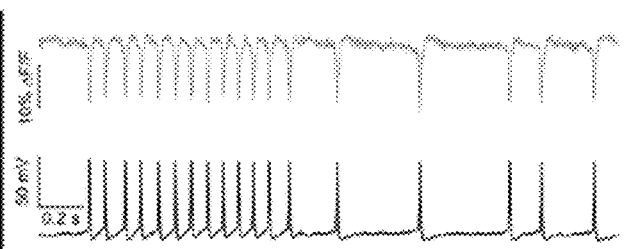 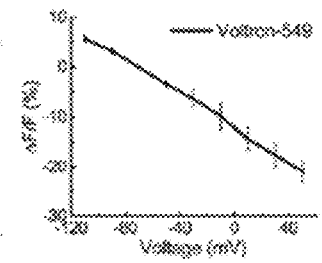
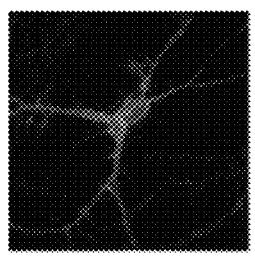 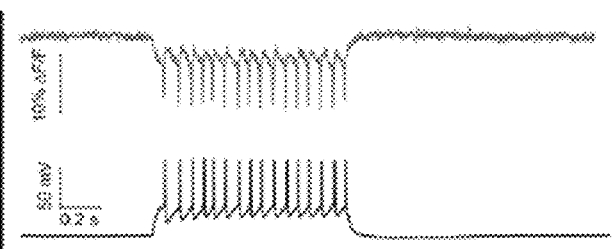 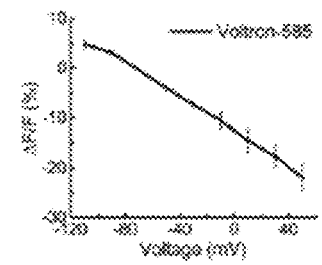
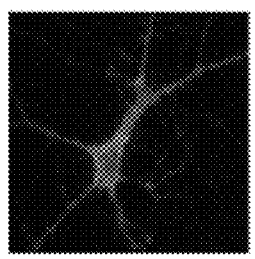 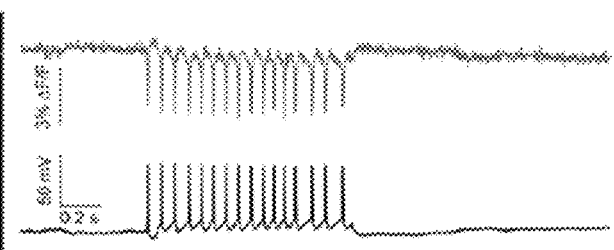 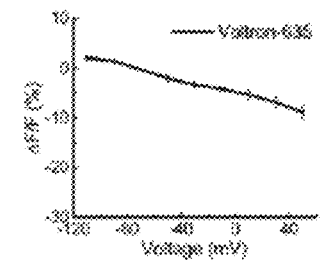
FIG. 13A      FIG. 13B      FIG. 13C

VOLTAGE INDICATORS

RELATED APPLICATIONS

This application is a continuation of U.S. patent application Ser. No. 16/872,188 filed May 11, 2020, which claims priority from U.S. Provisional Application Ser. No. 62/845,643 filed May 9, 2019, the entire disclosures of which are incorporated herein by this reference.

TECHNICAL FIELD

The presently-disclosed subject matter generally relates to voltage indicators and methods of use thereof. More specifically, the presently-disclosed subject matter relates to chemigenetic voltage indicators and methods of measuring voltage using chemigenetic voltage.

INTRODUCTION

Imaging changes in membrane potential using genetically encoded fluorescent voltage indicators (GEVIs) has great potential for monitoring neuronal activity with high spatial and temporal resolution.

Animal behavior is produced by patterns of neuronal activity that span a wide range of spatial and temporal scales. To understand how neural circuits mediate behavior thus requires high-speed recording from ensembles of neurons for long periods of time. Although the activity of large numbers of neurons can now be routinely recorded using genetically encoded calcium indicators (GECIs) (1), the slow kinetics of calcium signals complicate the measurement of action potentials, and sub-threshold voltage signals are missed entirely (1-3).

Voltage imaging using genetically encoded voltage indicators (GEVIs) can overcome these challenges, enabling imaging of fast spikes and subthreshold dynamics in genetically defined neurons (4, 5). The high imaging speed and excitation intensity required for voltage imaging, combined with the smaller volume of the cellular membrane, place increased demands on voltage indicators relative to GECIs.

Extant GEVIs rely on fluorescence from either microbial rhodopsins (6-8, 19) or fluorescent proteins (FPs) (9-13). These fluorophores lack the brightness and photostability to allow in vivo voltage imaging from large fields of view over timescales of many behavioral events, precluding the millisecond-timescale interrogation of neural circuits. Although the intrinsic fluorescence from rhodopsin domains is low, making them difficult to image, it has been possible to attach bright fluorophores, such as fluorescent proteins or rhodamine dyes, to rhodopsin domains to facilitate imaging (10, 11, 18).

These indicators function via electrochromic fluorescence resonance energy transfer (eFRET), and fluorescence from the bright fluorophore is decreased as the absorbance of the rhodopsin is increased. This results in a decrease in fluorescence with increasing membrane potential, and voltage signals, such as action potentials in neurons, take on a downward-going shape.

Upward-going fluorescence signals can be advantageous in microscopic imaging because, for example, background fluorescence from non-responsive regions is low and signals stand out above the background, increasing signal-to-noise, and, for another example, the fluorophore spends more time in the low-fluorescence state, which can decrease photobleaching.

Accordingly, there is a need in the art for improved voltage indicators that allow for the benefits associated with upward-going fluorescence signals.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

As disclosed herein, a unique electrochromic fluorescence resonance energy transfer (eFRET) genetically encoded voltage indicator (GEVIs) was engineered, which uses bright and photostable synthetic dyes instead of protein-based fluorophores, extending the combined duration of imaging and number of neurons imaged simultaneously by more than tenfold relative to existing GEVIs.

Recent development of improved rhodamine dyes such as the Janelia Fluor® (JF) dyes enable their use in complex biological experiments due to their high brightness and photostability (14), compatibility with self-labeling protein tags (15, 16), and the ability to traverse the blood-brain barrier for in vivo delivery (17).

Described herein is a 'chemigenetic' GEVI scaffold, referred to herein as "Voltron," which incorporates such synthetic fluorophore dyes. Voltron provides an increased photon yield that enables in vivo imaging of neuronal spiking and sub-threshold voltage signals in model organisms with order-of-magnitude improvement in the number of neurons imaged simultaneously over substantially longer durations.

Furthermore, through mutagenesis, an inversion of the direction of fluorescence change in rhodopsin eFRET GEVIs to an "upward-going" fluorescence signal was achieved, such that an increase in membrane potential lead to an increase in fluorescence.

The presently-disclosed subject matter includes a voltage indicator including a polypeptide sequence comprising a voltage-sensitive opsin domain including one, two, three, or four amino acid mutations relative to a wild type polypeptide sequence, and a capture protein domain arranged and disposed to capture a fluorescent dye ligand. When the fluorescent dye ligand is captured and the voltage indicator is bound to a cell membrane, an increase in voltage across the cell membrane causes an increase in fluorescent emission. In some embodiments, the response time between the increase in voltage and the increase in fluorescent emission is less than about a millisecond.

In some embodiments of the voltage indicator, the voltage-sensitive opsin domain is a microbial opsin domain. In some embodiments, the voltage-sensitive opsin domain is a microbial rhodopsin domain. In some embodiments, the microbial rhodopsin domain is selected from the group consisting of QuarsAr1, QuarsAr2, Ace2N, and combinations thereof.

In some embodiments, the voltage-sensitive opsin domain is Ace2N including an amino acid mutation at one or more of residue 81, 92, and 199.

In some embodiments, the voltage-sensitive opsin domain comprises the polypeptide of SEQ ID NO: 9, 15, 16, or 17, having one, two, three, or four amino acid mutations.

In some embodiments, the voltage-sensitive opsin domain comprises the amino acid sequence of SEQ ID NO: 9 having an amino acid mutation at one or more of residue 81, 92, and 199.

In some embodiments, the voltage indicator comprises an amino acid sequence selected from the group of amino acid sequences of SEQ ID NOS: 2, 4, 6, 8, 20, 22, 24, and 26.

In some embodiments, the voltage indicator comprises an amino acid sequence encoded by a nucleotide sequence selected from the group of nucleotide sequences of SEQ ID NOS: 1, 3, 5, 7, 19, 21, 23, and 25.

In some embodiments of the voltage indicator, the capture protein is a non-covalent capture protein. In some embodiments, the non-covalent capture protein is selected from the group consisting of TMP-tag®, biotin-avidin, and a combination thereof. In some embodiments, the capture protein domain is a self-labeling protein tag. In some embodiments, the capture protein domain is selected from a HaloTag® and a SNAP-Tag®. In some embodiments, the capture protein is a covalent capture protein selected from the group consisting of HaloTag®, SNAP-tag®, TMP-tag®, βLac-tag, CLIP-tag®, or a combination thereof. In some embodiments, the capture protein domain comprises an amino acid sequence selected from the amino acid sequence of SEQ ID NOS: 10 and 11. In some embodiments, 1, 2, 3, 4, 5, 6, 7, 8, 9, or 10 amino acids are removed from the junction between the opsin domain and the capture protein.

In some embodiments, the voltage indicator also includes a targeting sequence. In some embodiments, the targeting sequence is a soma targeting sequence. In some embodiments, the targeting sequence comprises the amino acid sequence of SEQ ID NO: 12. In some embodiments, the voltage-sensitive domain and the capture protein are provided as a fusion protein. In some embodiments, the capture protein is positioned at the c-terminal end of the voltage-sensitive domain.

In some embodiments of the voltage indicator, the fluorescent dye ligand is an azetidine-containing dye. For example, the fluorescent dye ligand can be a Janelia Fluor™ dye, such as, for example, Janelia Fluor™$_{505}$, Janelia Fluor™$_{525}$, Janelia Fluor™$_{549}$, Janelia Fluor™$_{585}$, Janelia Fluor™$_{646}$, and combinations thereof. In some embodiments, the fluorescent dye ligand is a fluorescent protein. For example, the fluorescent dye ligand can be a florescent protein such as sfGFP or mNeonGreen.

When the fluorescent dye ligand is captured by the capture protein domain, and when the voltage indicator is bound to a cell membrane, an increase in voltage across the cell membrane causes an increase in fluorescent emission from the fluorescent dye ligand. The cell membrane can be, for example, a cell membrane of a neuron. When there is an increase in voltage, in some embodiments, the increase in voltage includes a spike in voltage and a subthreshold voltage signal. In some embodiments, the response time between the increase in voltage and the increase in fluorescent emission is less than about a millisecond. In some embodiments the response time between the increase in voltage and the increase in fluorescent emission is less than about a millisecond.

The presently-disclosed subject matter includes a method of measuring voltage, which involves administering or contacting the voltage indicator as described herein and determining changes in fluorescence of the fluorescent dye ligand. In this regard, the indicator can be contacted with a cell, such as, for example, a neuron. When the fluorescent dye ligand is captured by the capture protein domain, and when the voltage indicator is bound to a cell membrane, an increase in voltage across the cell membrane causes an increase in fluorescent emission from the fluorescent dye ligand. In some embodiments, the increase in voltage is a spike in voltage or a subthreshold voltage signal. In some embodiments, the response time between the increase in voltage and the increase in fluorescent emission is less than about a millisecond. In some embodiments, the response time between the increase in voltage and the increase in fluorescent emission is less than about a millisecond. In some embodiments of the method, the changes in fluorescence are observed with a microscope.

In some embodiments, the voltage indicator further comprises a linker between the voltage-sensitive domain and the capture protein domain, and the method further involves modifying a length of the linker. In some embodiments, modifying the length of the linker includes removing at least one amino acid residue. In some embodiments, between 1 and 22 amino acid residues are removed. In some embodiments, modifying the length of the linker modifies the size of a fluorescence response. In some embodiments, the method also includes determining changes in voltage based upon changes in fluorescence. In some embodiments, an increase in membrane potential leads to an increase in fluorescence.

BRIEF DESCRIPTION OF THE SEQUENCE LISTING

SEQ ID NO: 1 is the nucleotide sequence encoding an exemplary voltage indicator according to the presently-disclosed subject matter.

SEQ ID NO: 2 is the polypeptide sequence an exemplary voltage indicator according to the presently-disclosed subject matter.

SEQ ID NO: 3 is the nucleotide sequence encoding an exemplary voltage indicator according to the presently-disclosed subject matter.

SEQ ID NO: 4 is the polypeptide sequence of an exemplary voltage indicator according to the presently-disclosed subject matter.

SEQ ID NO: 5 is the nucleotide sequence encoding an exemplary voltage indicator according to the presently-disclosed subject matter.

SEQ ID NO: 6 is the polypeptide sequence of an exemplary voltage indicator according to the presently-disclosed subject matter.

SEQ ID NO: 7 is the nucleotide sequence encoding an exemplary voltage indicator according to the presently-disclosed subject matter.

SEQ ID NO: 8 is the polypeptide sequence of an exemplary voltage indicator according to the presently-disclosed subject matter.

SEQ ID NO: 9 is the polypeptide sequence of an exemplary voltage-sensitive domain according to the presently-disclosed subject matter.

SEQ ID NO: 10 is the polypeptide sequence of an exemplary capture protein domain according to the presently-disclosed subject matter.

SEQ ID NO: 11 is the polypeptide sequence of an exemplary capture protein domain according to the presently-disclosed subject matter.

SEQ ID NO: 12 is the polypeptide sequence of an exemplary targeting sequence according to the presently-disclosed subject matter.

SEQ ID NO: 13 is the polypeptide sequence of an exemplary targeting sequence according to the presently-disclosed subject matter.

SEQ ID NO: 14 is the polypeptide sequence of an exemplary targeting sequence according to the presently-disclosed subject matter.

SEQ ID NO: 15 is the polypeptide sequence of an exemplary voltage-sensitive domain according to the presently-disclosed subject matter.

SEQ ID NO: 16 is the polypeptide sequence of an exemplary voltage-sensitive domain according to the presently-disclosed subject matter.

SEQ ID NO: 17 is the polypeptide sequence of an exemplary voltage-sensitive domain according to the presently-disclosed subject matter.

SEQ ID NO: 18 is the polypeptide sequence of an exemplary capture protein domain according to the presently-disclosed subject matter.

SEQ ID NO: 19 is the nucleotide sequence as set forth in FIG. 4.

SEQ ID NO: 20 is the polypeptide sequence as set forth in FIG. 4.

SEQ ID NO: 21 is the nucleotide sequence as set forth in FIG. 10.

SEQ ID NO: 22 is the polypeptide sequence as set forth in FIG. 10.

SEQ ID NO: 23 is the nucleotide sequence as set forth in FIG. 11.

SEQ ID NO: 24 is the polypeptide sequence as set forth in FIG. 11.

SEQ ID NO: 25 is the first nucleotide sequence as set forth in FIG. 12.

SEQ ID NO: 26 is the first polypeptide sequence as set forth in FIG. 12.

SEQ ID NO: 27 is the second nucleotide sequence as set forth in FIG. 12.

SEQ ID NO: 28 is the second polypeptide sequence as set forth in FIG. 12.

SEQ ID NO: 29 is the third nucleotide sequence as set forth in FIG. 12.

SEQ ID NO: 30 is the third polypeptide sequence as set forth in FIG. 12.

SEQ ID NO: 31 is the fourth nucleotide sequence as set forth in FIG. 12.

SEQ ID NO: 32 is the fourth polypeptide sequence as set forth in FIG. 12.

SEQ ID NO: 33 is the fifth nucleotide sequence as set forth in FIG. 12.

SEQ ID NO: 34 is the fifth polypeptide sequence as set forth in FIG. 12.

SEQ ID NO: 35 is the sixth nucleotide sequence as set forth in FIG. 12.

SEQ ID NO: 36 is the sixth polypeptide sequence as set forth in FIG. 12.

SEQ ID NO: 37 is the seventh nucleotide sequence as set forth in FIG. 12.

SEQ ID NO: 38 is the seventh polypeptide sequence as set forth in FIG. 12.

SEQ ID NO: 39 is the eighth nucleotide sequence as set forth in FIG. 12.

SEQ ID NO: 40 is the eighth polypeptide sequence as set forth in FIG. 12

REFERENCE TO AN ELECTRONIC SEQUENCE LISTING

The contents of the electronic sequence listing (Schreiter-19013U2.xml; Size: 85,763 bytes; and Date of Creation: Apr. 27, 2023) is herein incorporated by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 4 includes a nucleotide sequence (SEQ ID NO: 19) and amino acid sequence (SEQ ID NO: 20) of "Voltron," an exemplary rhodopsin electrochromic fluorescence resonance energy transfer (eFRET) genetically encoded voltage indicators (GEVIs), with sequence features annotated. To localize the indicator to the neuron soma, a targeting sequence from Kv2.1 was added to the C-terminus of the sequence.

FIGS. 5A-5K are related to development of the chemigenetic voltage indicator Voltron. FIG. 5A: Schematic of Voltron sequence: A rhodopsin (Ace2) is fused to a self-labeling tag domain (HaloTag) with additional sequences added to improve or localize membrane targeting: endoplasmic reticulum export sequence (ER), Golgi export trafficking sequence (TS), and somatic targeting sequence (ST). FIG. 5B: Model of Voltron mechanism. The HaloTag domain of the transmembrane Voltron protein (grey cylinders) covalently binds a small molecule fluorophore such as JF525 (green glow) with an appended HaloTag ligand. Membrane depolarization reversibly decreases JF525 fluorescence via increased FRET to the rhodopsin domain. FIG. 5C: Left panel: cultured rat hippocampal neuron expressing Voltron and labeled with $_{JF525}$. Scale bar: 20 µm. Right panel: single-trial recording of action potentials and sub-threshold voltage signals from current injections in primary neuron culture using imaging (top, fluorescence) or electrophysiology (bottom, membrane potential). FIG. 5D: Fluorescence emission spectra of different JF dyes overlaid with the absorbance spectrum of Ace2N. FIG. 5E: Fluorescence change as a function of membrane voltage with different JF dye-Voltron conjugates. FIG. 5F: Relative fluorescence of ASAP2f, Ace2N-mNeon, Voltron$_{525}$ and Voltron$_{549}$ in cultured neurons (n=70, 68, 48 and 62 measurements from five independent transfections for each construct). Illumination intensity ~10 mW/mm$^2$ at imaging plane. *P<0.001, one-way analysis of variance (ANOVA) followed by Bonferroni's test on each pair. Fluorescence was normalized to ASAP2f mean intensity. FIG. 5G: Relative single molecule brightness of Ace2N-mNeon and Voltron$_{549}$. *P<0.001, two-tailed Student's t-test. FIG. 5H: Bleaching curves for ASAP2f, Ace2N-mNeon, Voltron$_{525}$, and Voltron$_{549}$ in primary neuron culture. Illumination intensity ~23 mW/mm$^2$ at imaging plane. Bleaching curves were normalized to mean cellular fluorescence from FIG. 5F or normalized to the zero-time value (inset). FIG. 5I: Mean time to bleach of Ace2N-mNeon and Voltron$_{549}$ during single-molecule imaging, 100 ms frames. ***P<0.001, two-tailed Student's t-test. FIGS. 5J and 5K: Simultaneous in vivo Voltron imaging and electrophysiology in larval zebrafish (extracellular) and adult *Drosophila* (whole cell), respectively.

FIGS. 6A-6L are related to membrane voltage dynamics in hippocampal parvalbumin (PV) neurons (FIGS. 6A-6G) and visual cortex pyramidal neurons (FIGS. 6A-6L) of mice using Voltron. (FIGS. 6C-6E) Voltron525 raw $\Delta F/F_0$ traces showing spontaneous spikes of a PV neuron (FIG. 6B) located at a depth of 60 µm in hippocampal CA1 region imaged at 3858 frames per second. Boxes indicate intervals shown at expanded time scales. Scalebar: 20 µm. (FIG. 6F) Overlay of 177 spikes detected during a 15 s period (gray) and their average (black). (FIG. 6G) Spike shape of 11 PV neurons. (FIG. 6H) Schematic of imaging of mouse primary visual cortex during display of drifting grating visual stimuli. (FIG. 6I) Example trace showing Voltron fluorescence during one trial of a sequence of visual stimuli. Arrows below represent the direction of movement of the drifting grating. (FIGS. 6J-6L) Top left, images of a pyramidal cell at a depth of 148 µm, imaged three times over a period of four weeks on the indicated weeks after virus injection. Scalebar: 10 µm. Top right, average of all spikes in session (black) and standard deviation (grey). Middle, raw $\Delta F/F_0$ trace for five repetitions in each session, showing two orthogonal orientations (indicated with arrows below) from the neuron pictured on the top left. Bottom, orientation tuning to full-frame drifting gratings of the neuron pictured on the top left, displayed from number of spikes during trials (blue), number of spikes during preceding inter-trial intervals (grey), and subthreshold $\Delta F/F_0$ (right y-axis) after low-pass filtering traces using a 10-point median filter. For each orientation, response is calculated by averaging the low-pass filtered trace between 100-400 ms after trial onset, and baseline is calculated by averaging the low pass filtered trace from 80 ms preceding trial onset to 20 ms after trial onset. Displayed as response minus baseline. Error bars represent standard error of the mean (s.e.m.) (20-22 repetitions per session).

FIGS. 7A-7G include long duration and large FOV imaging of voltage activity in GABA-ergic neurons in mouse neocortex. (FIG. 7A) Schematic of the imaging setup. (FIG. 7B) Image of two neurons expressing ST-Voltron$_{525}$ in layer 1 of visual cortex of an NDNF-Cre mouse. Scalebar: 10 µm. (FIG. 7C) $\Delta F/F_0$ traces from neurons in FIG. 7B, recorded over 15 minutes. (FIG. 7D) Color-coded zooms of indicated regions of the traces in FIG. 7C with detected action potentials indicated by black dots above the fluorescence traces. (FIG. 7E) Average of all spikes in session (black) and standard deviation (grey). (FIG. 7F) Left panel: Fluorescence image of a cranial window over primary visual cortex (V1) in an NDNF-Cre mouse showing Cre-dependent expression of ST-Voltron$_{525}$ (bright spots). Scalebar: 1 mm. Right panel: zoomed image of FIG. 7F in the area indicated by the white rectangle, with neurons labels corresponding to fluorescence traces in FIG. 7G. Scalebar: 100 µm. (FIG. 7G) Left panel: $\Delta F/F_0$ traces during 3 min. recording from neurons pictured in FIG. 7F, in decreasing order of signal-to-noise ratio. Right panel: zooms of $\Delta F/F_0$ traces from color-coded regions of FIG. 7G with detected action potentials represented as black dots above, illustrating representative traces with high (top), medium (middle), and low (bottom) SNR. Traces have been background-subtracted, which removes shared subthreshold membrane potential fluctuations (Compare vs. FIG. 27 without subtraction).

FIGS. 8A-8G illustrate millisecond-timescale neural dynamics during swimming behavior in zebrafish. (FIG. 8A) Schematic illustration of the setup. An immobilized zebrafish is placed under the light-sheet microscope and the motor signals (inset) from its tail are recorded during the imaging session using a pair of electrodes. Visual stimuli (forward drifting gratings) for triggering swimming responses are presented below the fish. (FIG. 8B) Left panel: anatomical location of the imaged brain region (midbrain nucleus; see FIG. 42A). Center, a representative field of view of the imaged region expressing Voltron. Scale bar, 20 µm. Right, the position of neurons analyzed in FIG. 8C. (FIG. 8C) Left panel: periods of visual motion (pink) and swim signals (grey) are plotted above Voltron fluorescence traces (black) simultaneously recorded from 11 neurons shown in FIG. 8B. Right panel: zoom of swimming signals (top) and Voltron fluorescence traces from two representative neurons (bottom) are expanded from the dashed box in the left panel. Dots on the top of each trace represent spikes recognized by the algorithm described in FIG. 42B-C. Downward triangles and dotted gray lines indicate initiation of each swim bout. (FIG. 8D) Mean subthreshold signal (top), mean spiking frequency (middle) and spike raster plots (bottom) near the initiation of swim bouts from three representative neurons: "Off" (green), "Onset" (red) and "Late" (blue) neuron. Shadows in the top and middle panels represent s.e.m. across swim events. (FIG. 8E) Classification of recorded neurons by their mean subthreshold signals near the initiation of swim bouts. 179 neurons recorded from 43 fish were classified using non-negative matrix factorization and colored according to the weights for three factors: "onset" (red), "off" (green) and "late" (blue). The details of this classification are described in the Methods. (FIG. 8F) Spatial organization of the same population of neurons as in FIG. 8E. Neurons from multiple fish are superimposed to a single map based on the distance from the center of this midbrain nucleus. (FIG. 8G) Hypothetical model of neural activity modulation in this midbrain nucleus. "Onset" neurons send motor commands to downstream motor circuits to trigger swim bouts, while activity of "off" neurons is inhibited. "Late" neurons receive internal copy signals of ongoing swim bouts from the motor circuit.

(FIG. 9A) Bar graph shows number of residues truncated from 0-22 amino acids. (FIG. 9B) Chemical structure of $_{JF549}$. (FIG. 9C) Image of primary neuron cells expressing Voltron labeled with $_{JF549}$. Scale bar: 20 µm (FIG. 9D) Imaging of spontaneous activity in neuron culture with QuasAr2-HaloTag-16 labeled with JF$_{549}$.

Figure 10:
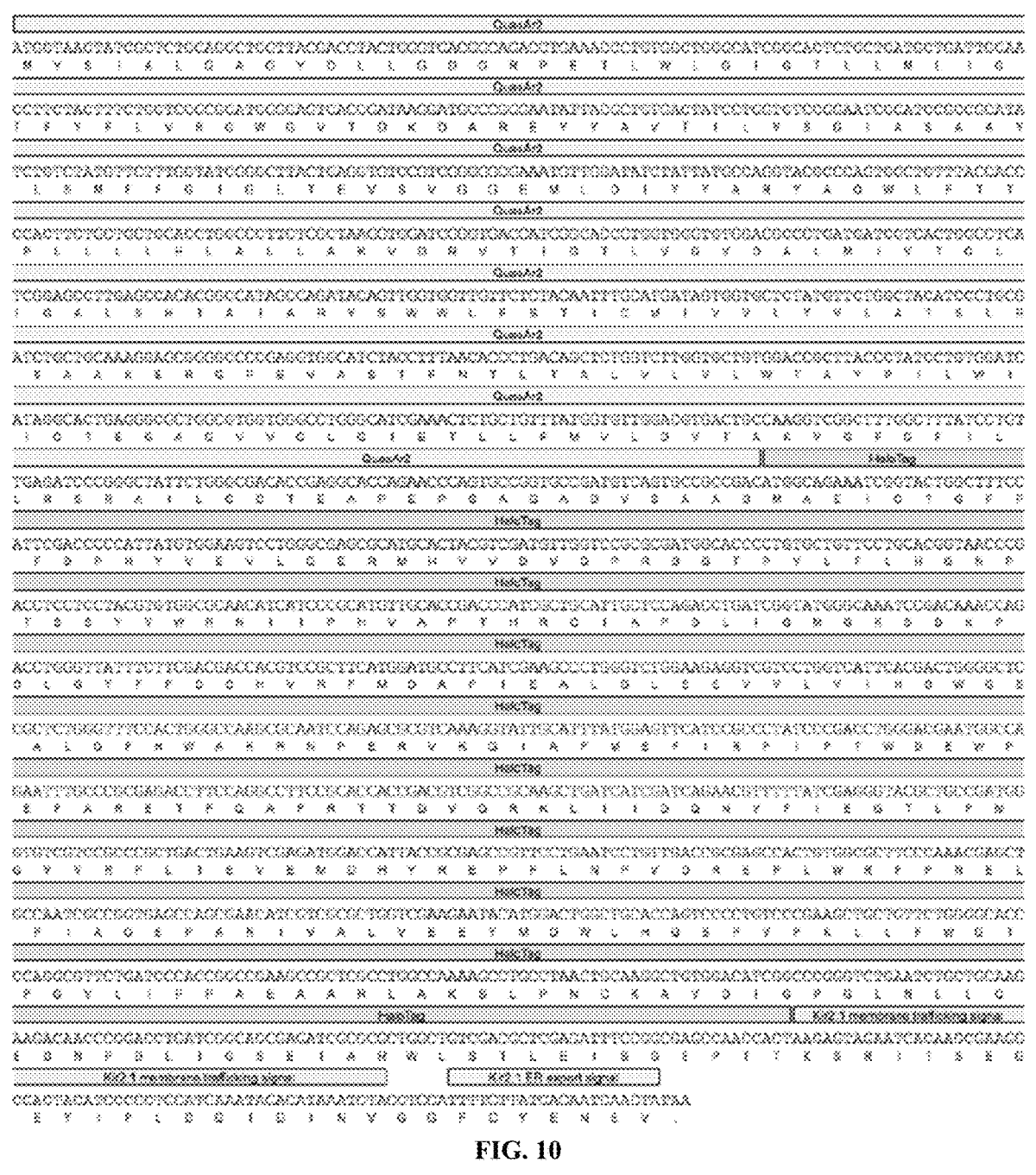

FIG. 10 includes the nucleotide sequence (SEQ ID NO: 21) and amino acid sequence (SEQ ID NO: 22) of QuasAr2-HaloTag, with sequence features annotated.

FIG. 11 includes the nucleotide sequence (SEQ ID NO: 23) and amino acid sequence (SEQ ID NO: 24) of QuasAr2-SNAP-Tag, with sequence features annotated.

FIG. 13A-13C include (from top to bottom: JF505, JF549, JF585, JF635) FIG. 13A: images of neurons expressing Voltron and labeled with different JF-HaloTag dye conjugates, Scale bar: 20 µm; FIG. 13B: Single-trial recording of action potentials and subthreshold voltage signals from current injections. Raw fluorescence traces, colored by dye emission, are shown on the top of each panel. Membrane potential, recorded with a patch pipette, is shown at the bottom of each panel in black; and FIG. 13C: Voltron fluorescence change as a function of membrane voltage with different JF dye conjugates.

FIG. 21A: A schematic drawing showing the configuration of the experiment and the location of the images in the subsequent panels. FIG. 21B: A single plane of two-photon image of the patched cell expressing Voltron (yellow) in the background of scanned Dodt gradient contrast (grey). FIG. 21C: A widefield image showing the location of the region of interest used to extract Voltron signal in the following panels. FIG. 21D: Traces of Voltron fluorescence (above) and whole-cell recording (below). Spikes are indicated by asterisks. FIG. 21E: Traces of denoised Voltron fluorescence (above) and whole-cell recording (below). A small subthreshold event is indicated by an arrow.

FIG. 22A: Infrared image of fly brain overlaid with Voltron549 florescence in a dopamine neuron. Voltron expression was driven by a split-Gal4 driver (MB058B-Gal4) that labels a pair of PPL1-α'2/α2 dopamine neurons, one on each brain hemisphere. FIG. 22B: PPL1-α'2/α2 neurons receive dendritic input from the ipsilateral hemisphere, and send axonal output bilaterally to form patch-like innervations in both the ipsilateral (ipsi.) and contralateral (contra.) mushroom body lobes. Consequently, each projection zone in the mushroom body contains axonal terminals of both cells, although each cell body contributes more extensive arbor to the projection zone in the same hemisphere. FIG. 22C-22E: Voltron imaging in different neuronal compartments. Left, single-trial recordings of fluorescence traces and cell membrane potential from concurrent whole-cell recording. Circles mark action potential spikes detected in the Voltron traces. In dendrites, there was a perfect match between spikes detected from Voltron and from whole-cell recording. In axons, about half of spikes on the Voltron traces were contributed by the sister cell whose soma is in the opposite hemisphere. When these spikes were segregated (see methods), the remaining events aligned with whole-cell recording with marginal error (3 false positive from 447 Voltron spikes, 7 false negative from 451 whole-cell recording spikes). Note that Voltron traces from the soma could not be imaged while recording in whole-cell mode. Right, spike waveforms aligned to their peaks. For axon, both Voltron spike waveforms were from the ipsilateral traces. FIG. 22F: Signal-to-noise ratios (SNRs) in different neuronal compartments, calculated as Voltron spike peak amplitude over standard deviation of the spike-free zones of the trace.

FIG. 28A: Spike triggered averages calculated from traces shown in FIG. 27B. For each pair of neurons, estimated spike times of the first neuron (cell-pre, rows) were used to calculate the average membrane potential of the second neuron (cell-post, columns) in a window of 400 ms around the spike times. Diagonal line shown in red is the average spike shape of each neuron. FIG. 28B: Schematic to illustrate calculation of spike triggered average. FIG. 28C: Zoom-in of spike triggered average for cell 15 (pre) to cell 19 (post). Gray bar: standard deviation of shuffled spike triggered average. FIG. 28D: Estimated optical cross talk between a pair of neurons. For neurons very close to each other, there was apparent optical cross-talk between the neurons which makes the spike triggered average calculated in this way unreliable. Blue line: distance threshold based on which pairs of neurons were excluded in FIG. 28A. Excluded neuron pairs are shown as white squares in FIG. 28A.

FIG. 42A: Left, anatomical location of the midbrain nucleus imaged in this study. The image was taken from plane 81 of image stacks from Tg(eval3:H2B-RFP) (gray) and Tg(vglut2:GFP) (green) transgenic zebrafish in the Z-brain atlas(33). Right, a representative image of the same nucleus in a Tg(vglut2:Gal4); Tg(UAS:GFP) transgenic zebrafish. FIG. 42B: Flow chart of the data processing pipeline for the acquired data. FIG. 42C: An example of pixel weight optimization for a representative neuron. Traces from the initial pixel weights (middle) and the final pixel weights (bottom) of the same neurons are plotted on the right. FIG. 42D: Schematic of averaging procedure of neural activity at the onset of first bout of the swimming for each trial for the analysis in FIG. 42E. FIG. 42E: Average firing rates (top) and raster plots across trials (bottom) at the onset of the first bout for each trial plotted for 3 representative neurons on a long timescale (~3 seconds to 3 seconds). The example 'Off' neuron shows suppression of firing at the onset of swimming (following a brief increase in firing rate just before swimming). The 'Ramp' neuron shows a gradual increase in activity starting about 1.5 seconds before the onset of swimming, and a decay in activity after swim onset. 'Motor'-type neurons (subdivided into 'Onset' and 'Late' neurons in FIG. 8) show increased firing at the onset of swimming. Shadows represent standard error of the mean (s.e.m.) across multiple trials.

DESCRIPTION OF EXEMPLARY EMBODIMENTS

Figure 1A:
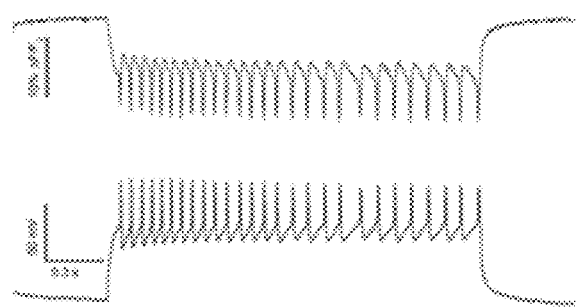
FIGS. 1A-1D includes fluorescence response (top) and membrane potential changes in neutrons (bottom) for GEVIs including Voltron (FIG. 1A), Voltron D92N (FIG. 1B), Voltron N81D D92N (FIG. 1C), and Voltron N81D D92N E199V (FIG. 1D).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a genetically encoded voltage indicators (GEVI) with a direction of fluorescence change such that an increase in membrane potential leads to an increase in fluorescence.

The presently-disclosed subject matter includes voltage indicators and methods of measuring voltage. In some embodiments, the voltage indicators include membrane-localized voltage-sensitive protein and a capture protein engineered to capture a fluorescent dye ligand. These voltage indicators combine the brightness and photostability of robust fluorescent dyes with the targetability of proteins. In this regard, the voltage indicators of the presently-disclosed subject matter include amino acid sequences to improve/localize membrane targeting, such that membrane potential/membrane voltage can be assessed. When the voltage indicator is targeted to a cell membrane, an increase in voltage across the cell membrane causes an increase in fluorescent emission from a fluorescent dye ligand associated with the voltage indicator.

As described herein, the voltage indicators of the presently-disclosed subject matter are uniquely designed to provide a number of benefits that allow for a rapid increase in a robust fluorescent signal in response to spikes in voltage across the membrane. It is also notable that, for example in the case of a neuron, the voltage indicators provide for a rapid increase in a robust fluorescent signal in response to spikes, as well as in response to subthreshold voltage signals. Embodiments of the indicators have sub-millisecond response times between an increase in voltage and an increase in florescent emission. As will be appreciated by those of ordinary skill in the art, the ability to rapidly assess voltage increases with an increase in fluorescence is of particular utility, for example, to reduce noise and enhance sensitivity.

The presently-disclosed subject matter includes a voltage indicator, which comprises a voltage-sensitive protein including amino acid mutations, and a capture protein domain arranged and disposed to capture a fluorescent dye ligand. Beneficially, when the fluorescent dye ligand is captured by the capture protein domain, and when the voltage indicator is bound to a membrane, an increase in voltage across the membrane causes an increase in fluorescent emission from the fluorescent dye ligand. In some embodiments, the membrane is a membrane of a neuron. In this regard, the increase in voltage, whether a spike in voltage or a subthreshold voltage signal, results in an increase in fluorescent emission correlating to the voltage. In some embodiments, the response time between the increase in voltage and the increase in fluorescent emission is less than about a millisecond.

Suitable voltage sensitive proteins include, but are not limited to, one or more opsins, one or more other molecules including a voltage-sensing domain, or a combination thereof, and including amino acid mutations. For example, in some embodiments, the voltage-sensitive protein is a voltage-sensitive opsin domain. In some embodiments, the voltage-sensitive opsin domain is a microbial opsin domain. In some embodiments, the voltage-sensitive opsin domain is a microbial rhodopsin domain.

"Microbial rhodopsins" are a large class of proteins characterized by seven transmembrane domains and a retinilydene chromophore bound in the protein core to a lysine via a Schiff base. Over 5,000 microbial rhodopsins are known, and these proteins are found in all kingdoms of life. Microbial rhodopsins serve a variety of functions for their hosts: some are light-driven proton pumps (bacteriorhodopsin, proteorhodopsins), others are light-driven ion channels (channelrhodopsins), chloride pumps (halorhodopsins), or serve in a purely photosensory capacity (sensory rhodopsins). The retinilydene chromophore imbues microbial rhodopsins with unusual optical properties. The linear and nonlinear responses of the retinal are highly sensitive to interactions with the protein host: small changes in the electrostatic environment can lead to large changes in absorption spectrum. These electro-optical couplings provide the basis for voltage sensitivity in microbial rhodopsins.

In some embodiments, the microbial rhodopsin domain is selected from the group consisting of QuarsAr1, QuarsAr2, Ace2N, and combinations thereof. In another embodiment, the voltage sensitive protein includes a Ciona intestinalis voltage-sensing domain (CiVSD), Danio rerio voltage-sensing domain (DrVSD), Gallus gallus voltage-sensing domain (GgVSD), or a combination thereof.

In some embodiments, the microbial rhodopsin domain comprises an amino acid sequence having at least 90, 95, 98, or 99% sequence identity to SEQ ID NO: 9, SEQ ID NO: 15, SEQ ID NO: 16, or SEQ ID NO: 17.

In some embodiments, the voltage-sensitive opsin domain is Ace2N including an amino acid mutation at one or more of residue 81, 92, and 199. In some embodiments, the voltage-sensitive opsin domain comprises the polypeptide of SEQ ID NO: 9 having one, two, three, or four amino acid mutations. In some embodiments, the voltage-sensitive opsin domain comprises the amino acid sequence of SEQ ID NO: 9 having an amino acid mutation at one or more of residue 81, 92, and 199.

In some embodiments, the voltage indicator includes an amino acid sequence selected from SEQ ID NOS: 2, 4, 6, 8, 20, 22, 24, and 26. In some embodiments, the voltage indicator includes an amino acid sequence encoded by a nucleotide sequence selected from the group of nucleotide sequences of SEQ ID NOS: 1, 3, 5, 7, 19, 21, 23, and 25.

Suitable capture proteins include any protein configured to bind a desired ligand. For example, in one embodiment, the capture protein includes a covalent capture protein. In some embodiments, the capture protein of the voltage indicator is a non-covalent capture protein. In some embodiments, the non-covalent capture protein is selected from the group consisting of TMP-tag, biotin-avidin, and a combination thereof. In some embodiments, the capture protein domain is selected from a HaloTag and a SNAP-Tag. In some embodiments, the capture protein is a covalent capture protein. In some embodiments, the covalent capture protein is selected from the group consisting of HaloTag, SNAP-tag, TMP-tag, βLac-tag, CLIP-tag, or a combination thereof. In some embodiments, the capture protein domain comprises an amino acid sequence selected from the amino acid sequence of SEQ ID NOS: 10 and 11.

In some embodiments, 1, 2, 3, 4, 5, 6, 7, 8, 9, or 10 amino acids are removed from the junction between the opsin domain and the capture protein.

In some embodiments, in addition to the voltage-sensitive protein domain and the capture protein domain, the voltage indicator also includes a targeting sequence. In some embodiments, the targeting sequence is a soma targeting sequence for directing the indicator to a neuron. In some embodiments, the targeting sequence comprises the amino acid sequence of SEQ ID NO: 12.

In some embodiments, the mutated voltage-sensitive microbial opsin domain and the capture protein are provided as a fusion protein. In some embodiments, the capture protein is positioned at the c-terminal end of the voltage-sensitive microbial opsin domain. In some embodiments, the indicator also includes a targeting sequence that is positioned at the c-terminal end of the capture protein.

As noted herein above, the voltage indicator includes a capture protein domain arranged and disposed to capture a fluorescent dye ligand. Suitable fluorescent dye ligands include, but are not limited to, one or more fluorophore dyes. In one embodiment, the fluorophore dye includes a fluorophore containing one or more cyclic amine substituents. In another embodiment, the fluorescent dye ligand is an azetidine-containing Janelia Fluor™ dyes. For example, the fluorescent dye ligand can be Janelia Fluor™$_{505}$, Janelia Fluor™$_{525}$, Janelia Fluor™$_{549}$, Janelia Fluor™$_{585}$, Janelia Fluor™$_{646}$, or combinations thereof. In some embodiments, the fluorescent dye ligand is a fluorescent protein. For example, the fluorescent dye ligand can be sfGFP or mNeon-Green.

The presently-disclosed subject matter also includes methods of measuring voltage, and in particular, methods of measuring voltage across a membrane. The voltage indicators as described herein are used to perform the method.

In some embodiments, the method involves administering the voltage indicator and determining changes in fluorescence of the fluorescent dye ligand. When the fluorescent dye ligand is captured by the capture protein domain, and when the voltage indicator is bound to a cell membrane, an increase in voltage across the cell membrane causes an increase in fluorescent emission from the fluorescent dye ligand. In this regard, the method can involve determining changes in voltage based on changes in fluorescence. In some embodiments, an increase in membrane potential leads to an increase in fluorescence.

The method can be used to measure voltage across the membrane of a cell, such as a neuron. Florescent emission will increase with an increase in voltage, which can be a spike in voltage or a subthreshold voltage signal. In some embodiments, the response time between the increase in voltage and the increase in fluorescent emission is less than about a millisecond.

The changes in fluorescence may be measured through any suitable method such as, but not limited to, observation with a microscope, image capture, video recording, or a combination thereof.

In some embodiments, the voltage indicator includes a linker between the voltage-sensitive domain and the capture protein domain. Embodiments of the indicator and method can include modifying a length of the linker. For example, modifying the length of the linker can include removing at least one amino acid residue. In some embodiments, about 1, 2, 3, 4, 5, 6, 7, 8, 9, 10, 11, 12, 13, 14, 15, 16, 17, 18, 19, 20, 21, or 22 amino acid residues can be removed. In some embodiments, the modification of the length of the linker can modify the size of a fluorescence response.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1

Through mutagenesis, the present inventors inverted the direction of fluorescence change in exemplary rhodopsin electrochromic fluorescence resonance energy transfer (eFRET) genetically encoded voltage indicators (GEVIs) such that an increase in membrane potential lead to an increase in fluorescence. Several different single amino acid substitutions inverted the fluorescence change of an exemplary eFRET GEVI (i.e., an amino acid substitution relative to the sequence of FIG. 4).

Figure 1B:
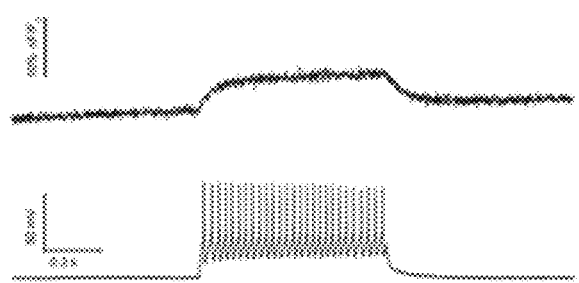
Figure 4:
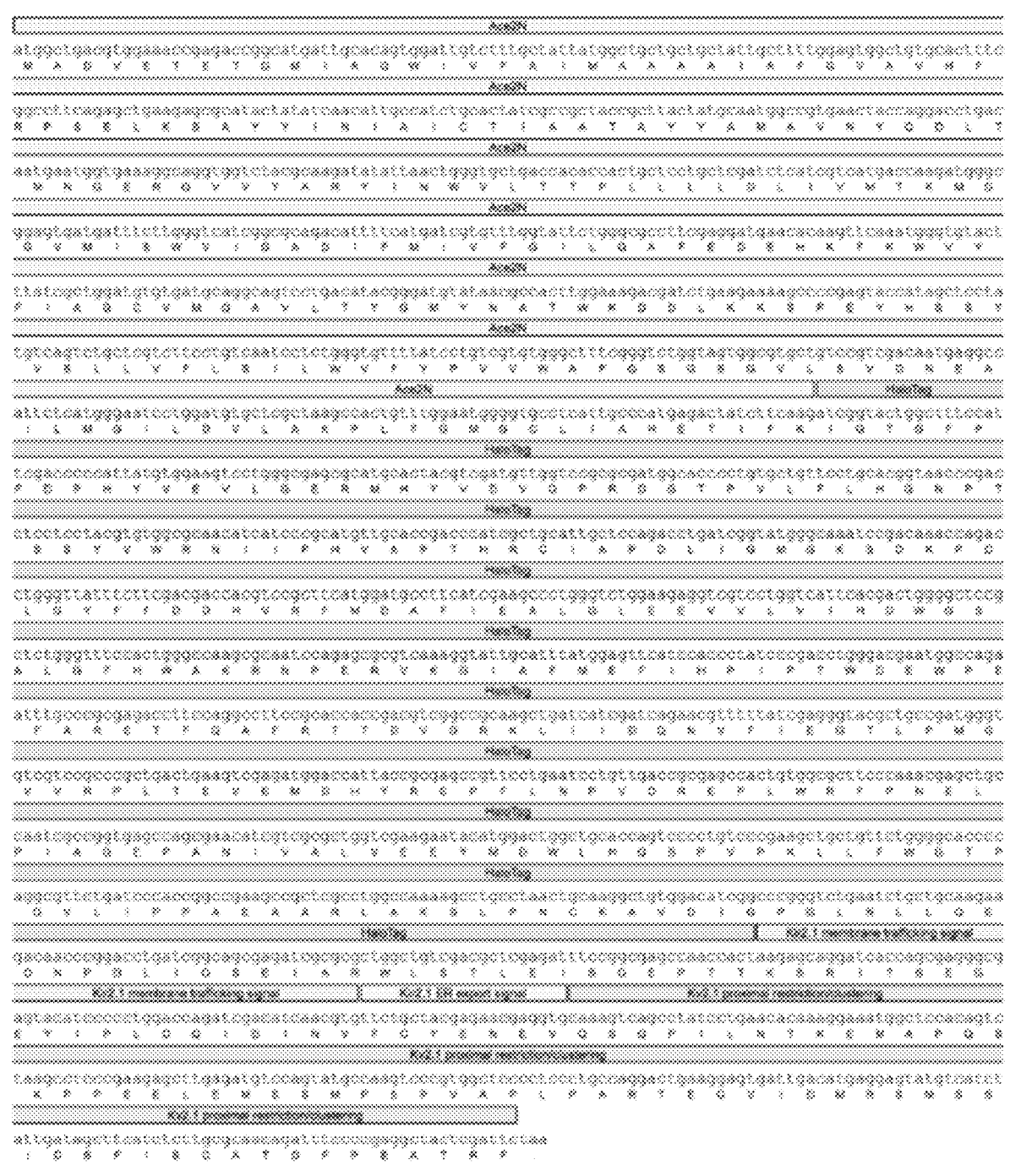

By way of comparison, FIG. 1A illustrates fluorescence change of an exemplary eFRET GEVI having the sequence as set forth in FIG. 4, where there is a decrease in fluorescence with increasing membrane potential, and voltage signals such as action potentials in neurons take on a downward-going shape. Meanwhile, FIGS. 1B-D illustrate fluorescent change in exemplary eFRET GEVIs having one or more amino acid substitutions relative to the sequence of FIG. 4, in which the fluorescence change is inverted.

In one embodiment, D92N (SEQ ID NO: 2), a single amino acid substitution inverted the florescence change (FIG. 1B), but it was desired to see if the indicator could be further modified such that fluorescence changes occur more-rapidly to follow fast voltage changes such as action potentials in neurons.

Figure 1C:
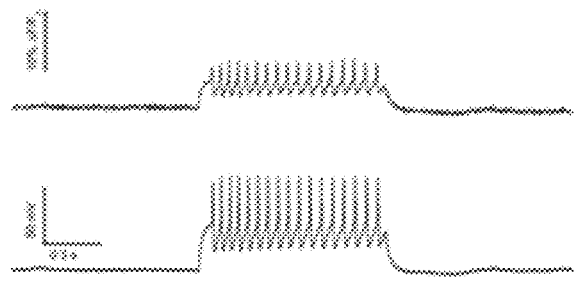

An additional amino acid substitution, N81D, increased the speed of fluorescence change such that the fluorescence could follow action potentials in neurons (FIG. 1C). The magnitude of N81D D92N (SEQ ID NO: 4) remained small relative to the indicator of FIG. 4.

Figure 1D:
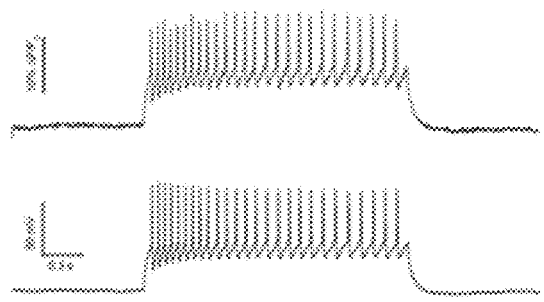
Figure 2:
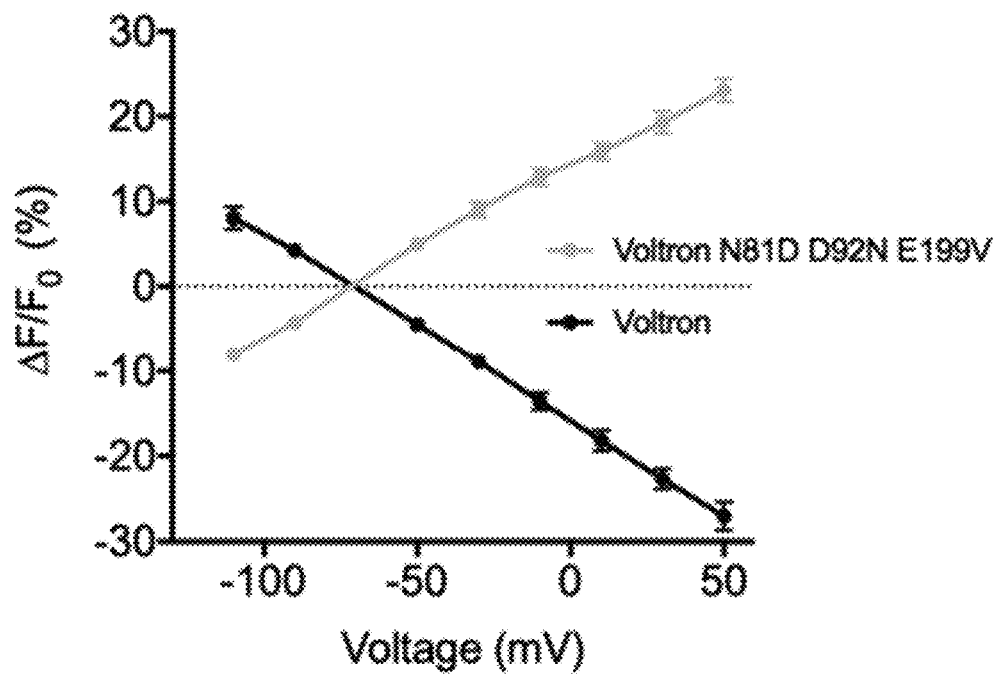
FIG. 2 includes fluorescence versus voltage in neurons for Voltron and Voltron N81D D92N E199V.
Figure 3:
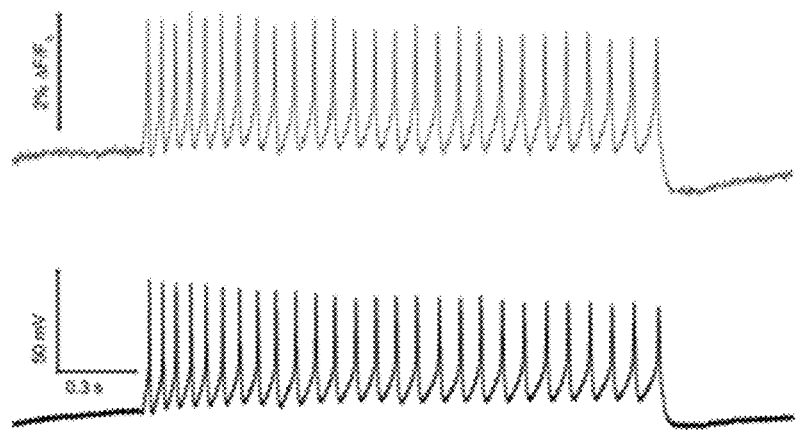
FIG. 3 includes fluorescence response (top) and membrane potential changes in neutrons (bottom) for Ace2-mNeonGreen N81D D92N.

An additional amino acid substitution (E199V) increased the sensitivity such that the fluorescence change of N81D D92N E199V (SEQ ID NO: 6) was equal in amplitude to the indicator of FIG. 4, but with an inverted response direction (FIG. 1D and FIG. 2). The present inventors additionally showed that these amino acid changes invert the signal when a fluorescent protein (Ace2-mNeonGreen N81D D92N (SEQ ID NO: 8)) is used in place of a rhodamine dye (FIG. 3).

Example 2

Voltron was used for in vivo voltage imaging in mice, zebrafish, and fruit flies. In mouse cortex, Voltron allowed single-trial recording of spikes and subthreshold voltage signals from dozens of neurons simultaneously, over 15 minutes of continuous imaging. In larval zebrafish, Voltron enabled the precise correlation of spike timing with behavior.

An exemplary design for a chemigenetic voltage indicator combined a voltage-sensitive microbial rhodopsin domain (6, 7, 11) with a self-labeling protein tag domain (FIG. 5A) that covalently binds a synthetic fluorophore dye ligand (14, 15) (FIG. 5B), analogous to previously reported voltage indicators using fluorescent proteins (10, 11, 18). Transmembrane-voltage-dependent changes in the absorption spectrum of the rhodopsin (6, 19) reversibly modulate the degree of fluorescence quenching of the nearby bound dye through Förster resonance energy transfer (FRET).

The modularity of this approach was investigated, and three different exemplary rhodopsin domains, QuasAr1 (7), QuasAr2 (7), and Ace2N (11, 20), were all able to modulate the fluorescence of $JF_{549}$ bound to either HaloTag (15) or SNAP-tag (21) self-labeling tag domains (FIGS. 9 to 15). Removing a modest number of amino acid residues at the junction of the rhodopsin and self-labeling tag domains increased the amplitude of fluorescent voltage signals (FIG. 9), presumably by decreasing average distance and thus increasing FRET efficiency between the dye and rhodopsin retinal cofactor. The configuration providing the best signal-to-noise ratio for spikes was Ace2N fused to HaloTag with five amino acids removed at their junction (FIGS. 5A, 5B and 4), hereafter referred to as Voltron.

Figure 16:
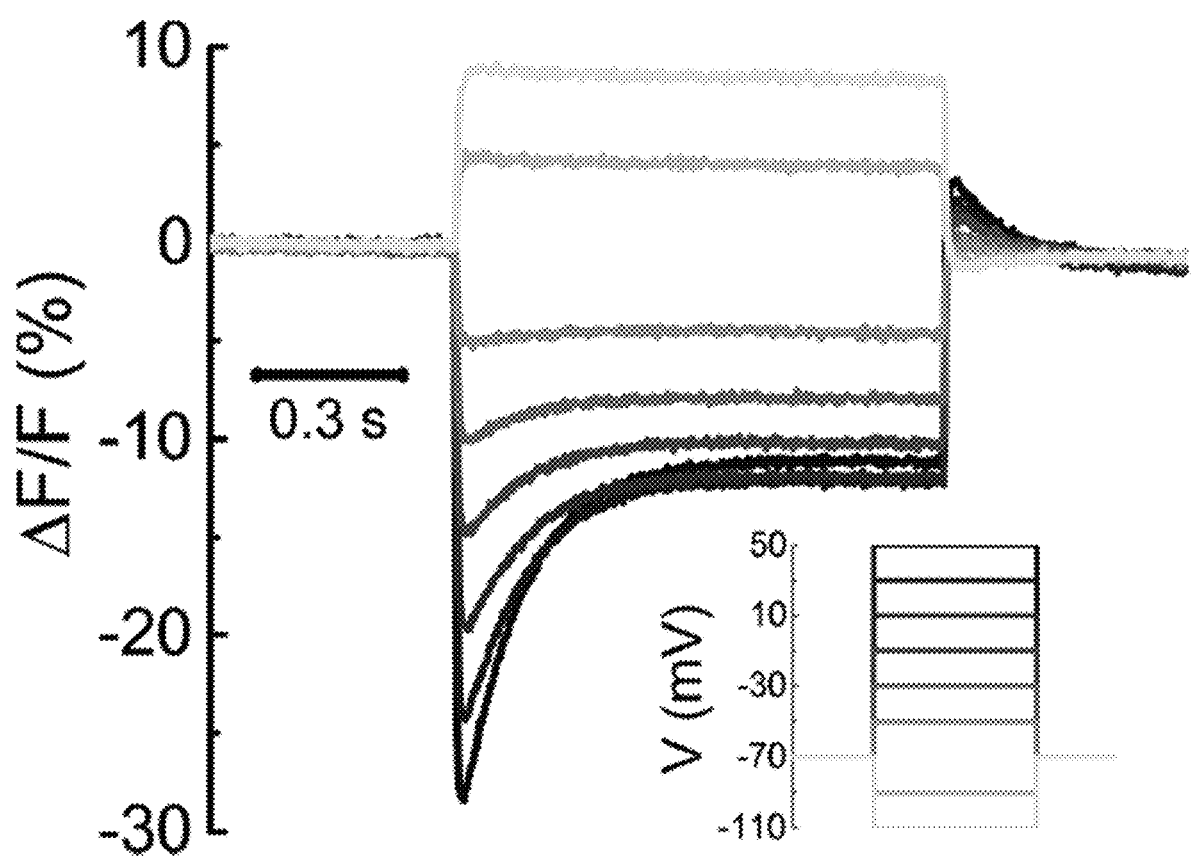
Figure 17:
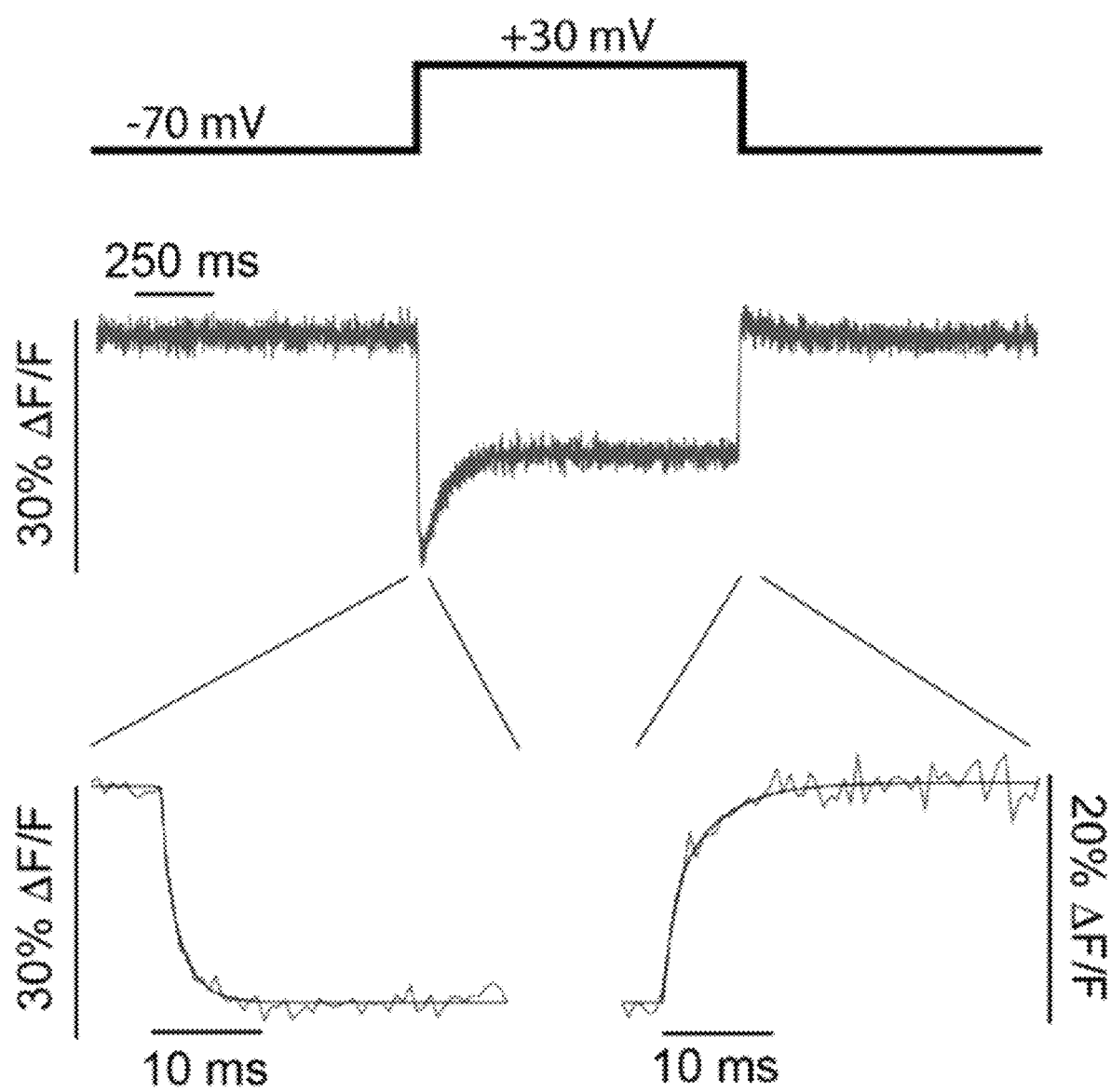
FIG. 17 illustrates a representative fluorescence response of Voltron525 in a cultured neuron to a 100 mV potential step delivered in voltage clamp. Insets: Zoom in on change of Voltron fluorescence to depolarization and hyperpolarization. Solid black line is double exponential fit according to $\Delta F/F(t)=Ae^{t/\tau_{fast}}+Be^{t/\tau_{slow}}$. Image acquisition rate 3.2 kHz. For full kinetics data, see Table 1.

Voltron was tested in neuron cultures using high-speed imaging with simultaneous whole-cell patch clamp electrophysiology (FIG. 5C), first investigating different dye—Voltron combinations. Voltron could detect neuronal action potentials and sub-threshold potential changes using a range of JF dye ligands with emission maxima between 520 nm and 660 nm (FIGS. 5C-5E and 13). Voltron bound to $_{JF525}$ (i.e., Voltron525) exhibited the highest sensitivity, giving a fluorescence change of −23±1% for a voltage step from −70 mV to +30 mV (FIG. 5E and FIG. 16); Voltron549 showed similar sensitivity. Voltron525 responded to voltage steps with sub-millisecond on and off time constants (Table 1 and FIG. 17).

TABLE 1

Voltron525 and Ace2N-mNeon kinetics in primary neuron culture cells

| | Activation (−70 mV to 30 mV) | | | Deactivation (30 mV to −70 mV) | | |
|---|---|---|---|---|---|---|
| | $\tau_{fast}$ (ms) | $\tau_{slow}$ (ms) | % fast | $\tau_{fast}$ (ms) | $\tau_{slow}$ (ms) | % fast |
| Ace2N-mNeon | 0.59 ± 0.10 | 6.9 ± 0.5 | 62 ± 3 | 0.63 ± 0.09 | 6.0 ± 1.1 | 55 ± 4 |
| Voltron-JF525 | 0.64 ± 0.09 | 4.1 ± 0.6 | 61 ± 4 | 0.78 ± 0.12 | 3.9 ± 0.2 | 55 ± 7 |

Figure 11:
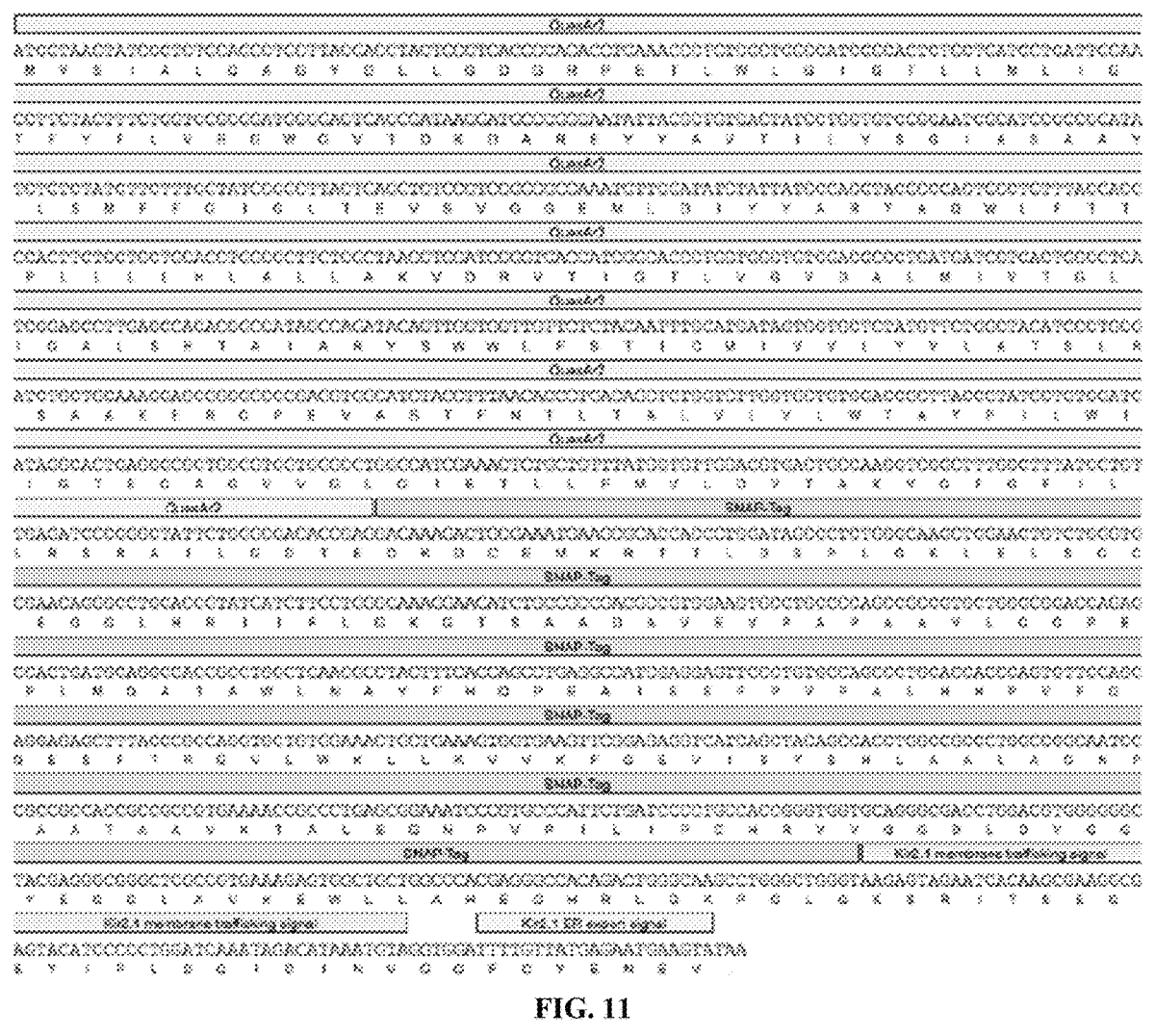

Neurons expressing Ace2N-mNeon and Voltron525 were imaged at 3.2 kHz during whole cell voltage clamp as detailed in the methods section. Fluorescence traces were then fit using a double exponential model (FIG. 11). Errors are s.e.m. n = 7 cells for Ace-mNeon and n = 8 cells for Voltron525.

Figure 7F:
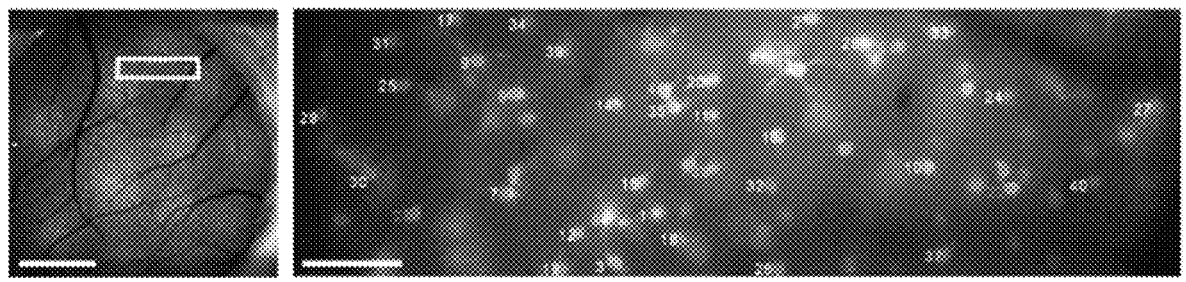
Figure 7G:
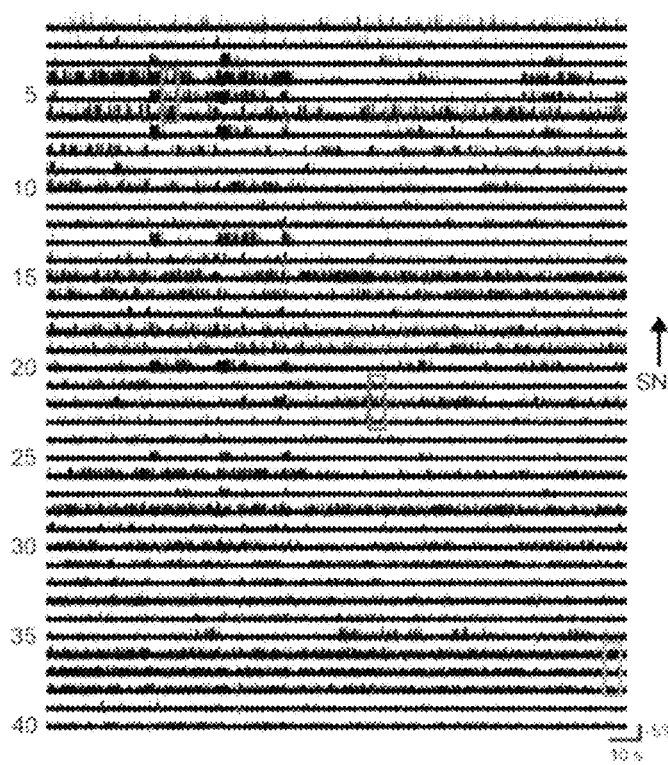
Figure 7G:
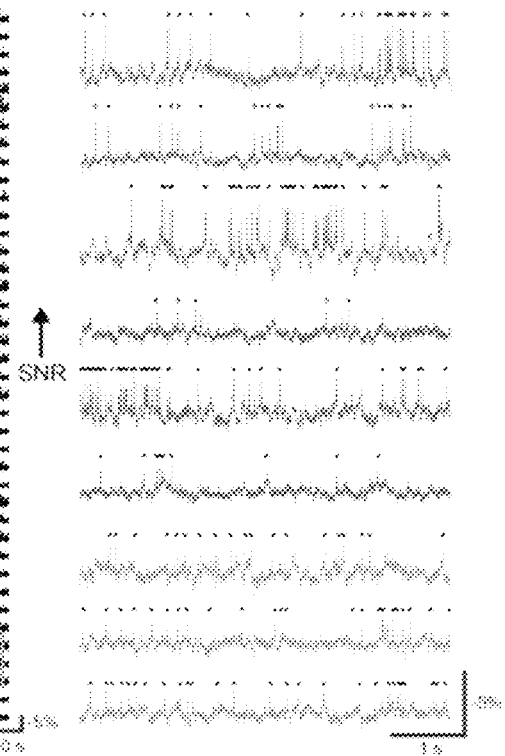
Figure 18:
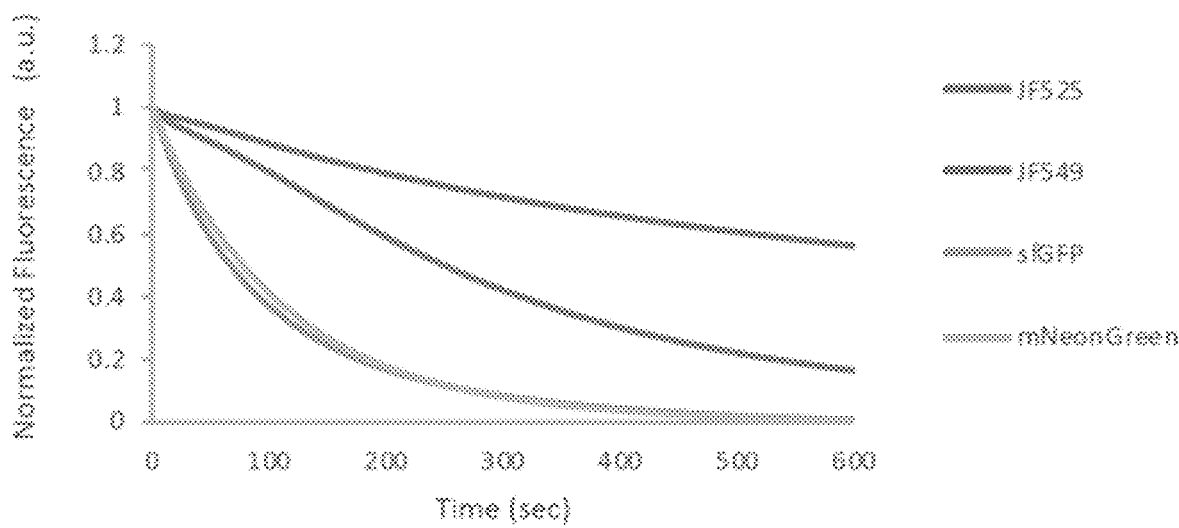
FIG. 18 includes a photobleaching profile of HaloTag-bound JF525, JF549, and fluorescent proteins sfGFP and mNeonGreen, measured in aqueous droplets with widefield microscopy. Data taken at excitation rates W for JF525 (W=1549 s$^{-1}$), JF549 (1540 s$^{-1}$), sfGFP (1597 s$^{-1}$) and mNeonGreen (1772 s$^{-1}$).
Figure 19:
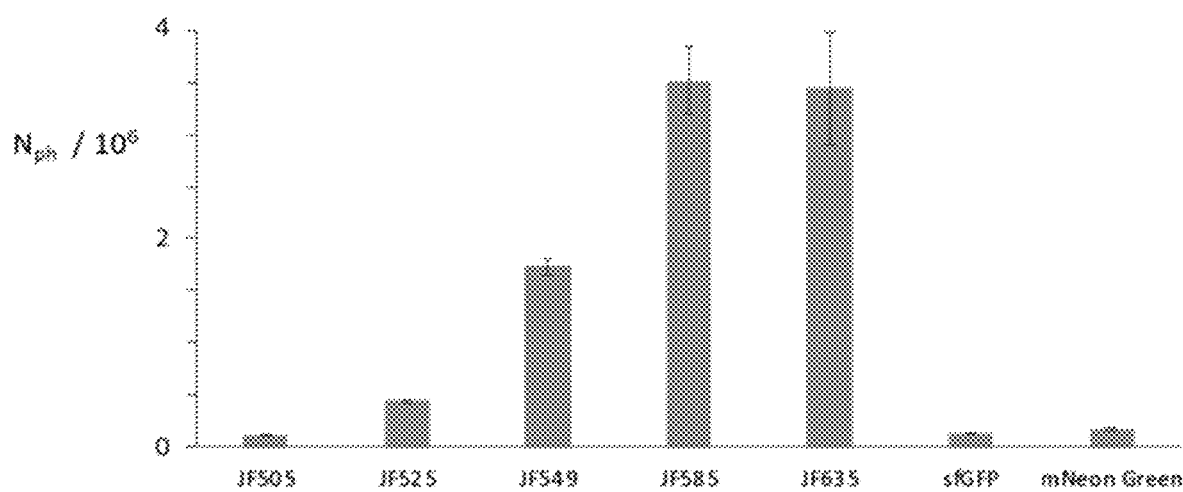
FIG. 19 is a bar graph including mean number of photons per molecule emitted before photobleaching $_{Nph}$ for JFdyes-HT conjugates and fluorescent proteins obtained in aqueous droplets using widefield microscopy. Error bars are standard deviation (n=9).
Figure 20:
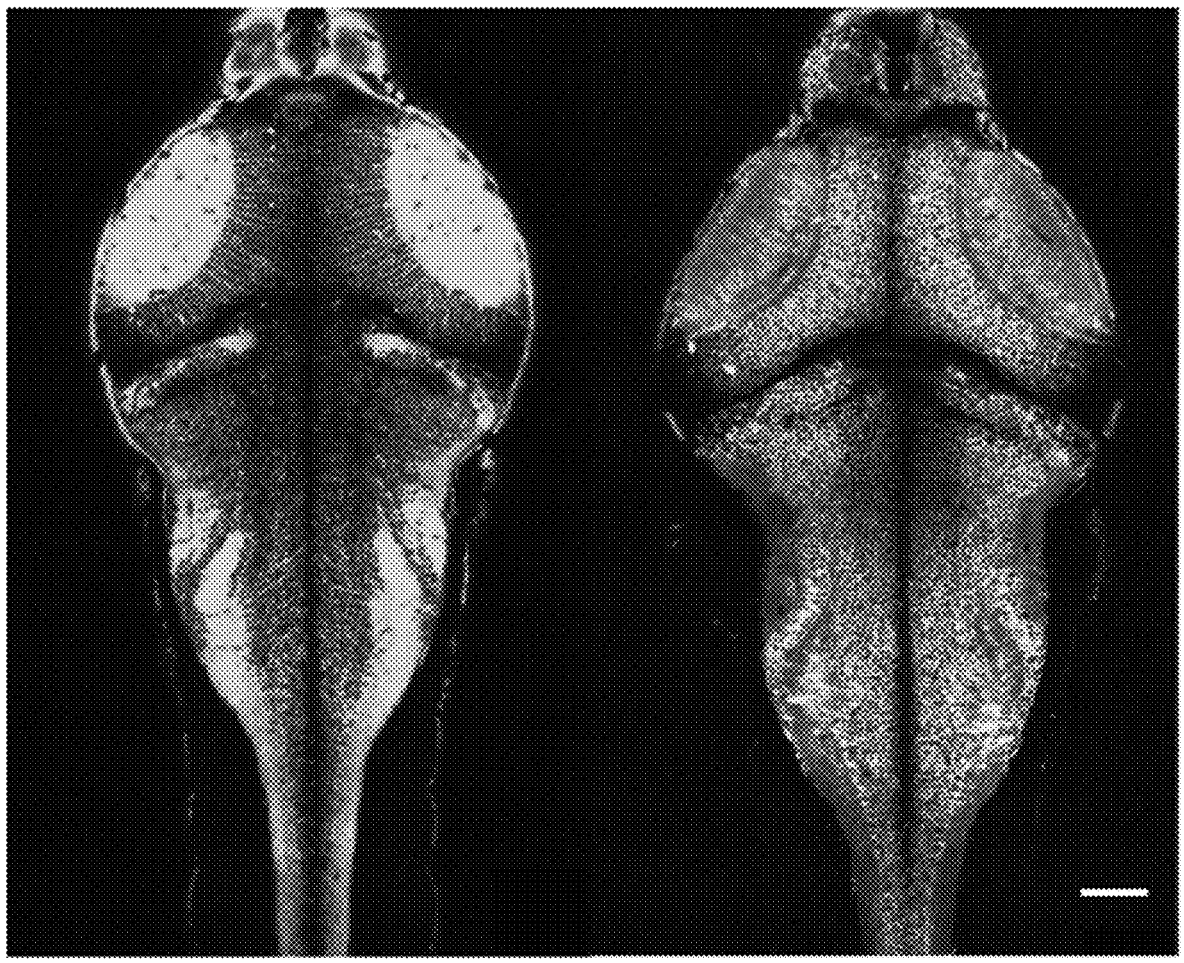
FIG. 20 includes images showing Voltron expression in zebrafish. The left panel includes a confocal image of Tg[elavl3:Voltron], and the right panel includes a confocal image of Tg[elavl3:Voltron-ST] (right) zebrafish (4 dpf) labeled with JF525 dye. Scale bar: 50 µm.
Figure 21A:
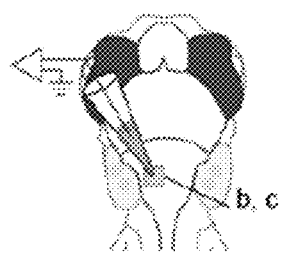
FIG. 21A-21E relate to simultaneous whole-cell recording and Voltron imaging in zebrafish.
Figure 21B:
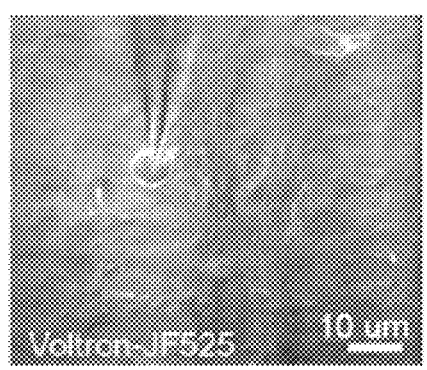
Figure 21C:
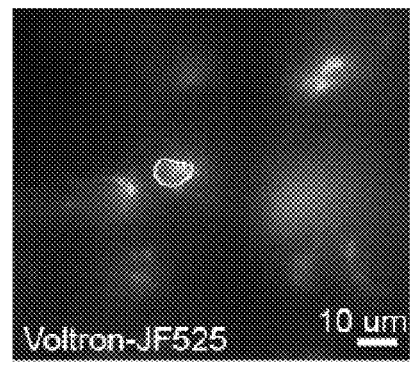
Figure 21D:
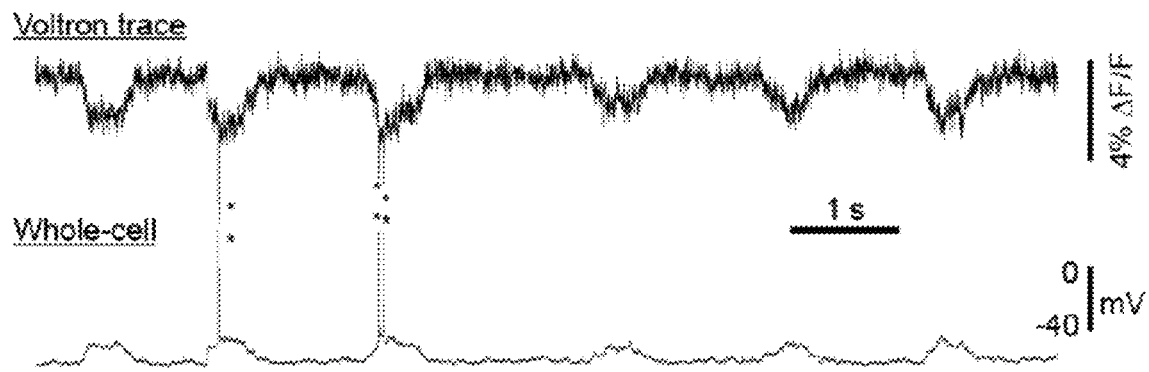
Figure 21E:
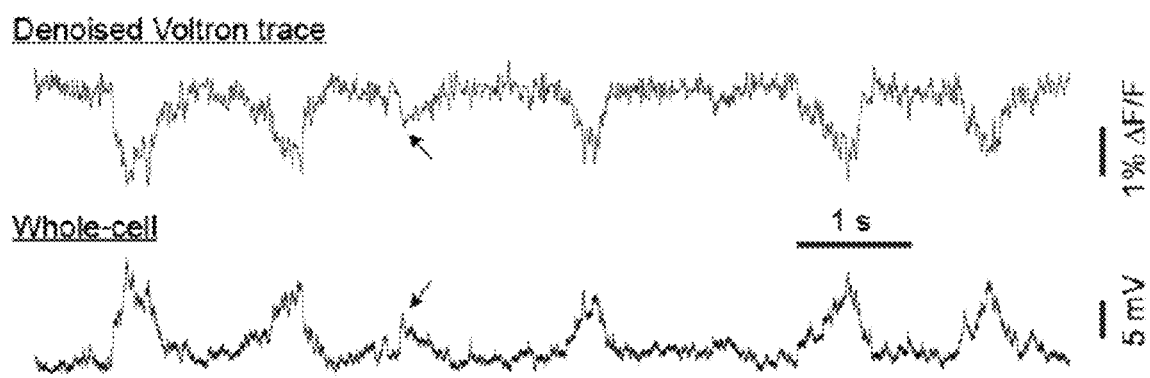

The brightness and photostability of Voltron in neuronal cultures was compared with two other recently described fluorescent protein-based GEVIs: Ace2N-mNeon (11) and ASAP-2f (13). Both Voltron525 and Voltron549 were brighter than Ace2N-mNeon (3-4×) and ASAP-2f (16-18×) (FIG. 5F) in cell culture. This difference was not due to differences in expression levels; the brightness of Voltron549 and Ace2N-mNeon were compared at the single-molecule level, and a similar 3-4× brightness difference was observed (FIG. 5G). Voltron525 and Voltron549 were also more photostable in ensemble measurements (FIG. 5H, Tables 2 and 3 and FIGS. 18,19) as well as in single-molecule assays, where photobleaching times were 8-fold longer for Voltron549 than Ace2N-mNeon (FIG. 5I). Overall, the improved brightness and photostability of Voltron increase the photon yield by at least 10-fold relative to existing GEVIs in neurons.

intensity, imaging duration, and field of view used for in vivo imaging were investigated (FIG. 7). Using widefield microscopy and illumination intensities between 3 and 20 mW/mm$^2$, action potentials from nearby neurons could be clearly identified and distinguished throughout 15 minutes of continuous imaging (SNR=4.4 during final minute); (FIG.

TABLE 2

Photophysical properties of parent fluorophore HaloTag-bound JFdyes and green fluorescent proteins (mean values, n = 9)

| Fluoro-phore | $\lambda$abs (nm) | $\lambda$em (nm) | $\varepsilon_{max}$ (mM$^{-1}$ cm$^{-1}$) | $\Phi_{fl}$ | W$^{(a)}$ (sec$^{-1}$) | $\tau_1$ (A1)$^{(b)}$ (sec) | $\tau_2$ (A2) (sec) | $<\tau_b>^{(c)}$ (sec) | Pb/10$^{-6}$ $^{(d)}$ | N$_{ph}$/10$^5$ $^{(e)}$ | $\tau_{1/2}^{(f)}$ (sec) |
|---|---|---|---|---|---|---|---|---|---|---|---|
| JF505 | 509 | 531 | 56.8 | 0.83 | 941 | 59 (0.59) | 264 (0.41) | 144 | 7.36 | 1.13 | 51 |
| JF525 | 532 | 553 | 83.6 | 0.87 | 1,549 | 329 (1.0) |  | 330 | 1.96 | 4.43 | 336 |
| JF549 | 555 | 578 | 91.3 | 0.86 | 3,158 | 907 (0.65) | 124 (0.35) | 633 | 0.50 | 17.2 | 804 |
| JF585 | 593 | 611 | 109 | 0.83 | 4,443 | 931 (1.0) |  | 950 | 0.24 | 35.1 | 3,320 |
| JF635 | 641 | 656.5 | 64.0 | 0.7 | 2,486 | 1976 (1.0) |  | 1,980 | 0.20 | 34.4 | 3,130 |
| sfGFP | 488 | 511 | 51.5 | 0.66 | 1,597 | 90 (0.66) | 167 (0.34) | 117 | 5.32 | 1.24 | 71 |
| mNeon | 506 | 517.5 | 120 | 0.85 | 1,773 | 102 (0.72) | 144 (0.28) | 114 | 4.83 | 1.80 | 118 |

$^{(a)}$ Excitation rate (absorbed photons/sec) equal to the integral over wavelength of the product of extinction coefficient and spectral irradiance.
$^{(b)}$ Decay constant (normalized amplitude) of multi-exponential fit to the photobleaching decay curve.
$^{(c)}$ Amplitude-weighted lifetime equal to A$_1\tau_1$ + A$_2\tau_2$.
$^{(d)}$ Calculated probability of photobleaching per absorbed photon.
$^{(e)}$ Calculated number of photons emitted per molecule before photobleaching.
$^{(f)}$ Calculated time to bleach from a rate of 1000 to 500 photons per sec per molecule.

TABLE 3

Photobleaching properties of GEVI sensors in neuronal cell culture (mean values, n = 5)

| sensor | W$^{(a)}$ (sec$^{-1}$) | T$_1$ (A$_1$)$^{(b)}$ (sec) | T$_2$ (A$_2$) (sec) | $<\tau_b>^{(c)}$ (sec) | P$_b$/10$^{-6}$ $^{(d)}$ | N$_{ph}$/10$^5$ $^{(e)}$ | T$_{1/2}^{(f)}$ (sec) |
|---|---|---|---|---|---|---|---|
| Voltron525 | 1,549 | 171 (0.84) | 1497 (0.15) | 373 | 1.74 | 5.03 | 206 |
| Voltron549 | 3,158 | 675 (0.67) | 61.5 (0.31) | 471 | 0.672 | 12.8 | 538 |
| ASAP-2f | 1,597 | 400 (0.68) | 24.9 (0.30) | 281 | 2.23 | 2.96 | 132 |
| Ace2N-mNeon | 1,773 | 118 (0.88) | 147 (0.11) | 120 | 4.70 | 1.81 | 119 |

$^{(a)}$ Excitation rate (absorbed photons/sec) equal to the integral over wavelength of the product of extinction coefficient and spectral irradiance.
$^{(b)}$ Decay constant (normalized amplitude) of multi-exponential fit to the photobleaching decay curve.
$^{(c)}$ Amplitude-weighted lifetime equal to A$_1\tau_1$ + A$_2\tau_2$.
$^{(d)}$ Calculated probability of photobleaching per absorbed photon.
$^{(e)}$ Calculated number of photons emitted per molecule before photobleaching.
$^{(f)}$ Calculated time to bleach from a rate of 1000 to 500 photons per sec per molecule.

Figure 6I:
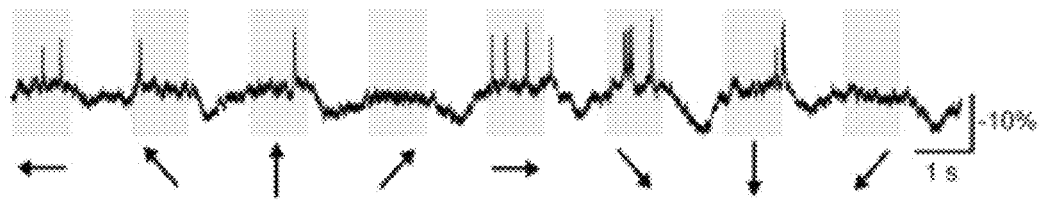
Figures 6J, 6K, 6L:
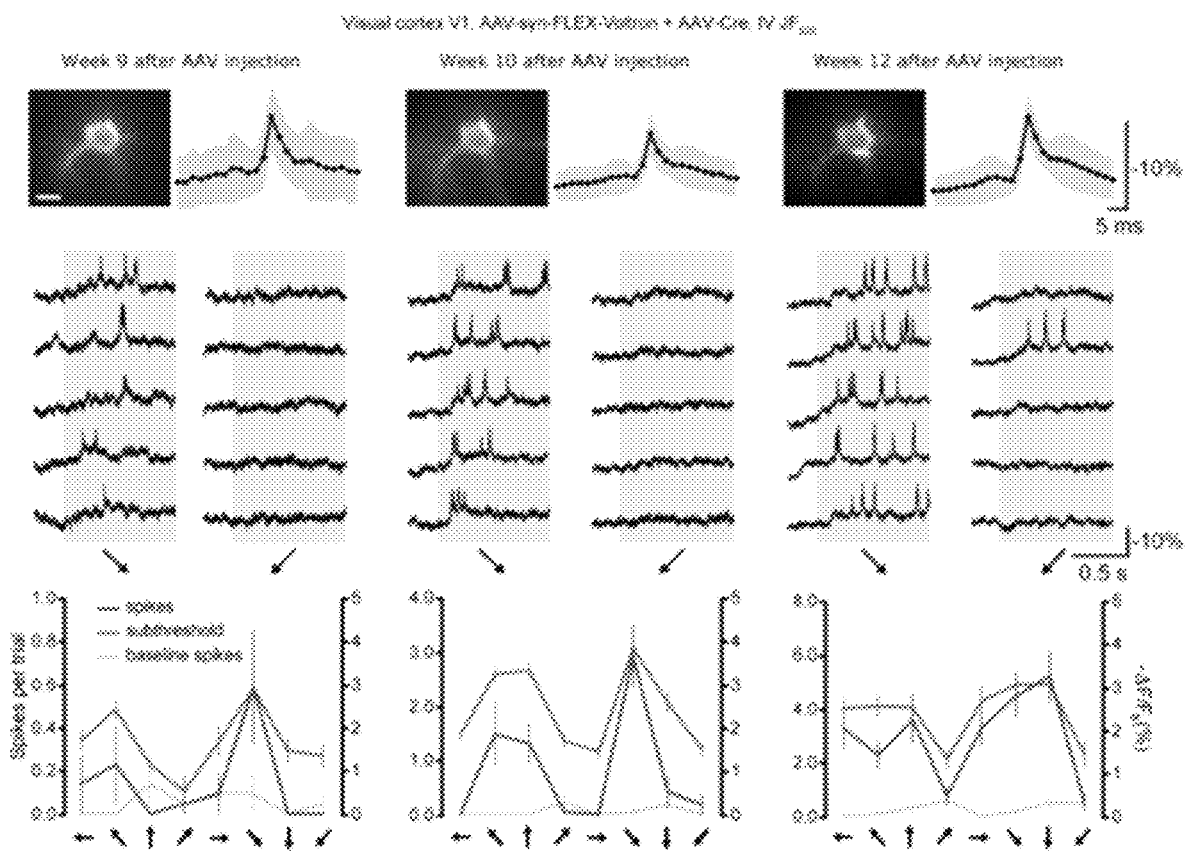

The chemigenetic Voltron indicator was next deployed in vivo, observing that the protein could be reliably expressed and labeled with dye in mice, larval zebrafish, and adult fruit flies (FIGS. 5-8, FIG. 20-41). Simultaneous in vivo electrophysiology and imaging in both zebrafish and flies confirmed the detection of individual action potentials in single-trial imaging (FIG. 5J, 5K and FIGS. 21-22). For imaging in the mouse brain, a variant of Voltron was used with a soma-targeting sequence from Kv2.1 (22, 23) (Voltron-ST, FIG. 23). The rapid kinetics of Voltron525-ST allowed clear observation of action potentials in fast-spiking parvalbumin positive interneurons in the CA1 region of mouse hippocampus (FIG. 6A-6G and FIG. 24). Orientation tuning was measured based on both spiking and subthreshold voltage signals in layer 2/3 pyramidal neurons in mouse primary visual cortex in response to drifting grating stimuli in the contralateral visual field, a benchmark for new indicators (1, 11) (FIG. 6H-6L and FIG. 25-26), and confirmed that spiking activity shows sharper orientation selectivity than subthreshold voltage signals (24). The imaging period was extended over several consecutive weeks by injection of additional JF525 HaloTag ligand prior to each imaging session (FIG. 6J-6L).

To further assess the advantages garnered from Voltron's improved photostability and brightness, the illumination 7B-7E). The field-of-view was expanded to include dozens of cortical interneurons labeled with Voltron525-ST via an NDNF-Cre mouse line (25), while imaging at 400 Hz (FIGS. 7F, 7G, FIG. 27-40). Even with this large field of view, clear signals for spikes and subthreshold voltage signals were observed in ~90% of neurons in focus within the imaging field. Overall, a total of 449 neurons were imaged (12 fields of view in 3 mice), demonstrating routine voltage imaging of populations of neurons in superficial mouse cortex (FIG. 7G, FIG. 27-40). This unprecedented scale of in vivo voltage imaging enabled analysis of membrane potential correlations between many neuron pairs (FIG. 28).

Figure 8A:
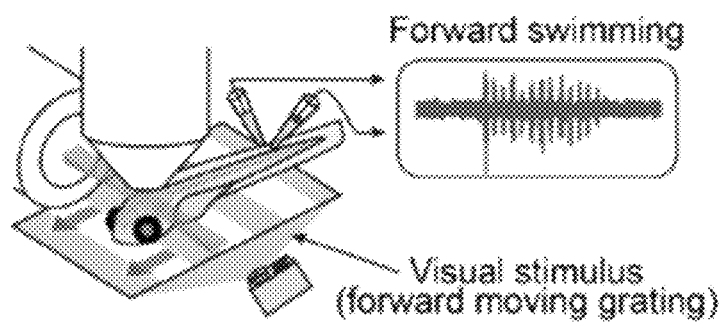
Figure 8B:
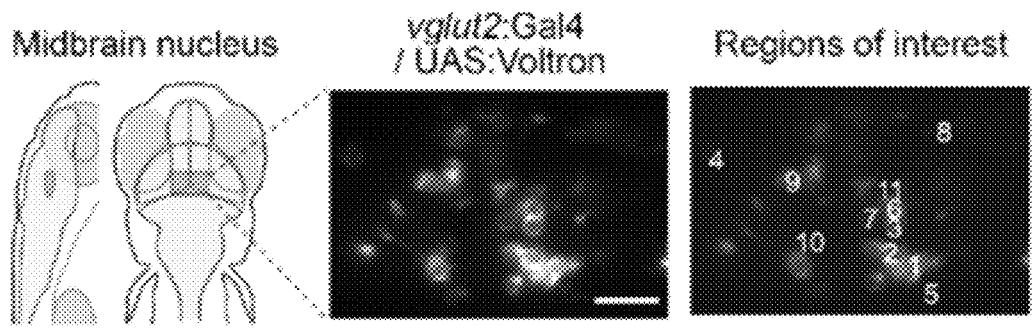
Figure 8C:
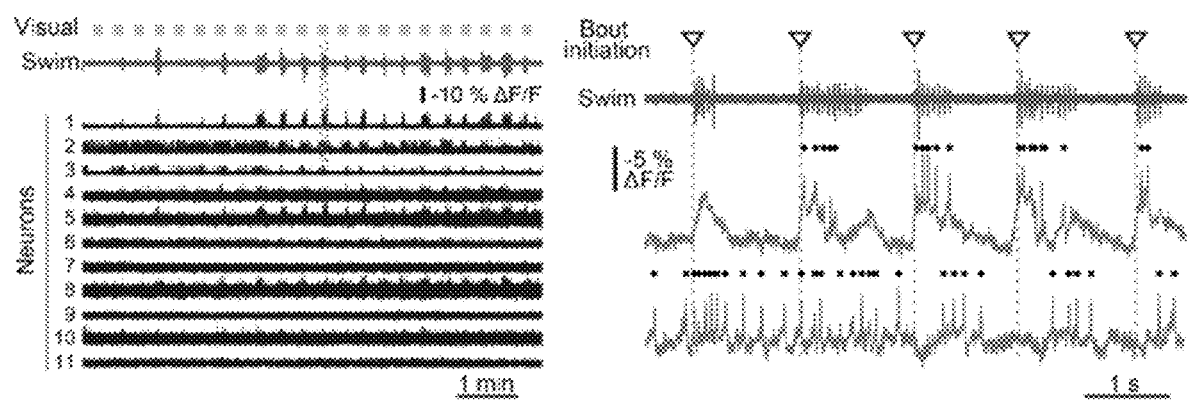
Figure 9A:
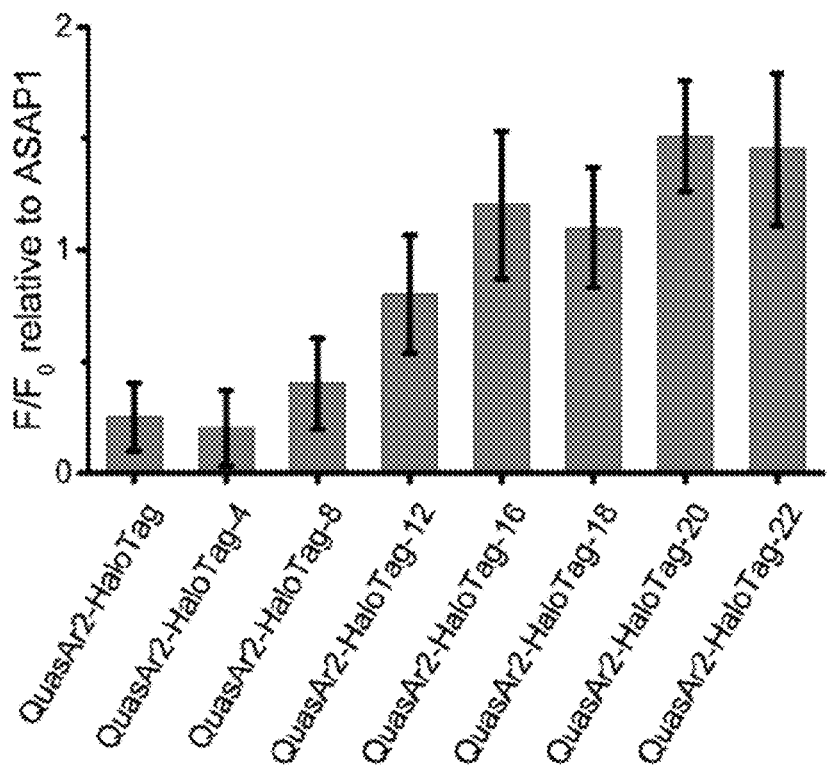
FIGS. 9A-9D includes a series of figures related to screening for a beneficial linker length between the rhodopsin and self-labeling tag domains. QuasAr2-HaloTag fusions (labeled with JF$_{549}$) and ASAP1 (32) were co-transfected into neurons and stimulated using a field stimulation electrode (see methods section). Truncating residues from the C-terminus of QuasAr2 and the N-terminus of HaloTag led to indicators with improved voltage sensitivity.
Figure 9B:
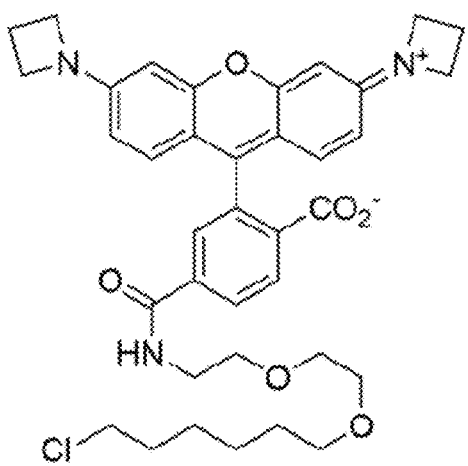
Figure 9C:
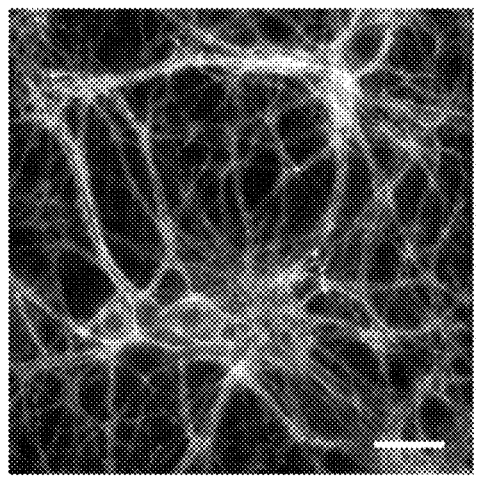
Figure 9D:
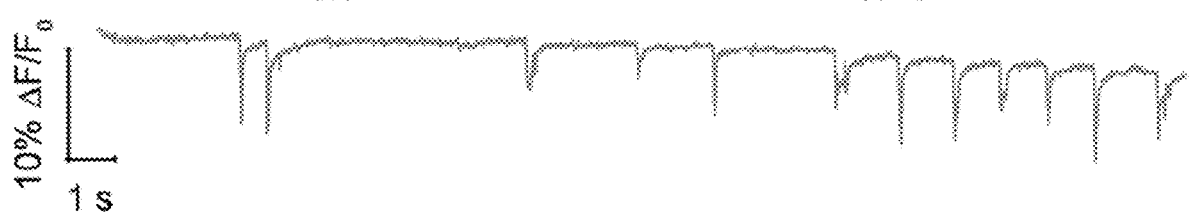
Figure 12:
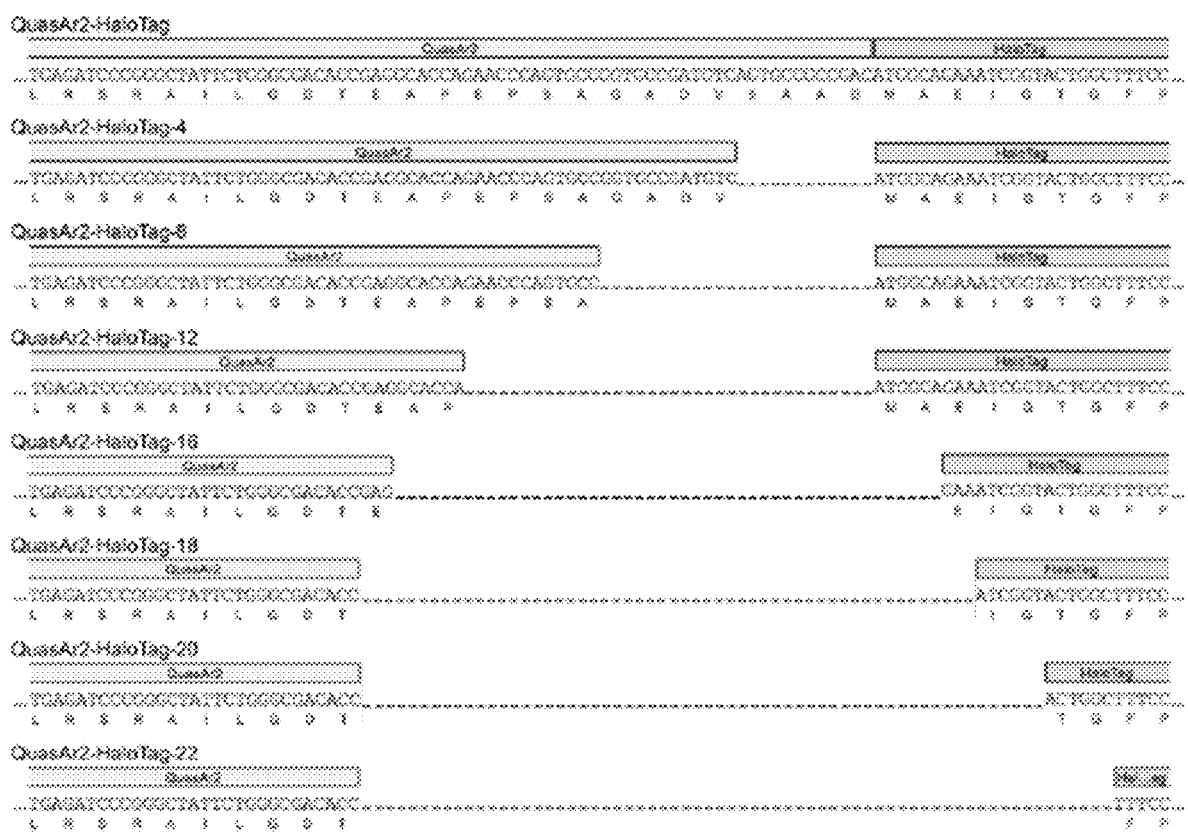
FIG. 12 includes the nucleotide sequence ((SEQ ID NOS: 25, 27, 29, 31, 33, 35, 37, 39) and amino acid sequence (SEQ ID NOS: 26, 28, 30, 32, 34, 36, 38, 40) of QuasAr2-HaloTag linker length truncations, with sequence features annotated.
Figure 14A:
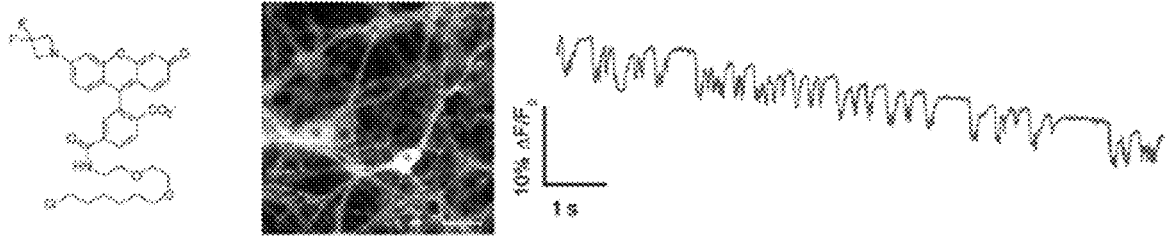
FIG. 14A includes Left: Chemical structure of JF505-HaloTag ligand, Middle: fluorescence image of hippocampal neurons in culture expressing QuasAr2-HaloTag-16 labeled with JF503. Right: Fluorescence trace over time showing voltage-dependent fluorescence changes resulting from spontaneous action potentials of the neurons.
Figure 14B:
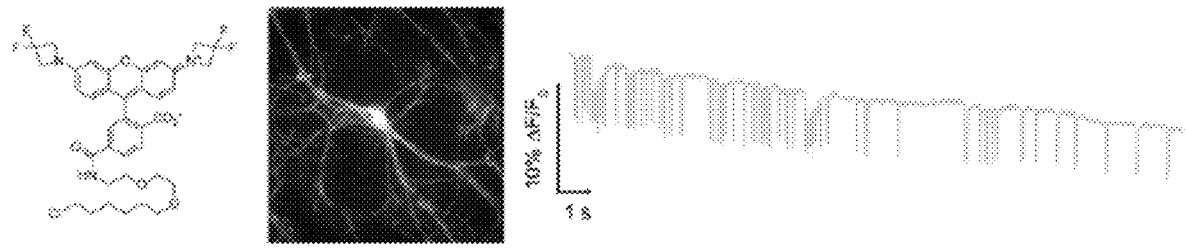
FIG. 14B includes (B) Left: Chemical structure of JF525-HaloTag ligand, Middle: fluorescence image of hippocampal neurons in culture expressing QuasAr2-HaloTag-16 labeled with JF525. Right: Fluorescence trace over time showing voltage-dependent fluorescence changes resulting from spontaneous action potentials of the neurons.
Figure 14C:
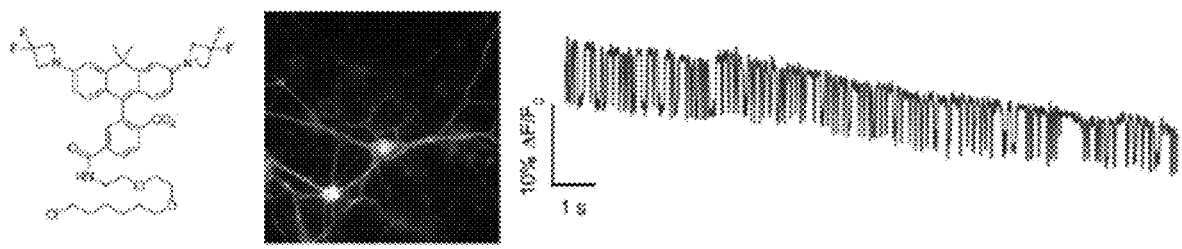
FIG. 14C includes, Left: Chemical structure of JF585-HaloTag ligand, Middle: fluorescence image of hippocampal neurons in culture expressing QuasAr2-HaloTag-16 labeled with JF585. Right: Fluorescence trace over time showing voltage-dependent fluorescence changes resulting from spontaneous action potentials of the neurons.
Figure 14D:
FIG. 14D includes, Left: Chemical structure of JF635-HaloTag ligand, Middle: fluorescence image of hippocampal neurons in culture expressing QuasAr2-HaloTag-16 labeled with JF635. Right: Fluorescence trace over time showing voltage-dependent fluorescence changes resulting from spontaneous action potentials of the neurons. Scale bar: 20 µm.
Figure 42A:
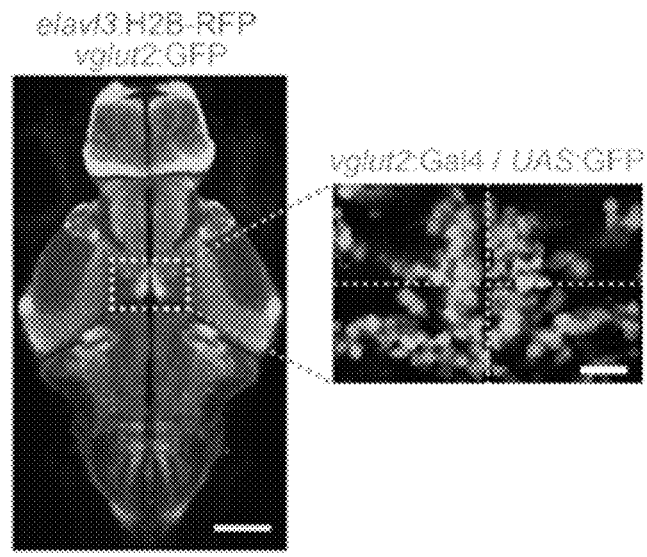
FIGS. 42A-42E relates to recording and analyzing Voltron data in behaving zebrafish.
Figure 42B:
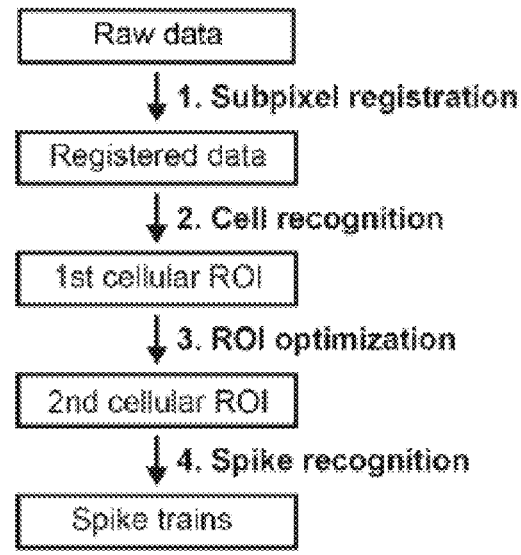
Figure 42C:
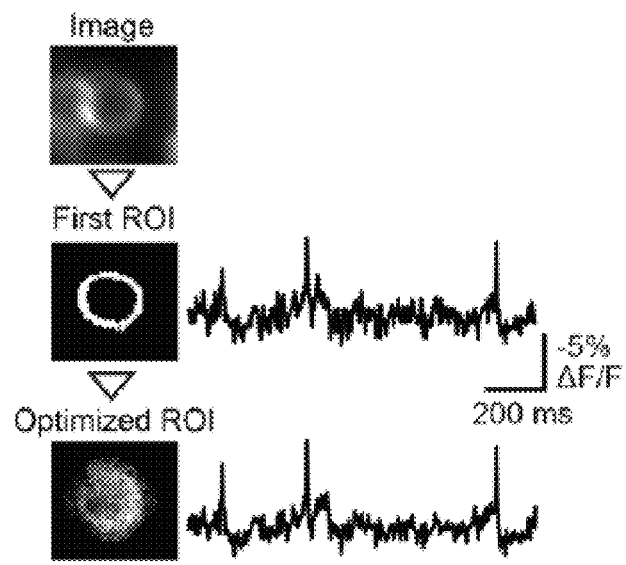
Figure 42D:
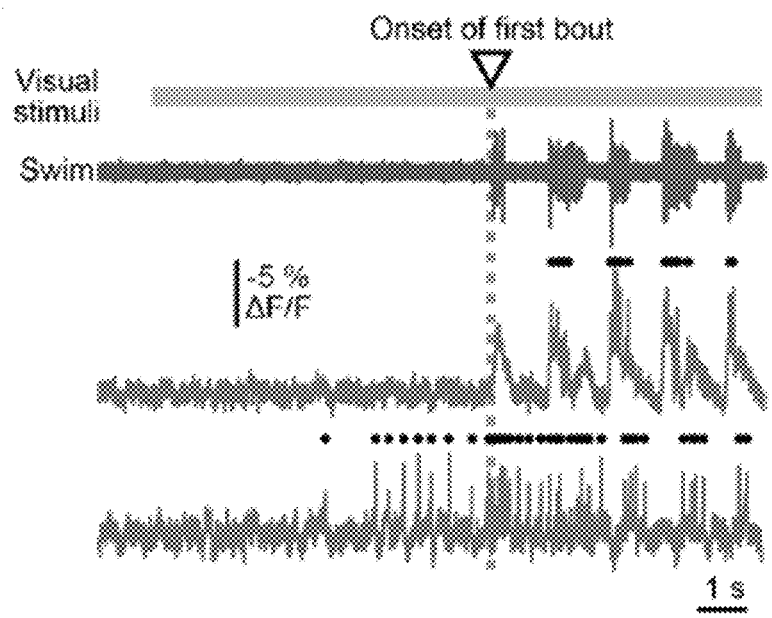

Voltron was then used to image behaving zebrafish larvae, which reliably respond to visual input with fast, directed swim bouts that are tailored to the details of the stimulus (26). Studies were conducted to determine how this sensory-to-motor transformation unfolds in neuronal populations at fine timescales that are inaccessible with calcium imaging. It was first verified that Voltron could detect action potentials and subthreshold voltage signals in live zebrafish using several different colors of dye ligands (FIGS. 21 and 4I). Voltron525 as then used to monitor neural spiking patterns during visual-motion-induced swims (FIG. 8A). Activity patterns from 179 neurons were recorded across 43 fish in a motor-sensory nucleus in the tegmental area of the midbrain (FIGS. 8B, 42A), yielding data on subthreshold membrane voltage modulation as well as automatically-detected spike times (FIGS. 8C, 42B-C). Neuron populations were found with different temporal activity patterns, including neurons whose firing rate increased ~1 second before the fish started swimming (FIG. 42D-E, 'Ramp'), neurons whose firing rate was suppressed each time the fish swam (FIG. 8D, 'Off'), and neurons that fired each time the fish swam (FIG. 8D, 'Onset' and 'Late'). Of the latter types, some fired just before swimming (~20 ms before swim onset, 'Onset') and others fired just after swimming (~10 ms after swim onset, 'Late'). There was a change in subthreshold voltage that preceded these firing-rate changes by tens of milliseconds (FIG. 8D). The neuron types were spatially intermingled within this midbrain nucleus (FIG. 8E-F). The existence of neurons that fired before swimming and neurons that fired after swimming suggests that this nucleus both partakes in the generation of swim bouts and receives an efference copy of motor output (FIG. 8G). Thus, Voltron allows for the dissection of population motor coding and sensorimotor integration circuits in ways that neither single-cell electrophysiology nor population calcium imaging can.

Figure 22A:
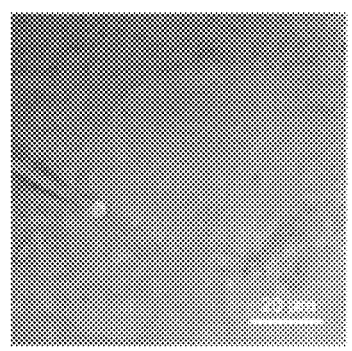
FIGS. 22A-22F relate to recording spontaneous dopamine neuron activity in living adult flies using Voltron imaging and whole-cell patch clamp.
Figure 22B:
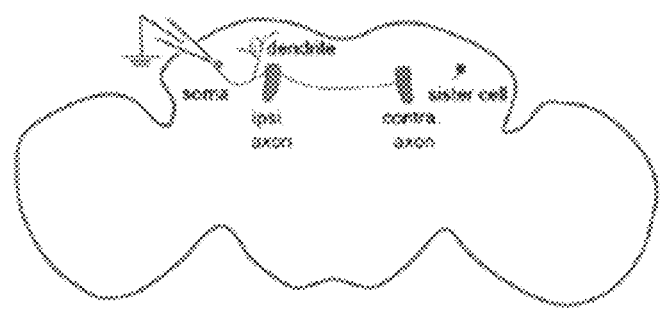
Figure 22C:
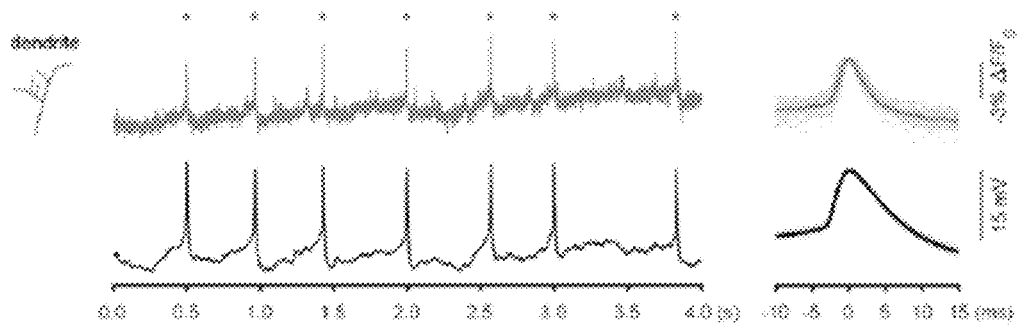
Figure 22D:
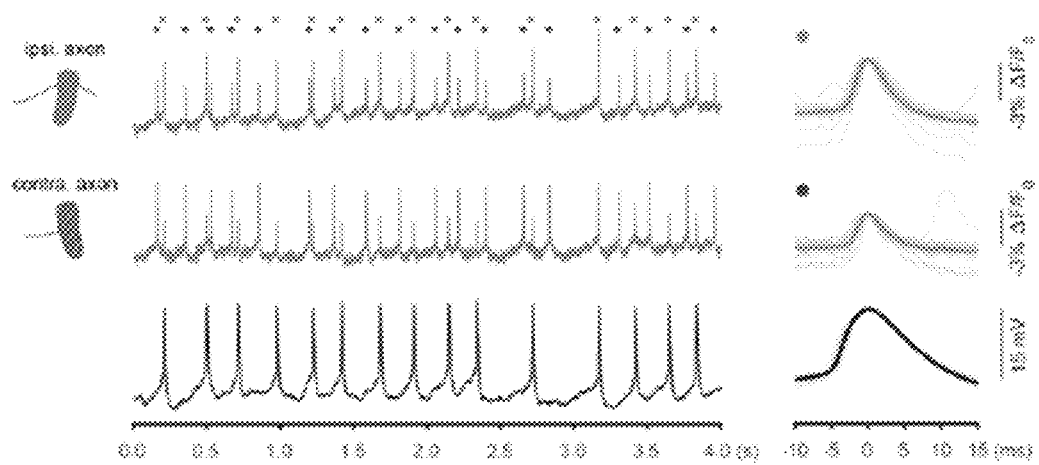
Figure 22E:
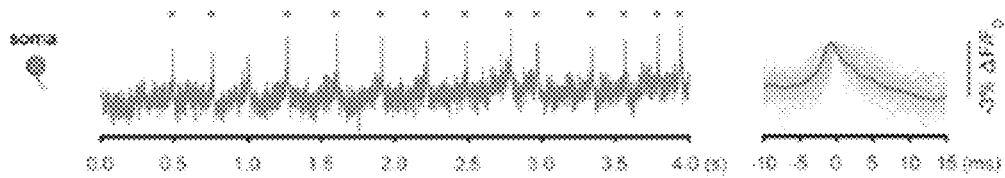
Figure 22F:
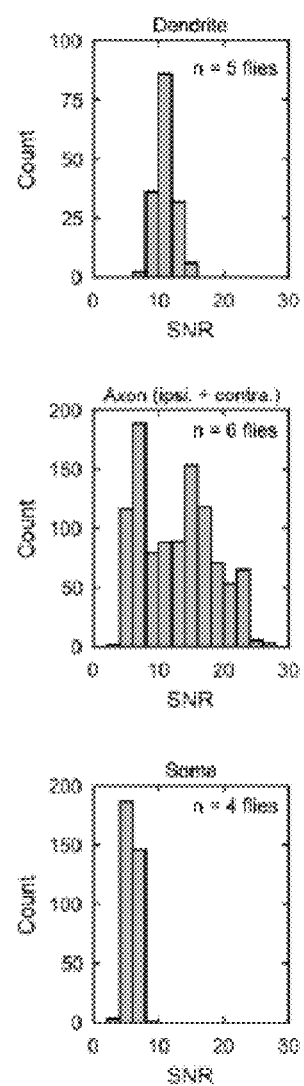
Figure 23:
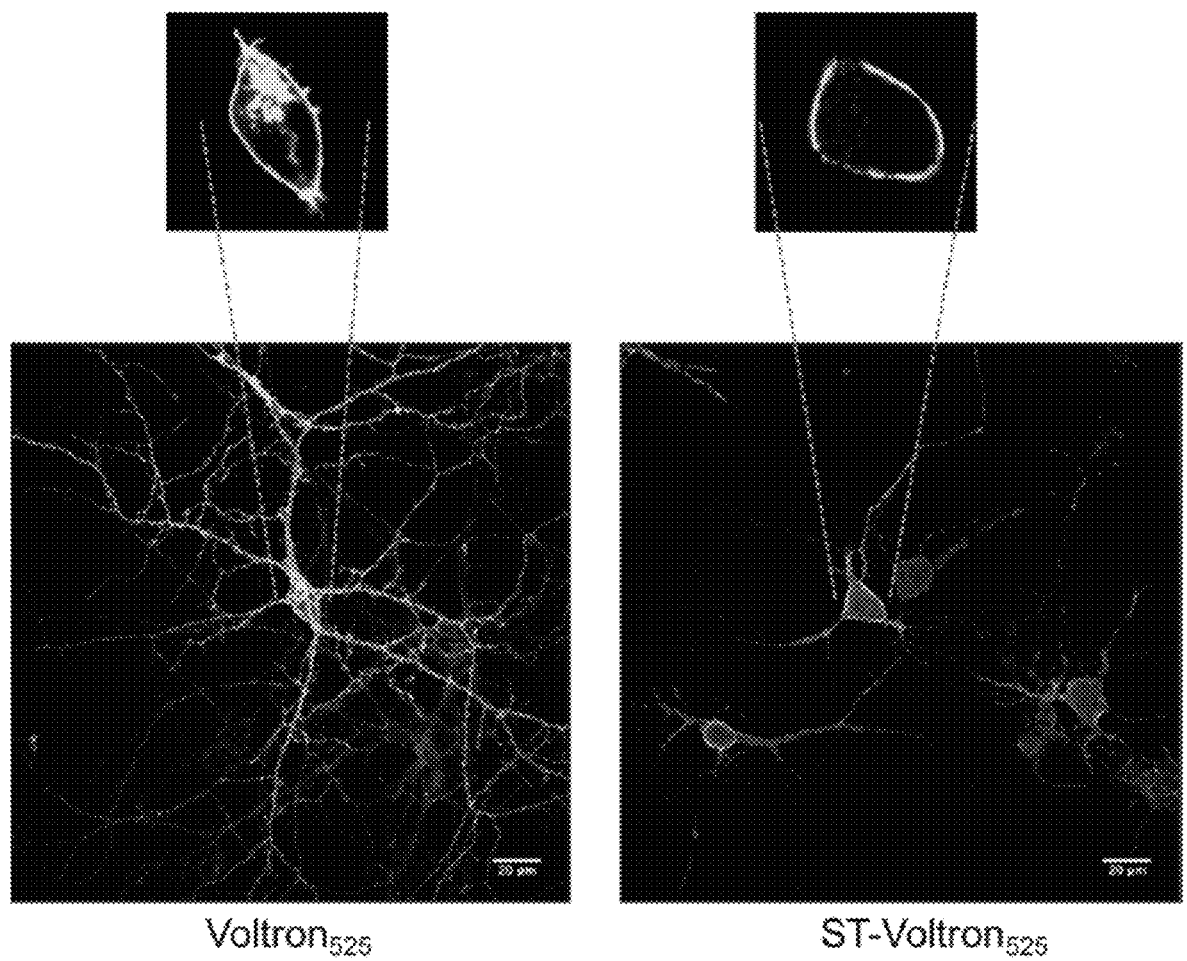
FIG. 23 includes maximum intensity projections of confocal stacks of neurons in culture (bottom panels) expressing Voltron (left) or soma-targeted Voltron (right) and labeled with $_{JF525}$. Zoom in on neuron soma showing cell membrane labeling and intracellular labelling, presumably endoplasmic reticulum (top panels). The soma localization tag limits labeling of processes and improves trafficking of Voltron to the cell membrane.

Finally, Voltron was tested in adult *Drosophila* in vivo by expressing the protein in a pair of dopaminergic neurons, one in each brain hemisphere, which innervate a single compartment in the mushroom body. Strong spiking signals were detected from axons and dendrites of these neurons using Voltron549 (FIGS. 5K, 22), which matched spikes detected using electrophysiology. In some neuronal cell types in *Drosophila*, calcium indicators located in the cell body have failed to exhibit fluorescence changes even under conditions where high spike rates are expected (27). However, spikes were clearly detectable when imaging from the soma of dopamine neurons with Voltron (FIG. 22E). Remarkably, spikes could be clearly distinguish from the two neurons based on the amplitude of the spiking signals even when imaging from neuropil where their axons overlap extensively, likely because each bilaterally-projecting cell contributes a denser innervation of the mushroom body in the ipsilateral hemisphere (FIG. 22D).

Combining the molecular specificity of genetically encoded reagents with the superior photophysics of chemical dyes is an established path to improved imaging reagents (14). However, previous attempts to create hybrid small-molecule:protein indicators using a variety of approaches have not been successful for in vivo imaging (28). Here, a modular sensor scaffold was engineered where the targeting and sensor domains are genetically encoded and only the fluorophore and its protein-binding anchor are synthetic. The resulting chemigenetic indicator, Voltron, exhibits substantially increased photon output, enabling in vivo voltage imaging of many more neurons over longer times—approximately $10^2$ more neuron-minutes than other sensors. This improvement enables imaging experiments that reveal how the precise electrical dynamics of neuronal populations orchestrate behavior over different time scales.

Example 3

Reagent availability: Voltron plasmids pCAG-Voltron (plasmid #), pCAG-Voltron-ST (plasmid #), pAAV-hsyn-Voltron (plasmid #), pAAV-hsyn-flex-Voltron (plasmid #), pAAV-hsyn-flex-Voltron-ST (plasmid #), pTol2-Huc-Voltron (plasmid #), pTol2-Huc-Voltron-ST (plasmid #), p10XUAS-IVS-Syn21-Voltron-p10 (plasmid #), and p13XLexAOP2-IVS-Syn21-Voltron-p10 (plasmid #) have been deposited at Addgene. AAV-hsyn-flex-Voltron-ST virus is available from Addgene (addgene.org).

Transgenic *Drosophila* stocks for UAS-Voltron and LexAop-Voltron in multiple landing sites are available from the Bloomington Drosophila Stock Center (flystocks.bio.indiana.edu).

UAS:Voltron transgenic zebrafish are available from the Ahrens Lab at Janelia Research Campus, and from ZIRC (zebrafish.org).

Cloning: Generally, cloning was done by restriction enzyme digest or PCR amplification of plasmid backbones, PCR amplification of inserted genes, and isothermal assembly to combine them, followed by Sanger sequencing to verify DNA sequences. The genes for QuasAr1 and QuasAr2 (7) were amplified from Addgene plasmids 51629 and 51692. The gene for Ace2N was synthesized (Integrated DNA Technologies) with mammalian codon optimization (11). The soma localization tag was synthesized (Integrated DNA technologies) through adding a 66 amino acid domain from the Kv2.1 potassium channel (residues 536 to 600) (22). This domain directs localization to clusters at the soma and proximal dendrites (23). Linker length variants were generated by Quikchange site-directed mutagenesis (Agilent). For expression in primary neuron cultures, sensors were cloned into a pcDNA3.1-CAG plasmid (Invitrogen) at the NheI and HindIII sites. For expression in zebrafish, Voltron and Voltron-ST were cloned into the pTol2-HuC vector (for pan-neuronal expression) at the AgeI restriction sites and into the pT2-Tbait-UAS vector (for Gal4-dependent expression) at the EcoRI and PspXI restriction sites. For expression in *Drosophila melanogaster*, Voltron was cloned into p10XUAS-IVS-Syn21-p10 at the XhoI and XbaI sites. For Cre-dependent expression in mouse brain, Voltron and Voltron-ST were cloned into a pAAV-hsyn-flex plasmid at the BamHI restriction sites. The DNA and amino acid sequences of Voltron and Voltron-ST are given in FIG. 8. Plasmids and maps are available from Addgene.

In vitro spectroscopy of fluorophores: To create JFdye-HaloTag conjugates, 5 μM JFdye HaloTag ligand and 10 μM HaloTag protein were incubated in 10 mM HEPES with 0.1 mg/ml CHAPS at pH 7.3 at 4° C. overnight. Completeness of dye-binding was determined by titrating HaloTag protein (2.5 μM to 12.5 μM) with fluorogenic$_{JF635}$ HaloTag ligand (5 μM) in overnight reactions and then measuring absorbance at 640 nm. Additionally, thin-layer chromatography was performed on a reaction of 5 μM $_{JF549}$ with 7.5 μM HaloTag, which showed >95% of the dye was bound to HaloTag. Fluorescent proteins sfGFP (parent fluorophore of ASAP2f) and mNeonGreen (parent fluorophore of Ace2N-mNeon) were purified from *E. coli*. All photophysical measurements used either 1 μM solutions of JFdye-HaloTag conjugate in 10 mM HEPES buffer at pH 7.3, or 1-3 μM purified fluorescent proteins in 100 mM MOPS buffer at pH 7.2. Absorbance measurements were performed on a UV-VIS spectrometer (Lambda 35, Perkin Elmer). Fluorescence excitation and emission spectra were measured using a fluorimeter (LS55, Perkin Elmer). Quantum yield measurements were performed using an integrating-sphere spectrometer (Quantaurus, Hamamatsu). Extinction coefficients for the JFdye-HaloTag conjugates were determined from peak absorbance at known concentration of JF dye. Extinction coefficients for fluorescent proteins were determined by the alkali denaturation method, using the extinction coefficient of denatured FP equal to that of denatured GFP (ε=44000 at 447 nm) (29).

Fluorescence microscopy for photobleaching: To investigate photobleaching of fluorophores in solution, aqueous droplets of JFdye-HaloTag conjugates or fluorescent proteins were made by aliquoting 5 µl of a fluorophore solution into 45 µl of 1-Octanol and agitating by tapping or brief vortexing. 5 µl of the emulsion mixture was sandwiched between a pre-silanized glass slide and a glass coverslip to disperse isolated microdroplets of dye-conjugates or proteins for fluorescence microscopy. To perform fluorescence microscopy, microdroplets were continuously illuminated using an inverted microscope (Eclipse Ti2, Nikon) with a 40× (N.A.=1.3, Nikon) oil immersion objective (PLAN Flour, Nikon). Fluorescence excitation was achieved using an LED (SpectraX Light engine, Lumencor) with the following filter sets for the respective fluorophores: For sfGFP, mNeonGreen and $_{JF505}$ (FITC5050A cube (semrock): FF02-475/50, FF506-Dio3, FF01-540/50); for $_{JF525}$ (510/25 excitation filter, T5251prx dichroic(Chroma), 545/40 emission filter); for $_{JF549}$ (Cy34040C cube (semrock): FF01-531/40, FF562-Dio3, FF01-593/40); for $_{JF585}$ (49912 cube (Chroma): ZET594/10x, ZT594rdc, ET6101p) and for $_{JF635}$ (89000 cube (Chroma), ET645/30x, 89100bs, ET705/72m). Power at the imaging plane for each filter set was set to 12 mW determined with a microscope slide power sensor (S170C, Thorlabs). From measurement of the sample area illuminated, the irradiance was determined to be 40 mW/mm². In order to calculate the excitation rate ! (photons absorbed/sec), the LED excitation spectrum was measured after the objective for each filter set using a fiber spectrometer (QE65000, Ocean Optics). Fluorescence images were collected using a scientific CMOS camera (ORCA-Flash 4.0, Hamamatsu) and image acquisition was performed using HCImage Live (Hamamtsu). Each sample was bleached continuously for 10 min. and images were acquired at 1 Hz. Fluorescence intensity from each droplet was obtained after background subtraction using ImageJ software.

To investigate photobleaching of GEVIs in cells, Voltron, Ace2N-mNeon, and ASAP2f were transfected in hippocampal neurons extracted from P0 to P1 Sprague-Dawley rat pups. After transfection, hippocampal neurons were plated onto 35 mm glass-bottom dish (MatTek) coated with poly-D-lysine (Sigma) and cultured for 8-10 days in NbActiv4 medium (BrainBits). For labeling Voltron-expressing neurons, cells were incubated with a 100 nM JFdye-HaloTag ligand for 30 minutes. The same setup and procedure used with droplets above was used to measure photobleaching of GEVIs in cells.

Photobleaching analysis: The bleaching profile of individual cells or droplets was fit to either a single or double exponential function of the form F(t)=F0 $(A_1 e^{-t/\tau_1} + A_2 e^{-t/\tau_2})$ to obtain time constants $\tau_1$, $\tau_2$ and weighting $A_1$, $A_2$. Data fitting was performed in MATLAB (MathWorks) and Origin (OriginLab), and goodness of fit assessed by minimal residual sum of errors or minimal $x^2$. To quantify photobleaching across fluorophores requires knowledge of the excitation rate W and the fluorescence quantum yield $\phi_f$. The excitation rate W was computed (30) from integration over the wavelength dependence of the product of measured extinction coefficient and irradiance spectral profile. The fluorescence quantum yield for the GEVIs is not directly measured, and assumed to be the same as that measured for the parent fluorophores. Three quantities characterizing bleaching were calculated for each fluorophore or GEVI. These are (i) the calculated time $t_{1/2}$ for the fluorescence rate to drop to ½ its initial value, scaled by the excitation rate to achieve an initial fluorescence rate of $10^3$ photons/sec (30), (ii) the total number of photons emitted before photobleaching $N_p$ (the photon budget), and (iii) the photobleaching probability $P_b$. These are per-molecule quantities averaged over the ensemble of molecules in each droplet or cell. The characteristic time $t_{1/2}$ was found by determining from the raw data, the time $t_{raw}$ for 50% reduction in fluorescence $F(t_{raw})/F_0=0.5$, from which $$t_{1/2} \equiv t_{raw} \frac{\phi_f W}{10^3 s^{-1}}$$

where $\phi_f$ is the fluorescence quantum yield and W is the excitation rate. To determine $N_p$, the fit function F(t) was integrated over time, where initially $F_0 = \phi_f W$, $$N_p = \phi_f W(A_1 \tau_1 + A_2 \tau_2) = \phi_f W \langle \tau_b \rangle$$

where $\langle \tau_b \rangle$ is the amplitude-weighted lifetime (31, 32) $\langle \tau_b \rangle = A_1 \tau_1 + A_2 \tau_2$. The photobleaching probability Pb, based on rate equation models where bleaching proceeds from singlet or triplet states, is inversely related to the total number of fluorescent photons emitted, $N_p = \phi_f / P_b$ (33, 34), or $$P_b = 1/W \langle \tau_b \rangle$$

Of the three photobleaching quantities above, the photobleaching probability is most rigorous as it is independent of the fluorescence quantum yield.

Single-Molecule Imaging and Analysis: Hippocampal neurons extracted from P0 to 1 Sprague-Dawley rat pups were transfected with Ace2N-mNeon and Voltron plasmids by electroporation (Lonza, P3 Primary Cell 4D-Nucleofector X kit) according to the manufacturer's instruction. After transfection, hippocampal neurons were plated onto 25 mm ultra-clean cover glasses coated with poly-D-lysine (Sigma) and cultured for 9 days in NbActiv4 medium (BrainBits).

To label Voltron-expressing neurons, cultures were incubated with 2 nM JF549 HaloTag ligand for 15 mins, then transferred to the Attofluor cell chamber (Thermo Fisher Scientific) and supplemented with Tyrode's solution (140 mM NaCl, 5 mM KCl, 3 mM $CaCl_2$, 1 mM $MgCl_2$, 10 mM HEPES, 10 mM glucose, pH 7.35). Single-molecule imaging was performed on a Nikon Eclipse TiE Motorized Inverted microscope equipped with a 100× oil-immersion objective lens (N.A.=1.49, Nikon), 488/561 nm laser lines, an automatic TIRF illuminator, a perfect focusing system and a Tokai Hit environmental control (humidity, 37° C., 5% $CO_2$). Excitation light was passed through a 405/488/561/647 nm laser quad band filter set filter that allows 488 nm or 561 nm light through to the sample (Chroma set number 89902). Emission from sample was collected through the same filter set then passed through a splitter (dichroic mirror: T560Ipxr (Chroma), with perpendicular emission filters: ET525/50m (Chroma) and ET605/52m (Chroma)) to split green and red fluorescence. The light was then collected onto two EMCCD cameras (iXon Ultra 897, Andor).

Samples were first pre-bleached to achieve sparse single molecule detections. The laser power output was calibrated for 488 nm (to image Ace2N-mNeon) and 561 nm (to image Voltron549) to 17.5 mW with a Si Sensor power meter (Thorlabs, PM202). Images were acquired under TIRF imaging mode with 10 Hz frame rate. 1000 frames were recorded for each imaging area and 10 imaging areas were collected for each indicator. For image analysis, single molecules lasting for at least 3 frames were manually selected. The brightness and mean time to photobleach of these molecules were determined with ImageJ (1.51n) quantification tools to assess the single-molecule photo-stability of Ace2N-mNeon and $Voltron_{549}$.

Fluorescence imaging in primary neuron culture: All culture imaging was performed in imaging buffer containing the following (in mM): 145 NaCl, 2.5 KCl, 10 glucose, 10 HEPES, pH 7.4, 2 CaCl$_2$, 1 MgCl$_2$. Wide-field imaging was performed on an inverted Nikon Eclipse Ti2 microscope equipped with a SPECTRA X light engine (Lumencore), 40× oil objective (NA=1.3, Nikon), and imaged onto a scientific CMOS camera (Hamamatsu ORCA-Flash 4.0). A FITC filter set (475/50 nm (excitation), 540/50 nm (emission), and a 506LP dichroic mirror (FITC-5050A-000; Semrock)) was used to image mNeonGreen, ASAP1, and ASAP2f. A Cy3 filter set (531/40 nm (excitation), 593/40 nm (emission), and a 562LP dichroic mirror (Cy3-4040C-000; Semrock)) was used to image Volton549. A custom filter set (510/25 nm (excitation), 545/40 nm (emission), and a 525LP dichroic mirror (Semrock)) was used to image Voltron525. A quad bandpass filter (set number: 89000, Chroma) was used along with the appropriate color band from the SPECTRA X light source to image Voltron505, Voltron585 and Voltron635. For time-lapse imaging during field stimulation or simultaneous electrophysiology measurements, neurons were imaged at 200-3200 Hz depending on the experiment. The LED light power output at the imaging plane was measured with a Si Sensor power meter (Thorlabs, PM202) for each imaging experiment.

For quantifying brightness of voltage indicators expressed in neurons, the excitation spectrum was measured after the objective for each excitation filter used using a spectrometer (QE65000, Ocean Optics). The spectrum was then integrated to get the excitation rate ! as described above (see section: Photobleaching analysis). As with the photobleaching experiments, when the data sets for the light spectrum and extinction coefficient are taken at incommensurate wavelengths, interpolation was used to re-cast the wavelengths of one of the data sets using MATLAB (MathWorks). The fraction of collected fluorescence using the emission filter compared to the total emission spectrum of the fluorophore was calculated. Illumination intensity of 20 mW/mm$^2$ at imaging plane was used for all indicators. Fluorescence images were acquired from five independent transfections for each construct for brightness measurements. Using MATLAB (MathWorks), fluorescence intensity was then corrected using the calculated excitation rates (!), fraction of emission collected, and quantum efficiency of the Hamamatsu ORCA-Flash 4.0 camera over the emitted wavelengths for ASAP2f, Ace2N-mNeon, Voltron525 and Voltron549. Values were calculated relative to ASAP2f.

Simultaneous field stimulation and fluorescence imaging in primary neuron cultures: A stimulus isolator (A385, World Precision Instruments) with platinum wires was used to deliver field stimuli (50V, 83 Hz, 1 ms) to elicit action potentials in cultured neurons as described previously (35). The stimulation was controlled using an Arduino board and timing was synchronized with fluorescence acquisition using the Nikon Elements software and a national instruments PXI-6723 board.

Simultaneous electrophysiology and fluorescence imaging in primary neuron culture: All imaging and electrophysiology measurements were performed in imaging buffer (see "Fluorescence imaging in primary neuron culture" section) adjusted to 310 mOsm with sucrose. For voltage clamp measurements, 500 nM TTX was added to the imaging buffer to block sodium channels. Synaptic blockers (10 µM CNQX, 10 µM CPP, 10 µM GABAZINE, and 1 mM MCPG) were added to block ionotropic glutamate, GABA, and metabotropic glutamate receptors (35).

Filamented glass micropipettes (Sutter Instruments) were pulled to a tip resistance of 4-6 MΩ. Internal solution for current clamp recordings contained the following (in mM): 130 potassium methanesulfonate,10 HEPES, 5 NaCl, 1 MgCl$_2$, 1 Mg-ATP, 0.4 Na-GTP, 14 Tris-phosphocreatine, adjusted to pH 7.3 with KOH, and adjusted to 300 mOsm with sucrose. Internal solution for voltage clamp recordings contained the following (in mM): 115 cesium methanesulfonate, 10 HEPES, 5 NaF, 10 EGTA, 15 CsCl, 3.5 Mg-ATP, 3 QX-314, adjusted to pH 7.3 with CsOH, and adjusted to 300 mOsm with sucrose.

Pipettes were positioned with a MPC200 manipulator (Sutter Instruments). Whole cell voltage clamp and current clamp recordings were acquired using an EPC800 amplifier (HEKA), filtered at 10 kHz with the internal Bessel filter, and digitized using a National Instruments PCIe-6353 acquisition board at 20 kHz. Data were acquired from cells with access resistance <25 MΩ. WaveSurfer software was used to generate the various analog and digital waveforms to control the amplifier, camera, light source, and record voltage and current traces. For fluorescence voltage curves, cells were held at a potential of −70 mV at the start of each step and then 1 second voltage steps were applied to step the potential from −110 mV to +50 mV in 20 mV increments. For current-clamp recordings to generate action potentials, current was injected (20-200 pA for 1-2 s) and voltage was monitored.

Imaging Parvalbumin (PV) neurons in mouse hippocampus: Hippocampal PV neuron imaging was performed using adult PV-Cre mice (JAX 008069). Imaging window was implanted using procedures similar to those described in Dombeck et. al. (36). In short, a circular craniotomy (3 mm diameter) was made centered at 2.0 mm caudal and 2.0 mm lateral to bregma. The surface of CA1 was exposed by gently removing the overlying cortex with aspiration. AAV2/1-syn-Flex-Voltron-ST virus was diluted to 1.9×10$^{12}$ GC/ml and injected at three locations (separated by 800 µm, 30 nl per location) 200 µm from CA1 surface. The imaging window (constructed by gluing a 3 mm diameter cover glass to a stainless steel cannula of 3 mm diameter and 1.5 mm height) was placed onto the hippocampus and glued to the skull using super-bond C&B (Sun Medical). A titanium head bar was glued to the skull for head fixation during imaging.

Imaging experiments started 4-5 weeks after surgery. JF525-HaloTag ligand (100 µl, 1 mM) was delivered using retro-orbital injection (37) 1 day before imaging. Labeled PV neurons (25-195 µm deep) were illuminated using a green LED (M530L3, Thorlabs) through an excitation filter (FF02-520-28, Semrock). A field aperture (diameter ~1 mm) was used to limit illumination to a circular area (~160 µm diameter at sample) around the cell of interest. The excitation intensity was ~25 mW/mm$^2$ at the sample plane. JF525 fluorescence was collected using a 16×0.8 NA objective (Nikon), separated from excitation light using a dichroic mirror (5401pxr, Chroma) and an emission filter (FF01-575-59, Semrock), and imaged onto a sCMOS camera (Zyla 4.2 plus, Andor). Images were collected at 3858 Hz.

Figure 24:
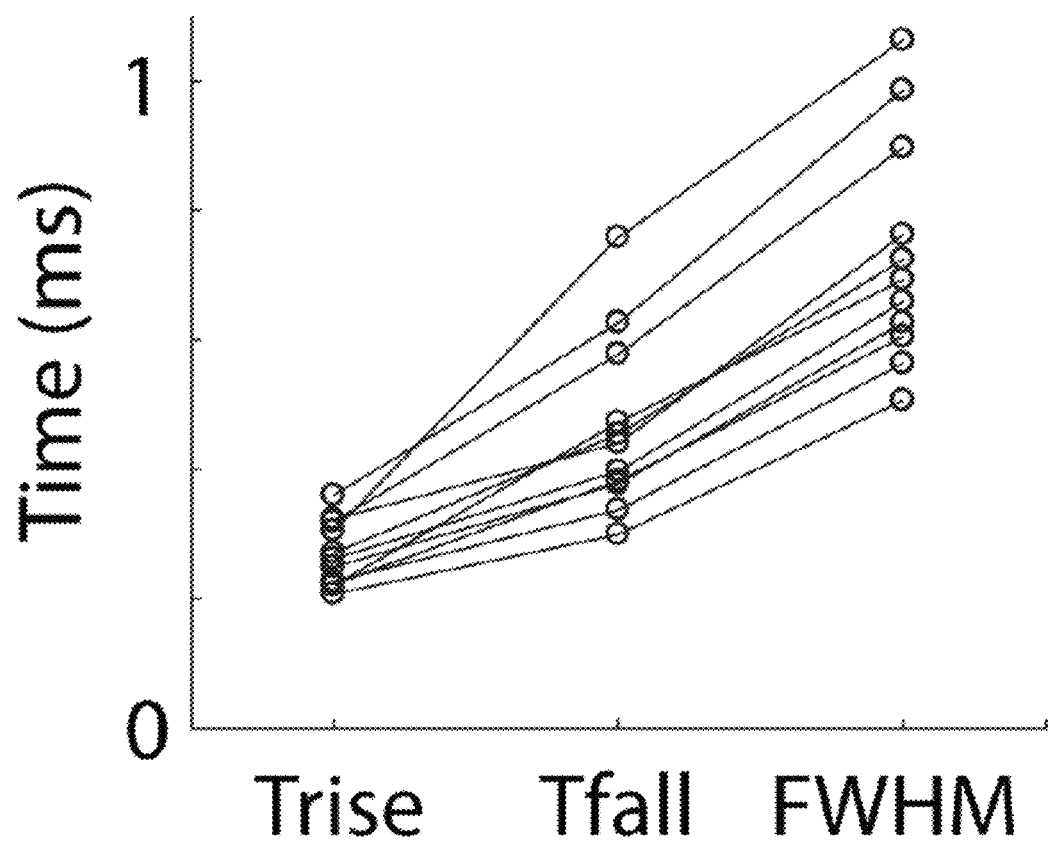
FIG. 24 include an analysis of membrane voltage dynamics in hippocampal parvalbumin (PV) neurons of awake mouse. The half rise time, half decay time, and full width half maximum of the spike waveforms shown in FIG. 6G.
Figure 25:
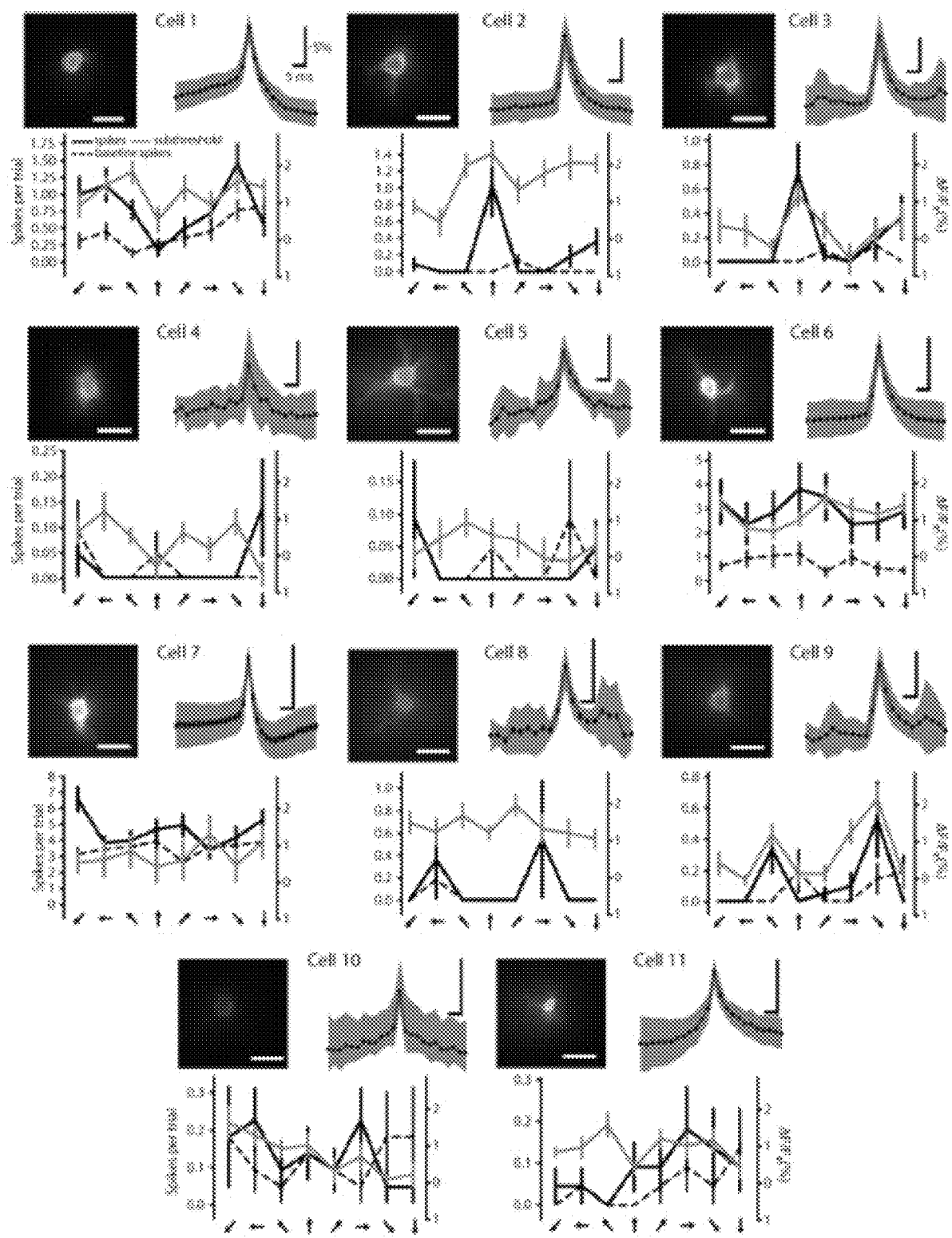
FIG. 25 includes results of orientation tuning of 11 pyramidal cells at depths of 100-250 μm in visual cortex of two C57B6 mice expressing Voltron525 under the control of CamKII-Cre. Each of the 11 cell panels includes fluorescence image of cell (top left, scalebar: 20 μm), average of all spikes in session (top right, scalebars: −5% AF/F, 5 ms) and orientation tuning to full-frame drifting gratings of neurons (bottom), displayed from number of spikes during trials (solid black line), number of spikes during preceding inter-trial intervals (dashed black line), and subthreshold AF/F0 (right y-axis, solid gray line) after low-pass filtering traces using a 10-point median filter.
Figure 26A:
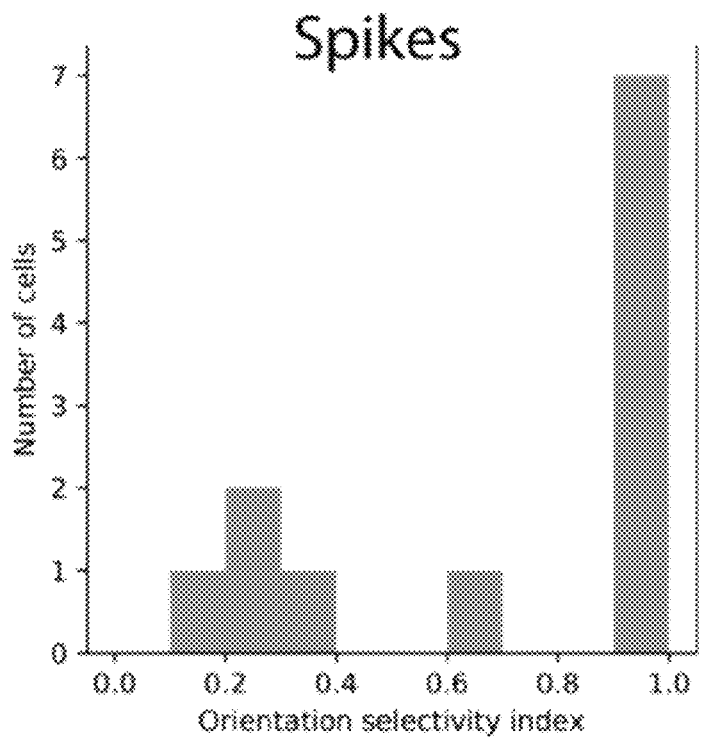
FIG. 26A includes a histogram of orientation selectivity index calculated from number of spikes in trial.
Figure 26B:
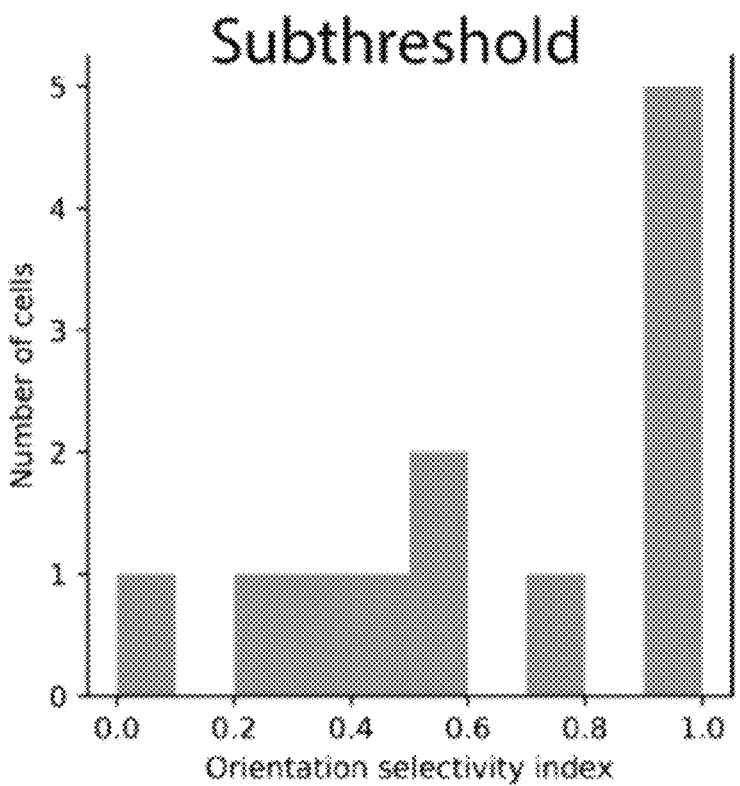
FIG. 26B includes a histogram of orientation selectivity index calculated from subthreshold membrane potential.

Image analysis was performed in MATLAB. Brain movement was corrected using ImageJ plugin TurboReg (38). A constant camera offset (measured by taking images without illumination) was subtracted from each frame. The fluorescence of each cell was measured by averaging pixels within a region of interest covering the cell body. To detect action potentials (AP), slow baseline fluctuation (measured by moving average with 20 ms window) was first subtracted from the raw fluorescence trace. The timings of AP events were detected as local minima of the baseline subtracted trace with amplitudes larger than four times the standard deviation and peaks separated by at least 5 ms from each other. To quantify AP waveform, 5 ms segments of fluorescence signal around the detected peaks were taken from the raw fluorescence trace, peak aligned and then averaged. The AP amplitude was measured as percent change (F−F0)/F0 with F0 being the fluorescence baseline averaged over a time window 2.5 ms to 1.5 ms before the peak of an individual AP. The rise time, decay time, and the width of the AP waveform was measured using the averaged trace for each cell. The rise time was the time from half the amplitude to the peak. The decay time was the time from the peak to half the amplitude in the decay phase. The width (full width at half maxima, FWHM) was the sum of rise and decay time. This is shown in FIG. 24.

Imaging mouse cortex: NDNF-Cre mice (JAX 28536) were used for imaging Layer 1 neurons (2 females, 1 male; 100 -120 days old at the time of the window surgery). C57BI/6NCrl (Charles River Laboratories) mice were used for imaging Layer 2/3 neurons (2 females; 100-120 days old). NDNF-Cre mice were injected with 30 nl of AAV2/1-syn-FLEX-Voltron-ST (titer, $2*10^{12}$ GC/ml) at 8-12 injection sites 200 µm deep (injection rate, 1 nl/s). C57BI/6NCrl mice were injected with 30 nl mixture of AAV2/1-syn-FLEX-Voltron-ST (titer, $2*10^{12}$ GC/ml) and AAV9-CamKIIa-Cre (titer, $10^8$ GC/ml) 250 µm deep. AAV2/1-syn-FLEX-Voltron without soma targeting signal was injected in additional NDNF-Cre mice (titer, $2*1012$ GC/ml)) and C57BI/6NCrl mice (AAV2/1-syn-FLEX-Voltron (titer, $2*10^{12}$ gc/ml)+AAV9-CamKIIa-Cre (titer, $10^8$ gc/ml)). This resulted in diffuse fluorescence and was not used for imaging experiments shown in this manuscript.

Cranial windows (4 mm diameter) were implanted over the injection sites in visual cortex (centered on −2.5 mm lateral, +0.5 mm anterior from lambda). Four to nine weeks later JF525 dye was injected into the retro-orbital sinus. Imaging was done 2 to 6 days after dye injection, with subsequent dye injections and imaging 1 to 6 weeks after the first imaging session. To prepare the JF dye for injection, 100 nanomoles of lyophilized $JF_{525}$ were dissolved in 20 µl of DMSO, 20 µl Pluronic F-127 (20% w/v in DMSO), and 60-80 µl of PBS (final dye concentration 1 µM). Mice were anesthetized with 2-3% isoflurane and 100 µl of the dye solution was injected into the retro-orbital sinus of the right eye using a 27-30 gauge needle (37).

For imaging experiments of Layer 1 neurons, a wide-field fluorescence microscope equipped with a water immersion objective (20×, NA 1.0, Olympus XLUMPLFLN) was used for imaging. Illumination was delivered using a 525 nm LED (Mightex, LCS-0525-60-22); intensity at the sample, <20 mW/mm². An mKO/mOrange filter set (530/30 nm (excitation), 575/40 nm (emission), and a 550LP dichroic mirror (Chroma, 49014)) was used for fluorescence imaging of Voltron525. Images were collected using a sCMOS camera (Hamamatsu Orca Flash 4.0 v3) at frame rates of 400-1000 Hz. A 0.55× magnification camera tube was placed between the objective and the camera for imaging large fields of view of 1064 µm×266 µm (FIG. 7F-7G and FIG. 27-40). The pixel resolution was 2.08 µm/pixel. For smaller fields of view (FIG. 7B-7E and FIG. 25) a 1× camera tube was used. The pixel size was 1.04 µm. Mice were awake and imaged in darkness.

To image Layer 2/3 pyramidal cells, the following changes were made from the imaging protocol for Layer 1 interneurons: Images were recorded at frame rate of 500-700 Hz. Illumination intensity at the sample was <50 mW/mm². 1× camera tube was used and the field of view imaged was typically 50 µm×50 µm. The pixel size was 1.04 µm. A digital mirror device (Texas Instruments, LightCrafter) restricted the illumination to the cell being imaged. Mice were imaged while lightly anesthetized and passively viewing drifting gratings (described below).

Visual stimulation for pyramidal cell recordings: Mice were presented with drifting grating visual stimuli during imaging sessions (spatial frequency: 0.03 cycles/degree, temporal frequency: 1 Hz, trial period: 1 s, and inter-trial interval: 1 s). Gratings were shown in blue with a black background. During the inter-trial interval, the screen was black. Eight orientations separated by 45° were presented. Mice were anesthetized during all sessions. To induce anesthesia, chlorprothixene (0.2 mg/ml, 5 ul/g weight mouse) was injected into the hind paw followed by keeping the mouse in a chamber with 2-3% isoflurane for 1-2 minutes. Anesthesia was maintained at 0.4-0.8% isoflurane for the duration of the imaging session. Mice were kept on a heating blanket at a temperature of 37°.

Analysis of Layer 2/3 pyramidal cell imaging: Motion was removed using a rigid registration algorithm. A constant camera offset was subtracted from each frame. A region of interest (ROI) was manually drawn around the neuron. The initial trace (X0) is the mean intensity over the ROI in time. X0 was fit with a piecewise linear curve using a Savitzky-Golay filter with a window size of 10 s to estimate the slow baseline fluctuations, F0. ΔF/F was calculated as $$\frac{X0 - F0}{F0}.$$

Spike times were manually selected as large amplitude local minima in the ΔF/F trace occurring in periods of depolarization and separated from other local minima by at least 2 ms.

Visual responses (FIG. 6H-6L and FIG. 25) were calculated as the average number of spikes during the trial for each orientation, averaged over repetitions. To estimate the subthreshold fluctuations, the ΔF/F trace was low-pass filtered at 50 Hz using a median filter. The response for each orientation was calculated as the average of the low-pass filtered trace from 100 ms to 400 ms after the trial start. The baseline was calculated as the average of the low-pass filtered trace from 80 ms before trial start to 20 ms after the trial start. The baseline was subtracted from the response for each trial and averaged over 20 repetitions.

The orientation selectivity index (FIG. 26) was calculated as:

$$(R_{pref} - R_{orth})/([R_{pref}] + [R_{orth}])$$

where $R_{pref}$ is the response (mean spikes in trial or mean subthreshold membrane potential) to the preferred orientation, and $R_{orth}$ is the response to the orientation 90° away from the preferred orientation.

Analysis of Layer 1 interneuron imaging: To identify neuronal activity and spatial structure from Voltron recordings, an iterative spatial and temporal filtering approach was designed and called: Spike Pursuit. In essence, Spike Pursuit begins with a poorly estimated voltage trace for a neuron, and uses detected spikes to iteratively estimate improved temporal and spatial filters that increase the signal to noise ratio of the spikes while controlling for overfitting. Spike pursuit relies on linear methods (the whitened matched filter for temporal filtering, and regularized linear regression for spatial filtering) (39).

Figure 29:
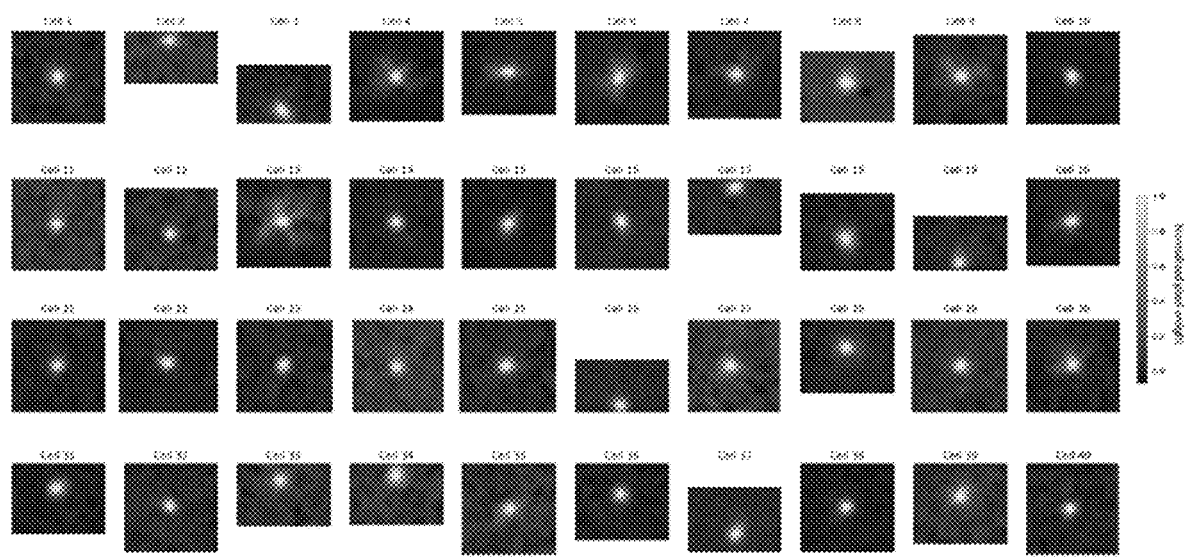
FIG. 29 includes a series of spatial filters for context regions of 50×50 pixels centered on the ROI of each cell shown in FIG. 7F-7G and FIG. 27A-27C. Spatial filters were estimated by Spike Pursuit. Cells near the boundary of the field of view have different sizes of context region.
Figure 30A:
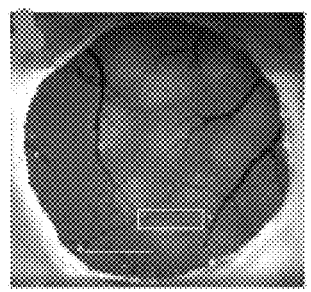
FIG. 30A includes a fluorescence image of a cranial window over primary visual cortex (V1) in an NDNF-Cre mouse showing Cre-dependent expression of soma targeted Voltron525. Scalebar, 1 mm.
Figure 30B:
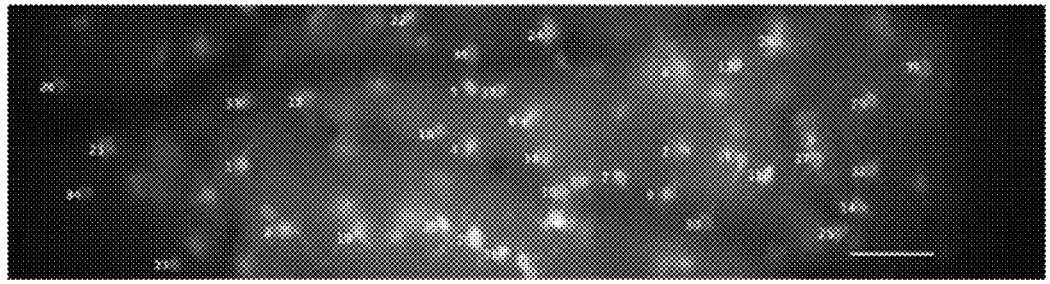
FIG. 30B includes a fluorescence image of area indicated by the white rectangle in FIG. 30A, with neuron labels corresponding to fluorescence traces in FIG. 30C. Scalebar, 100 μm.
Figure 30C:
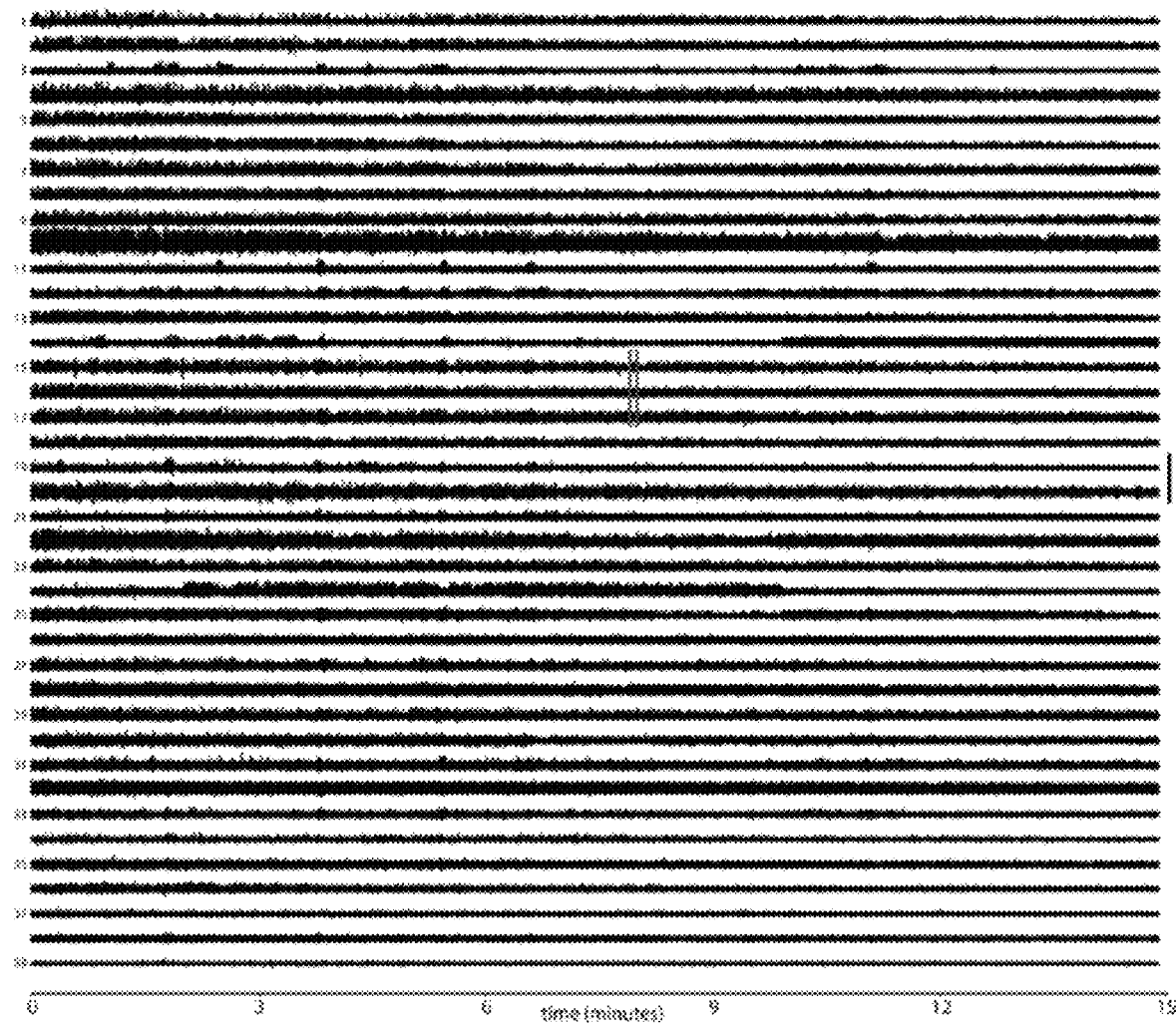
FIG. 30C: Fluorescence traces during 10-15 minutes recordings from neurons indicated in FIG. 30B, in decreasing order of signal to noise ratio.
Figure 30D:
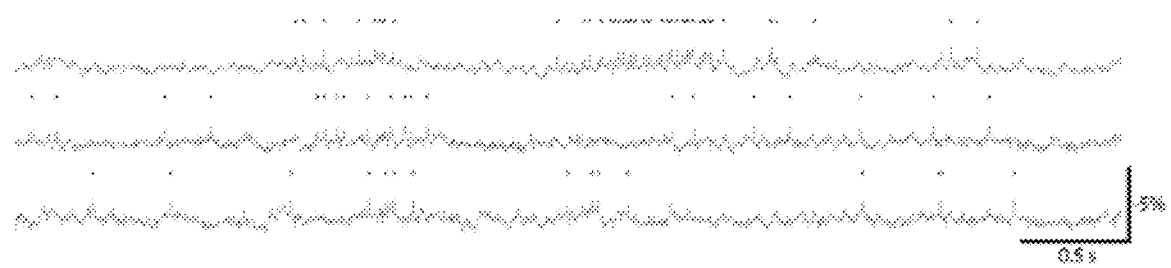
FIG. 30D includes zoom-in of fluorescence traces from area indicated by red rectangle in FIG. 30C.
Figure 31A:
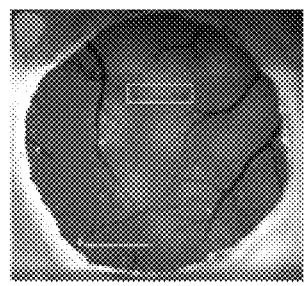
FIG. 31A includes a fluorescence image of a cranial window over primary visual cortex (V1) in an NDNF-Cre mouse showing Cre-dependent expression of soma targeted Voltron525. Scalebar, 1 mm.
Figure 31B:
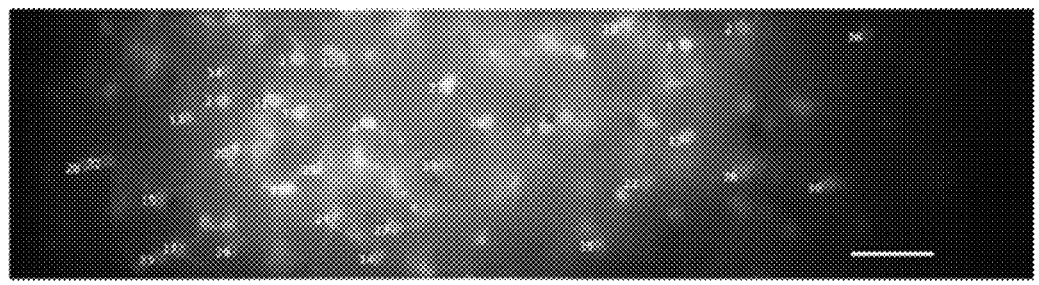
FIG. 31B includes a fluorescence image of area indicated by the white rectangle in FIG. 31A, with neuron labels corresponding to fluorescence traces in FIG. 31C. Scalebar, 100 μm.
Figure 31C:
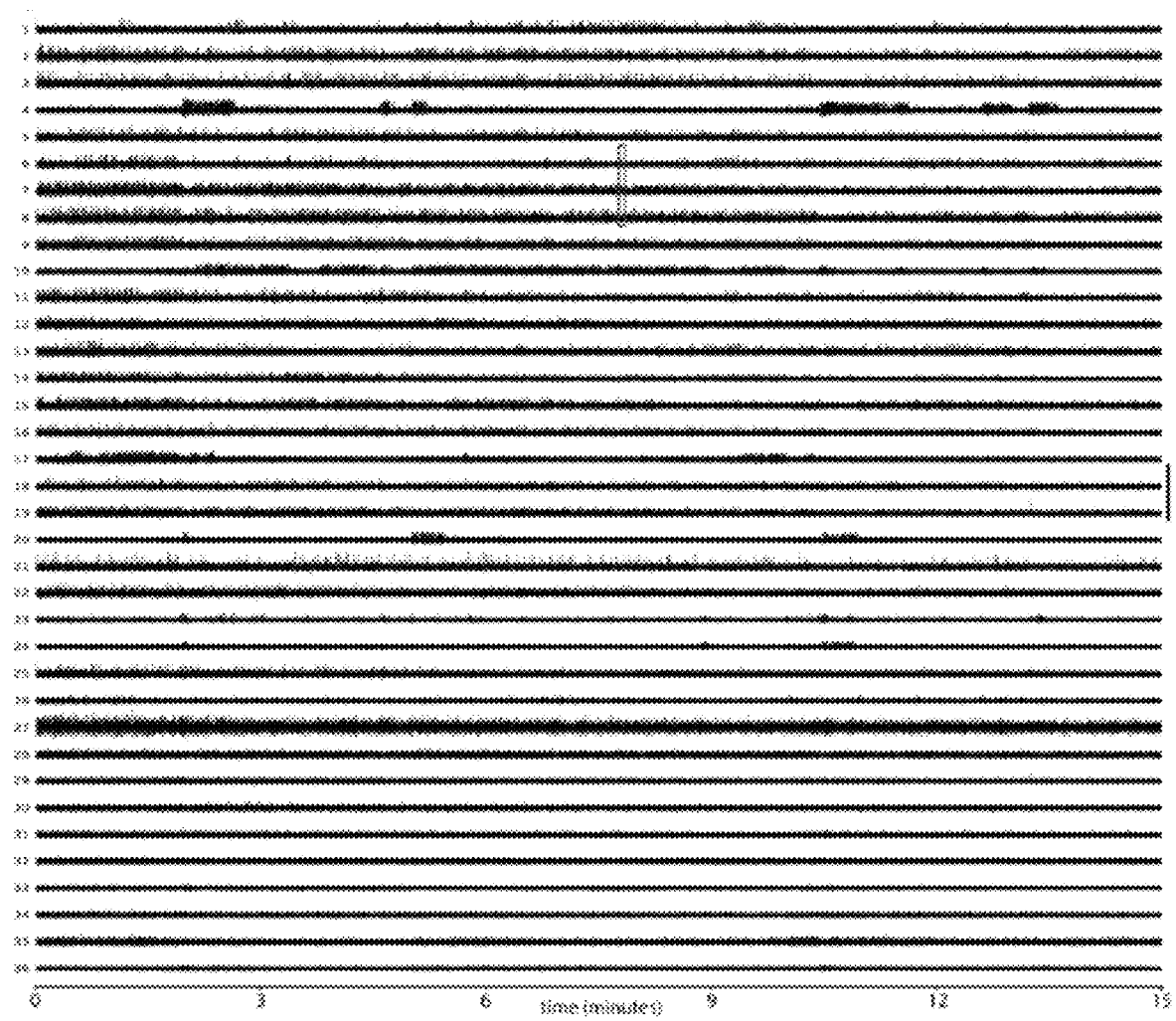
FIG. 31C includes fluorescence traces during 10-15 minutes recordings from neurons indicated in FIG. 31B, in decreasing order of signal to noise ratio.
Figure 31D:
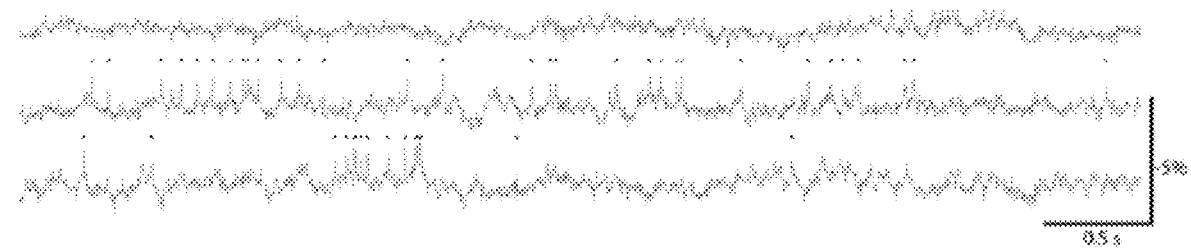
FIG. 31D includes zoom-in of fluorescence traces from area indicated by red rectangle in FIG. 31C.
Figure 32A:
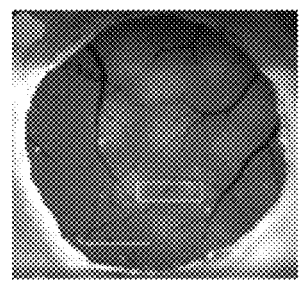
FIG. 32A includes fluorescence image of a cranial window over primary visual cortex (V1) in an NDNF-Cre mouse showing Cre-dependent expression of soma targeted Voltron525. Scalebar, 1 mm.
Figure 32B:
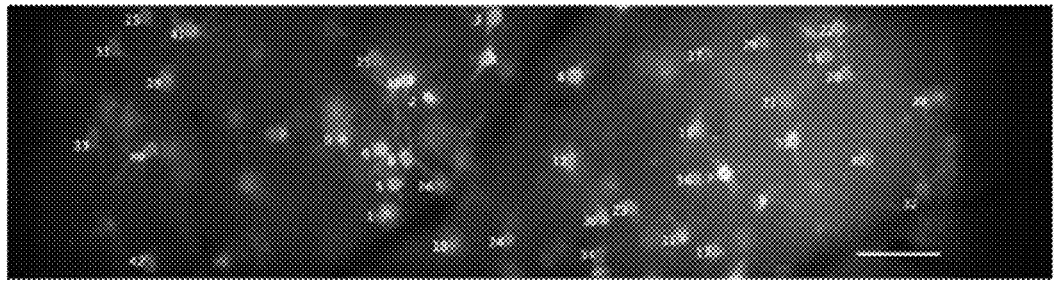
FIG. 32B includes fluorescence image of area indicated by the white rectangle in FIG. 32A, with neuron labels corresponding to fluorescence traces in FIG. 32C. Scalebar, 100 μm.
Figure 32C:
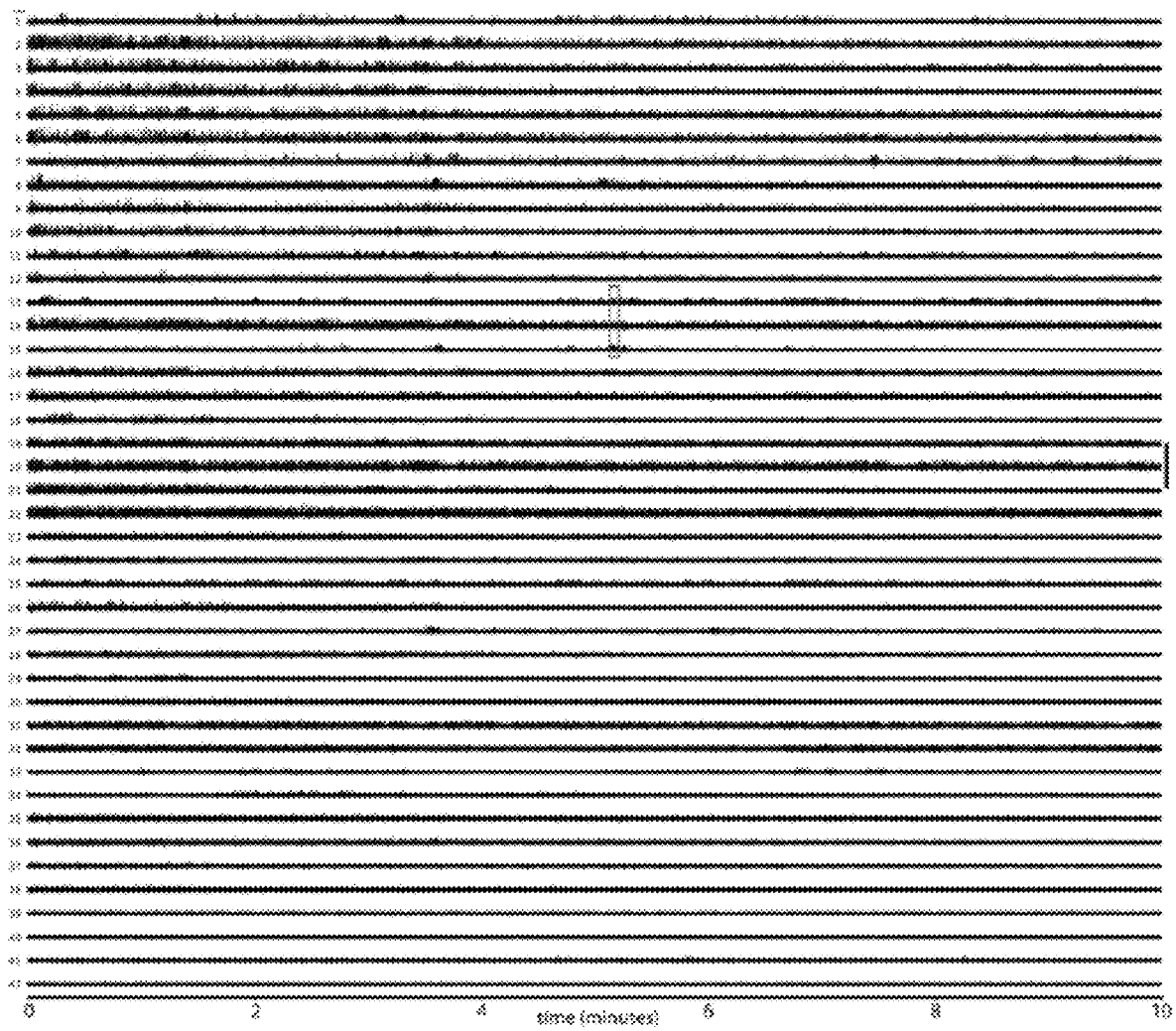
FIG. 32C Fluorescence traces during 10-15 minutes recordings from neurons indicated in FIG. 32B, in decreasing order of signal to noise ratio.
Figure 32D:
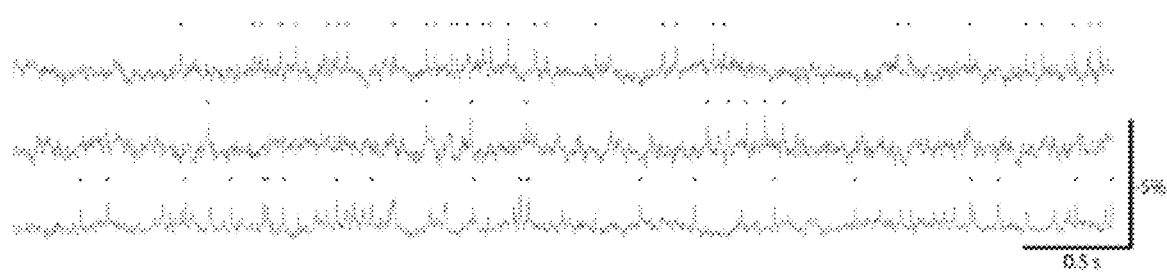
FIG. 32D includes zoom-in of fluorescence traces from area indicated by red rectangle in FIG. 32C.
Figure 33A:
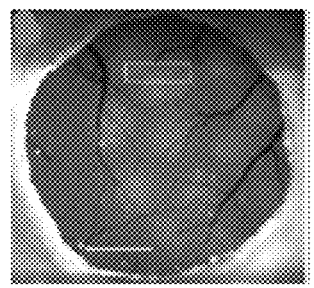
FIG. 33A includes fluorescence image of a cranial window over primary visual cortex (V1) in an NDNF-Cre mouse showing Cre-dependent expression of soma targeted Voltron525. Scalebar, 1 mm.
Figure 33B:
FIG. 33B includes fluorescence image of area indicated by the white rectangle in FIG. 33A, with neuron labels corresponding to fluorescence traces in FIG. 33C. Scalebar, 100 μm.
Figure 33C:
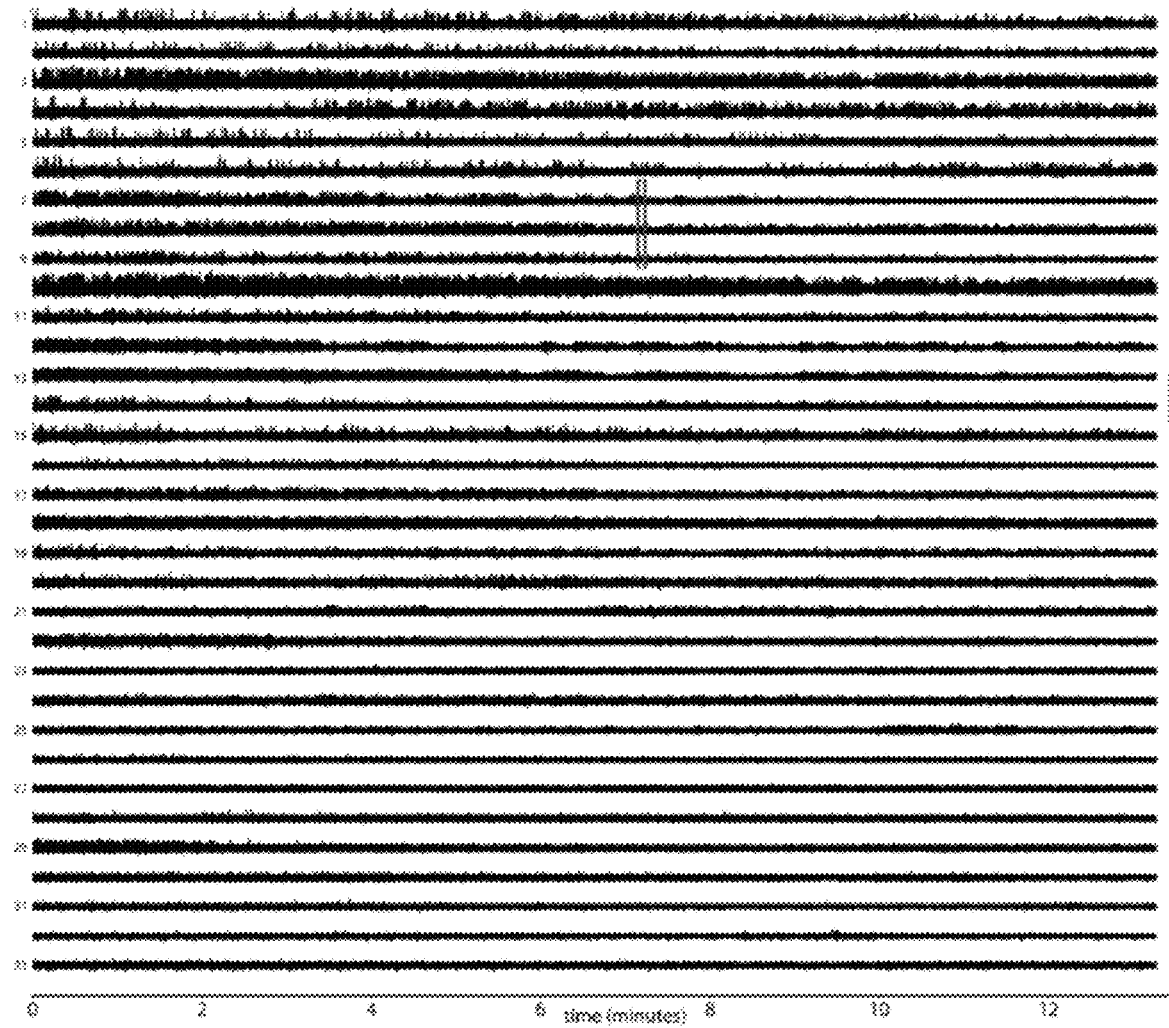
FIG. 33C includes fluorescence traces during 10-15 minutes recordings from neurons indicated in FIG. 33B, in decreasing order of signal to noise ratio.
Figure 33D:
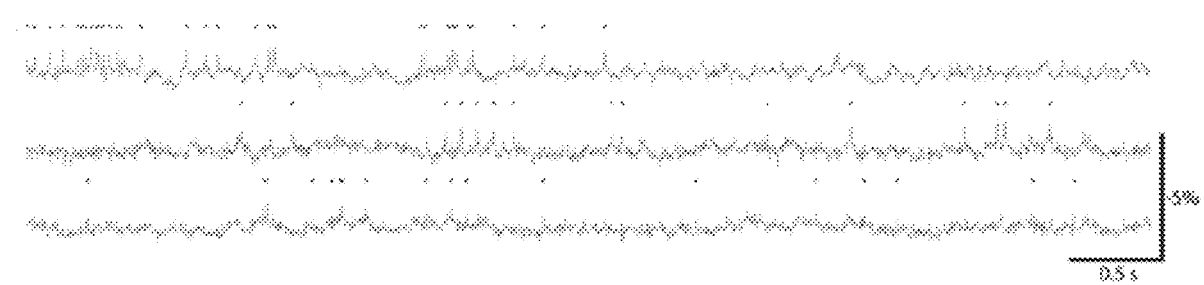
FIG. 33D includes zoom-in of fluorescence traces from area indicated by red rectangle in FIG. 33C.
Figure 34A:
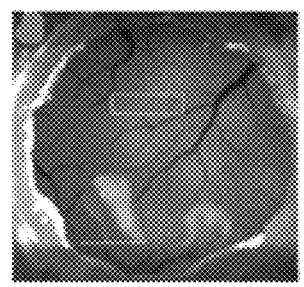
FIG. 34A includes a fluorescence image of a cranial window over primary visual cortex (V1) in an NDNF-Cre mouse showing Cre-dependent expression of soma targeted Voltron525. Scalebar, 1 mm.
Figure 34B:
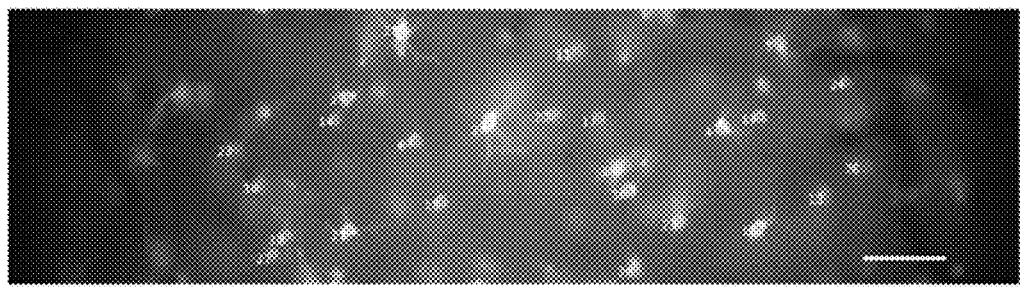
FIG. 34B includes fluorescence image of area indicated by the white rectangle in FIG. 34A, with neuron labels corresponding to fluorescence traces in FIG. 34C. Scalebar, 100 μm.
Figure 34C:
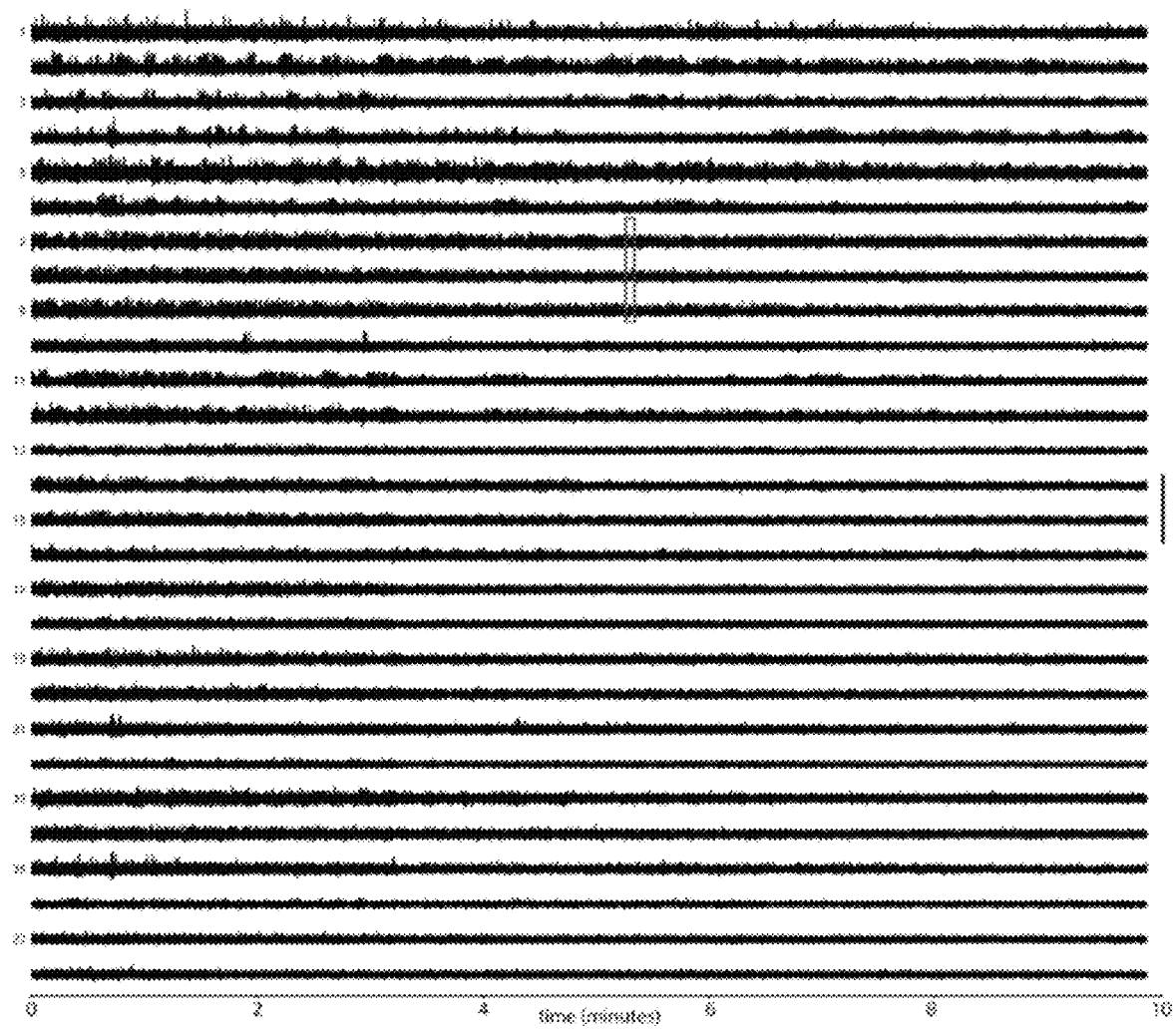
FIG. 34C includes fluorescence traces during 10-15 minutes recordings from neurons indicated in FIG. 34B, in decreasing order of signal to noise ratio.
Figure 34D:
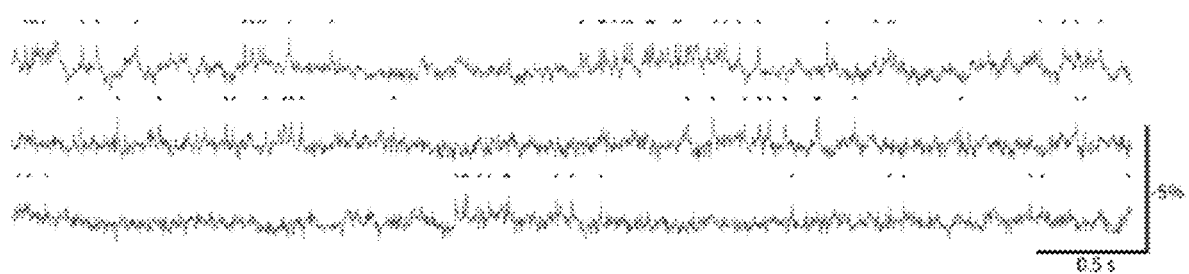
FIG. 34D includes zoom-in of fluorescence traces from area indicated by red rectangle in FIG. 34C.
Figure 35A:
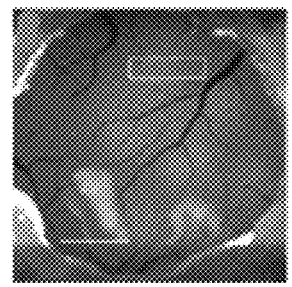
FIG. 35A includes fluorescence image of a cranial window over primary visual cortex (V1) in an NDNF-Cre mouse showing Cre-dependent expression of soma targeted Voltron525. Scalebar, 1 mm.
Figure 35B:
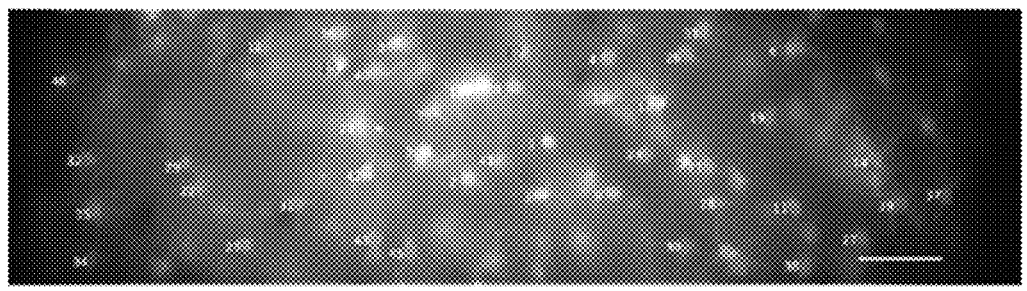
FIG. 35B includes fluorescence image of area indicated by the white rectangle in FIG. 35A, with neuron labels corresponding to fluorescence traces in FIG. 35C. Scalebar, 100 μm.
Figure 35C:
FIG. 35C includes fluorescence traces during 10-15 minutes recordings from neurons indicated in FIG. 35B, in decreasing order of signal to noise ratio.
Figure 35D:
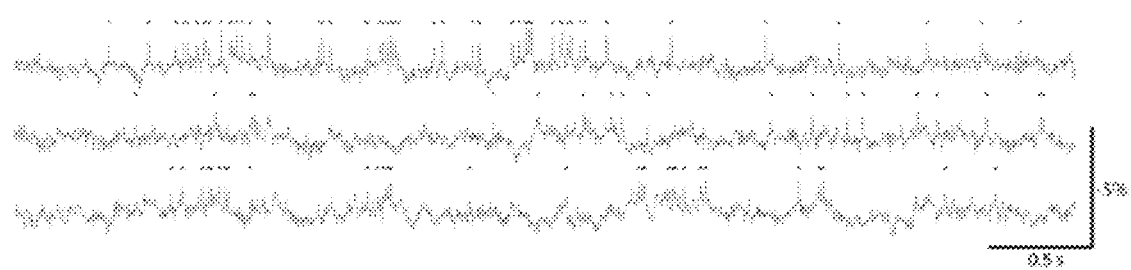
FIG. 35D includes zoom-in of fluorescence traces from area indicated by red rectangle in FIG. 35C.
Figure 36A:
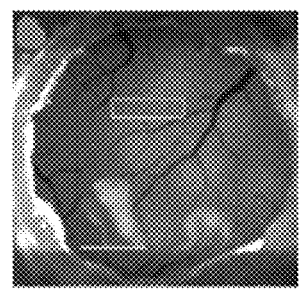
FIG. 36A includes a fluorescence image of a cranial window over primary visual cortex (V1) in an NDNF-Cre mouse showing Cre-dependent expression of soma targeted Voltron525. Scalebar, 1 mm.
Figure 36B:
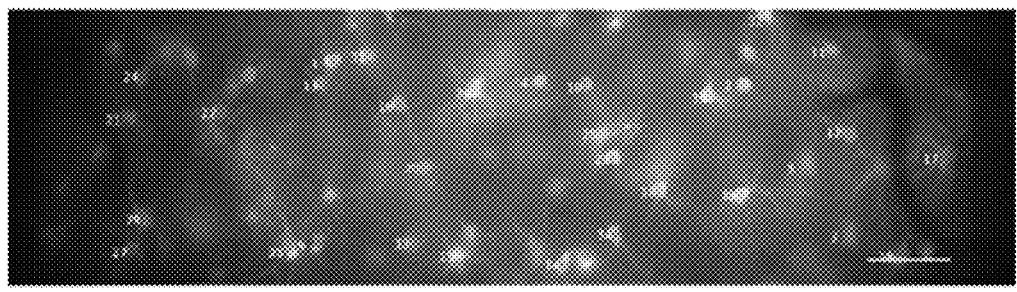
FIG. 36B includes fluorescence image of area indicated by the white rectangle in FIG. 36A, with neuron labels corresponding to fluorescence traces in FIG. 36C. Scalebar, 100 μm.
Figure 36C:
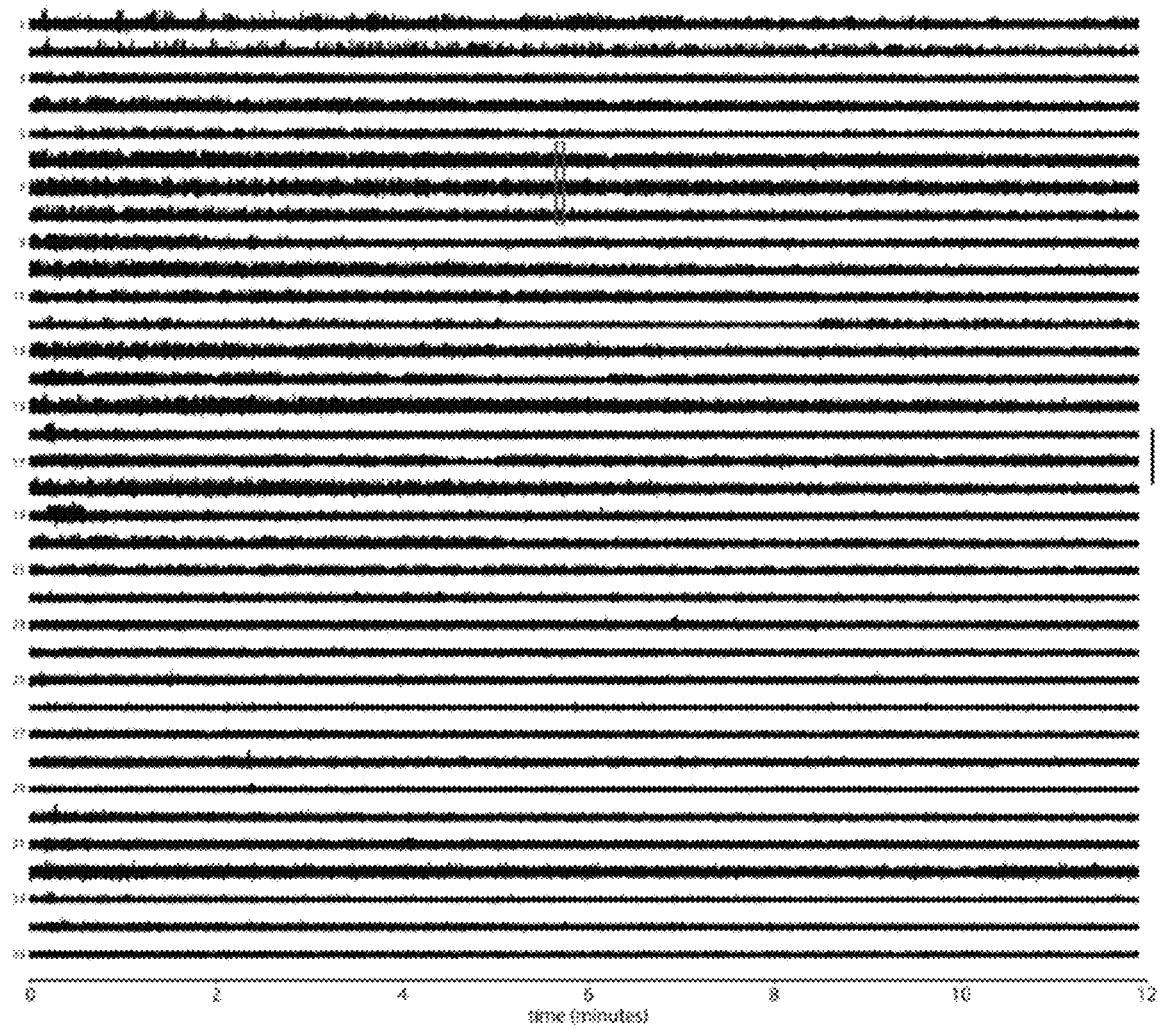
FIG. 36C includes fluorescence traces during 10-15 minutes recordings from neurons indicated in FIG. 36B, in decreasing order of signal to noise ratio.
Figure 36D:
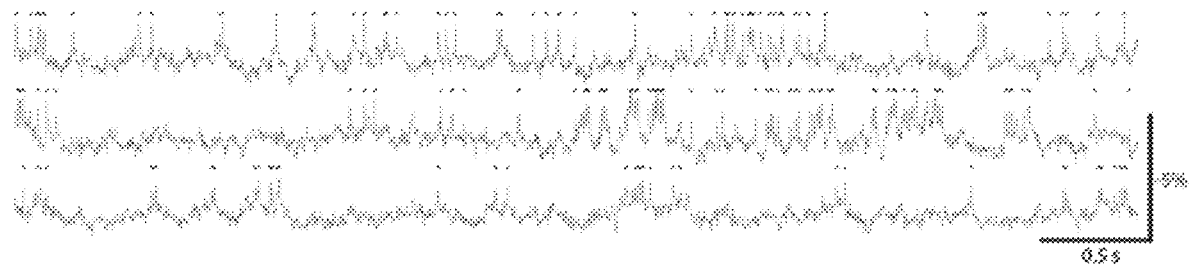
FIG. 36D Zoom-in of fluorescence traces from area indicated by red rectangle in FIG. 36C.
Figure 37A:
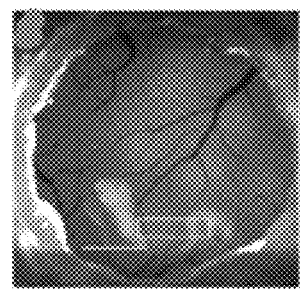
FIG. 37A includes a fluorescence image of a cranial window over primary visual cortex (V1) in an NDNF-Cre mouse showing Cre-dependent expression of soma targeted Voltron525. Scalebar, 1 mm.
Figure 37B:
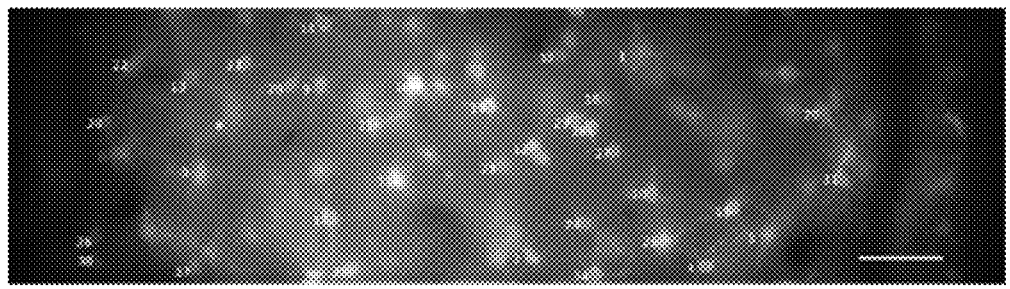
FIG. 37B includes fluorescence image of area indicated by the white rectangle in FIG. 37A, with neuron labels corresponding to fluorescence traces in FIG. 37C. Scalebar, 100 μm.
Figure 37C:
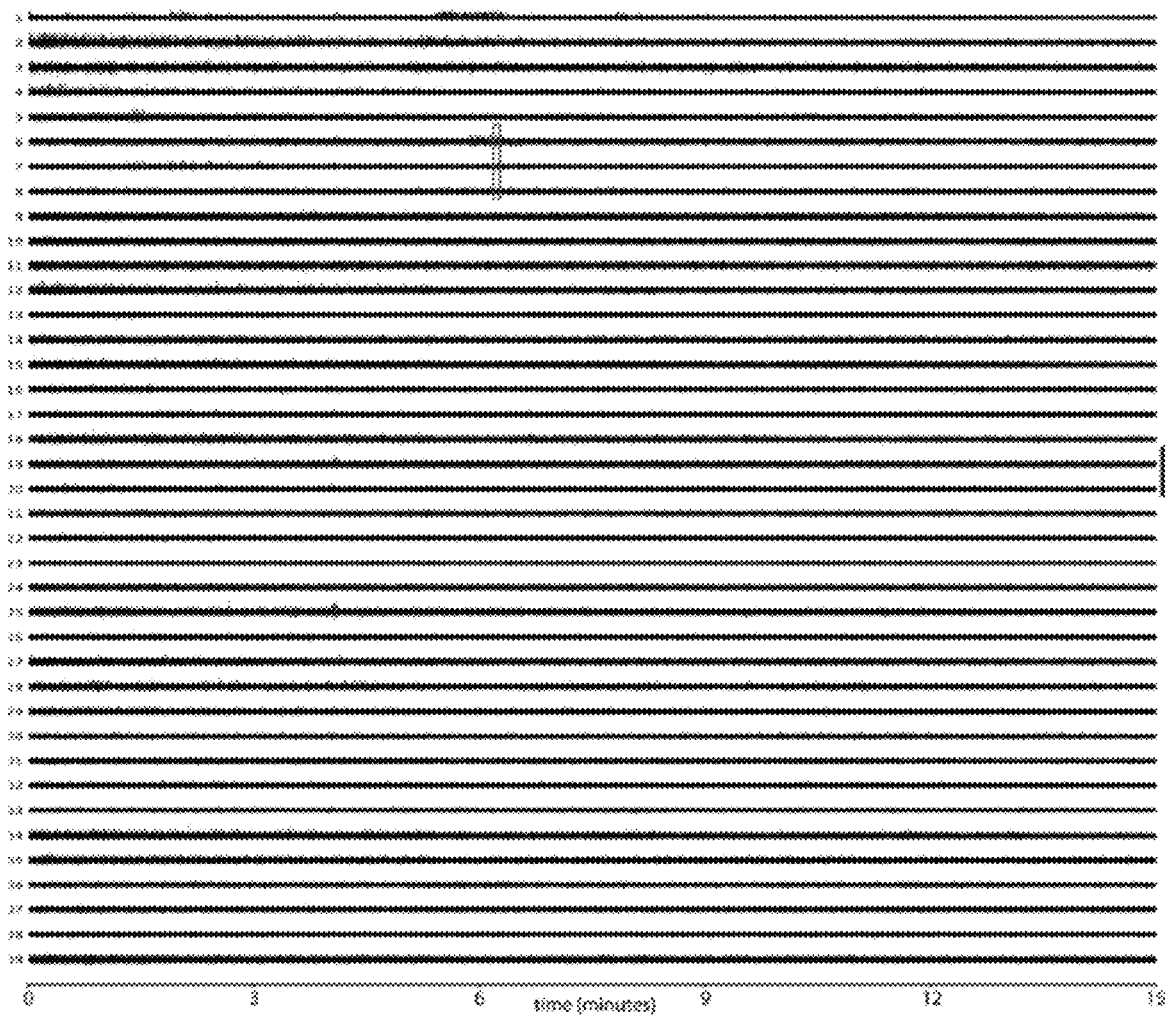
FIG. 37C includes fluorescence traces during 10-15 minutes recordings from neurons indicated in FIG. 37B, in decreasing order of signal to noise ratio.
Figure 37D:
FIG. 37D includes zoom-in of fluorescence traces from area indicated by red rectangle in FIG. 37C.
Figure 38A:
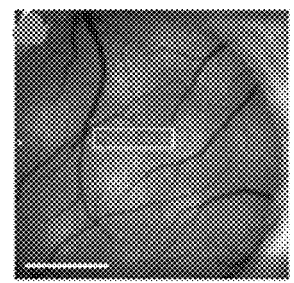
FIG. 38A includes a fluorescence image of a cranial window over primary visual cortex (V1) in an NDNF-Cre mouse showing Cre-dependent expression of soma targeted Voltron525. Scalebar, 1 mm.
Figure 38B:
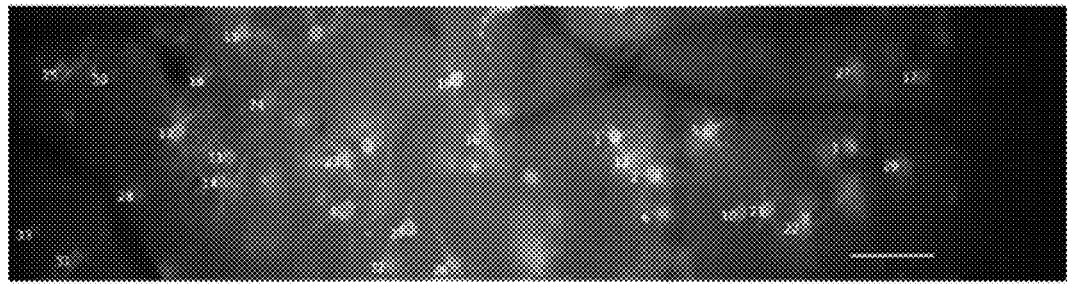
FIG. 38B includes a fluorescence image of area indicated by the white rectangle in FIG. 38A, with neuron labels corresponding to fluorescence traces in FIG. 38C. Scalebar, 100 μm.
Figure 38C:
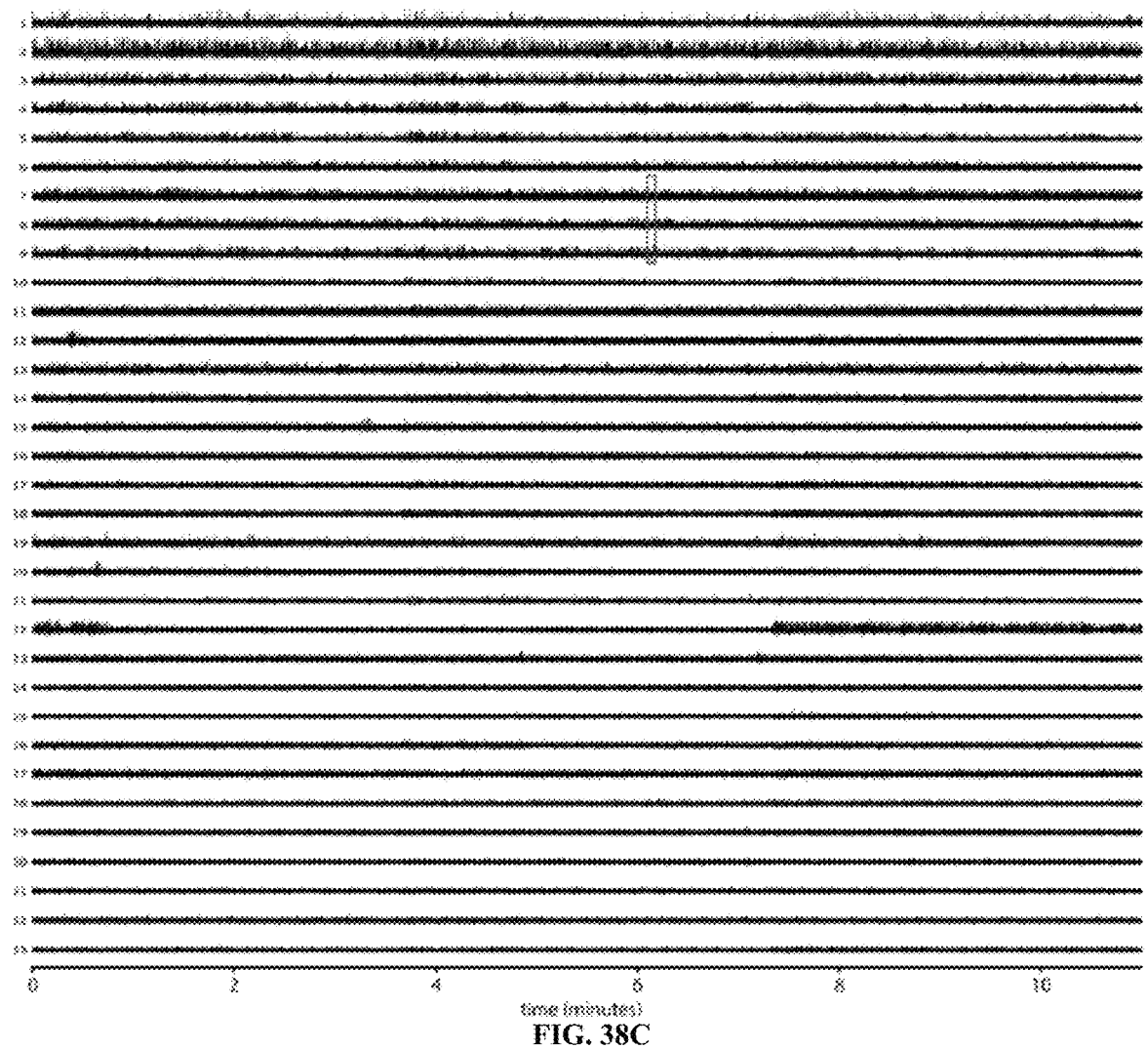
FIG. 38C includes fluorescence traces during 10-15 minutes recordings from neurons indicated in FIG. 38B, in decreasing order of signal to noise ratio.
Figure 38D:
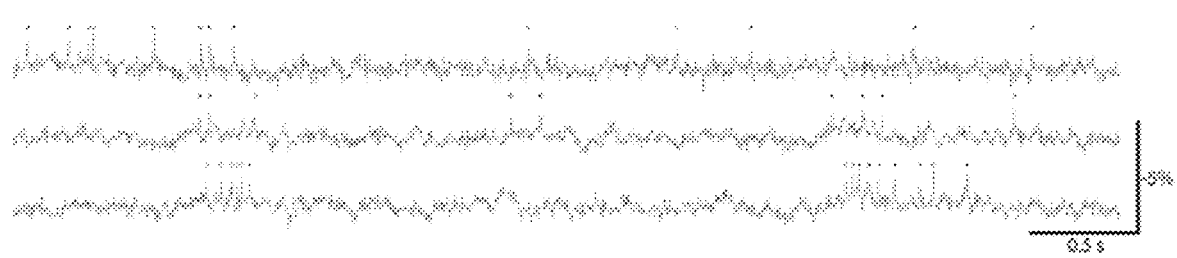
FIG. 38D includes zoom-in of fluorescence traces from area indicated by red rectangle in FIG. 38C.
Figure 39A:
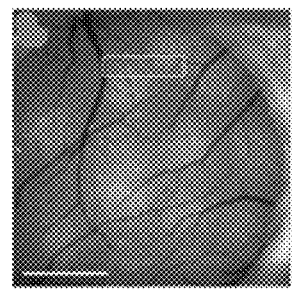
FIG. 39A includes a fluorescence image of a cranial window over primary visual cortex (V1) in an NDNF-Cre mouse showing Cre-dependent expression of soma targeted Voltron525. Scalebar, 1 mm.
Figure 39B:
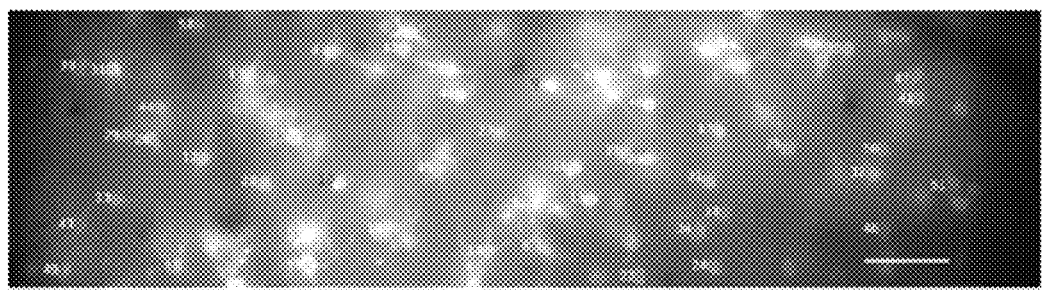
FIG. 39B includes a fluorescence image of area indicated by the white rectangle in FIG. 39A, with neuron labels corresponding to fluorescence traces in FIG. 39C. Scalebar, 100 μm.
Figure 39C:
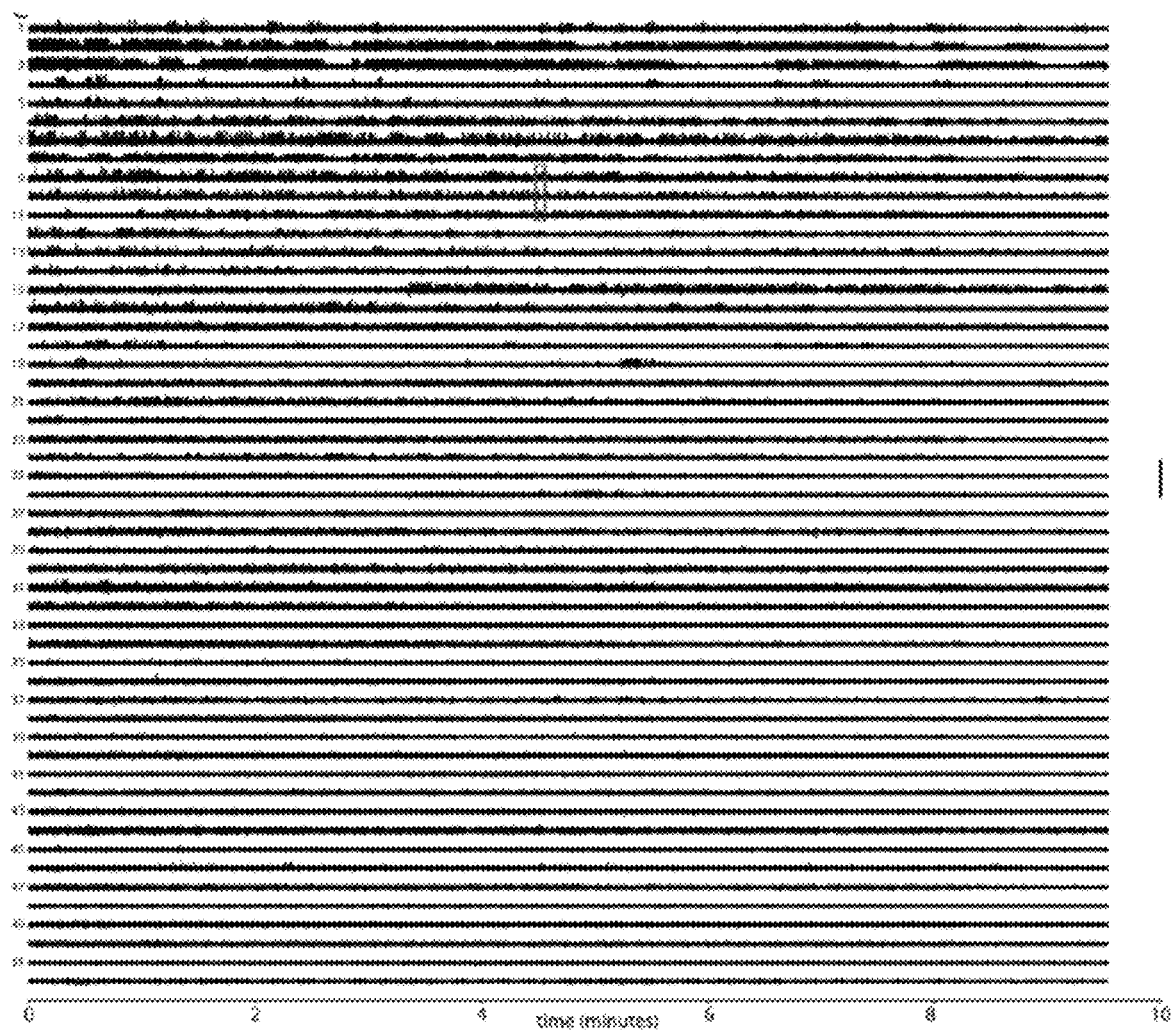
FIG. 39C includes fluorescence traces during 10-15 minutes recordings from neurons indicated in FIG. 39B, in decreasing order of signal to noise ratio.
Figure 39D:
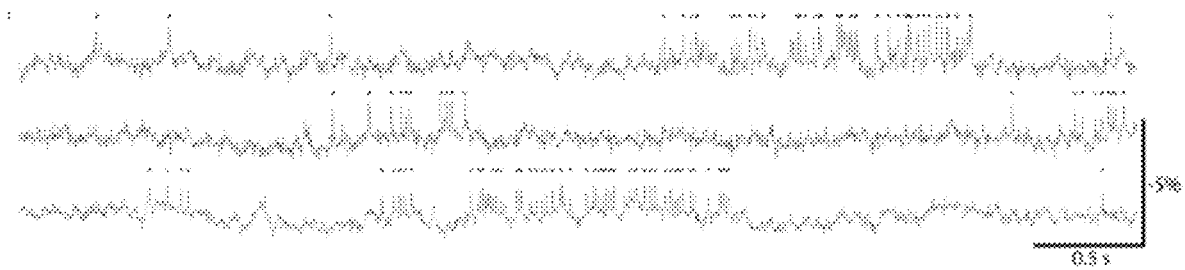
FIG. 39D includes zoom-in of fluorescence traces from area indicated by red rectangle in FIG. 39C.
Figure 40A:
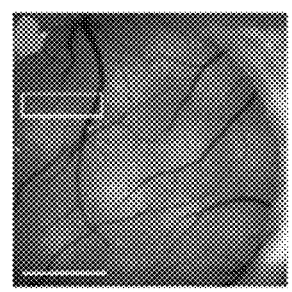
FIG. 40A includes a fluorescence image of a cranial window over primary visual cortex (V1) in an NDNF-Cre mouse showing Cre-dependent expression of soma targeted Voltron525. Scalebar, 1 mm.
Figure 40B:
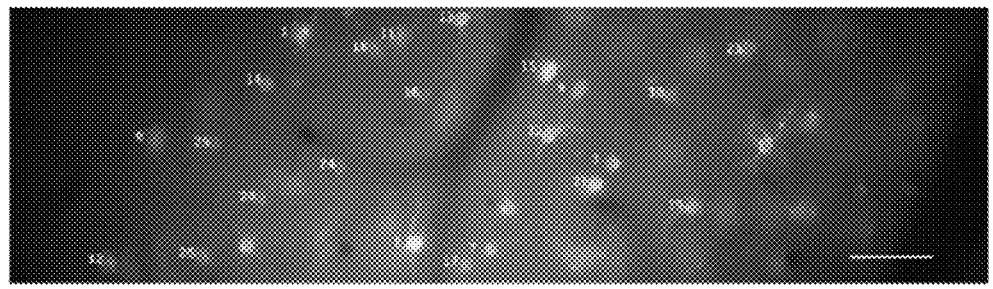
FIG. 40B includes a fluorescence image of area indicated by the white rectangle in FIG. 40A, with neuron labels corresponding to fluorescence traces in FIG. 40C. Scalebar, 100 μm.
Figure 40C:
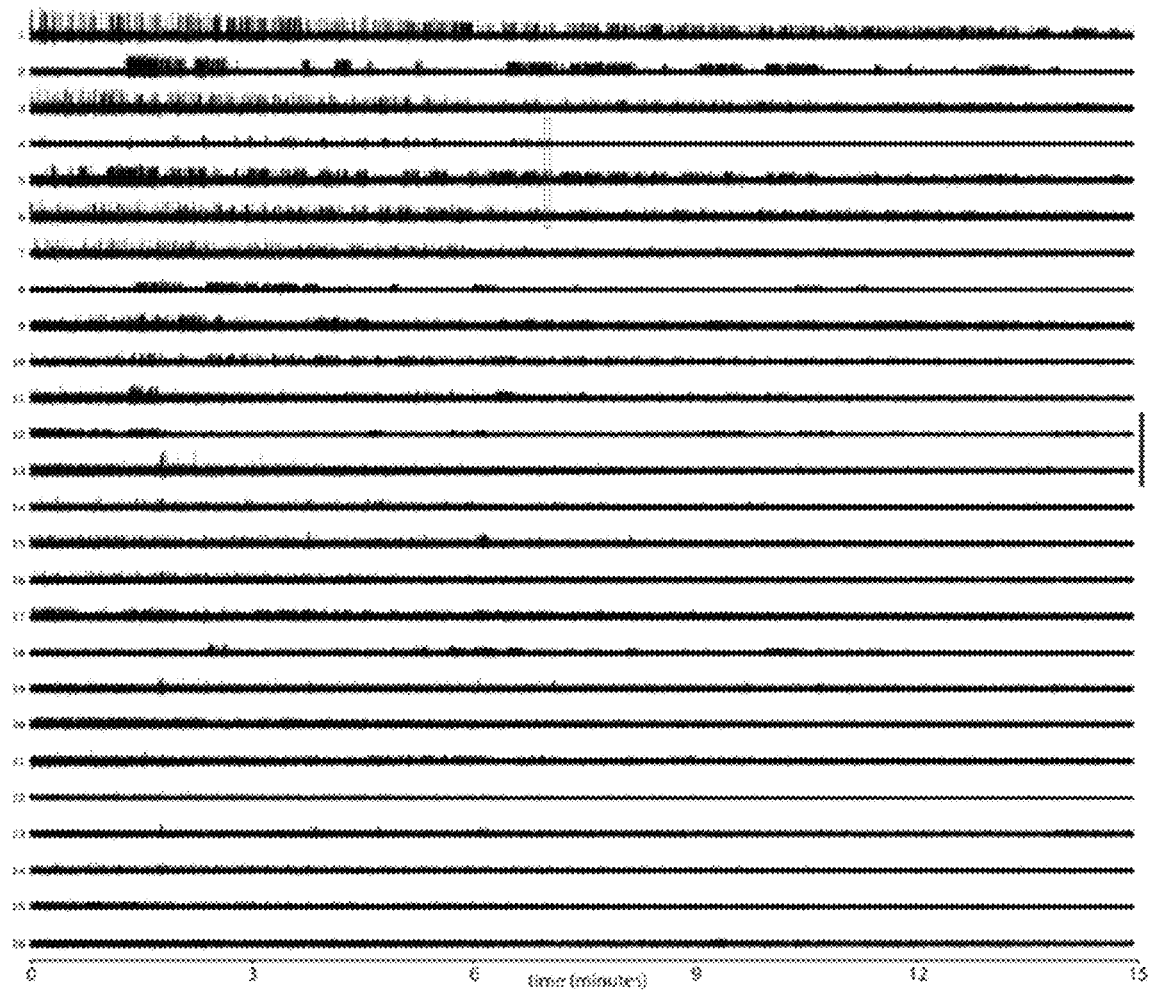
FIG. 40C includes fluorescence traces during 10-15 minutes recordings from neurons indicated in FIG. 40B, in decreasing order of signal to noise ratio.
Figure 40D:
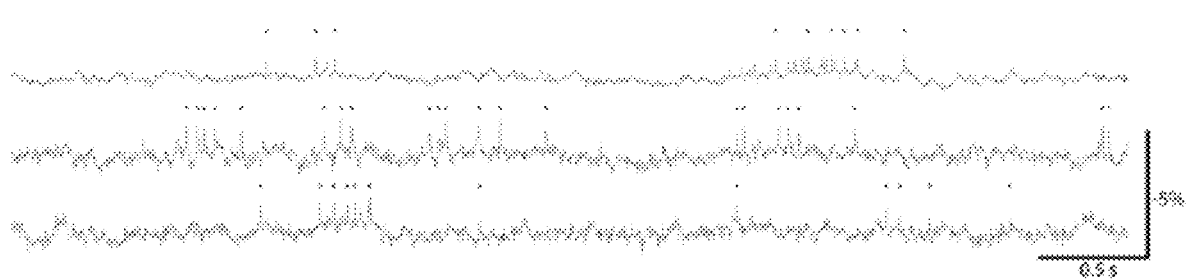
FIG. 40D includes zoom-in of fluorescence traces from area indicated by red rectangle in FIG. 40C.
Figure 41A:
FIG. 41A includes pictures of forebrain neurons expressing Voltron-ST labeled with Janelia Fluor 525 (JF525) with an inset schematic drawing showing the location of the image (Panel A1), and fluorescence signal from a neuron labeled with Voltron-ST+JF525 showing spontaneous spiking activity (Panel A2).
Figure 41A:
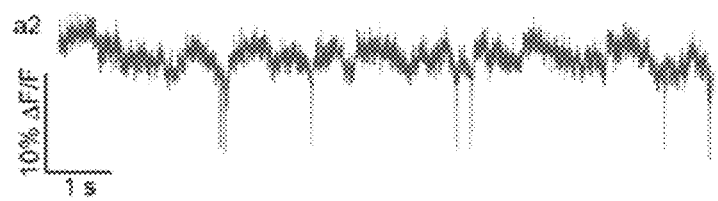
Figure 41B:
FIG. 41B includes pictures of forebrain neurons expressing Voltron-ST labeled with Janelia Fluor 549 (JF549) with an inset schematic drawing showing the location of the image (Panel B1), and fluorescence signal from a neuron labeled with Voltron-ST+JF549 showing spontaneous spiking activity (Panel B2).
Figure 41B:
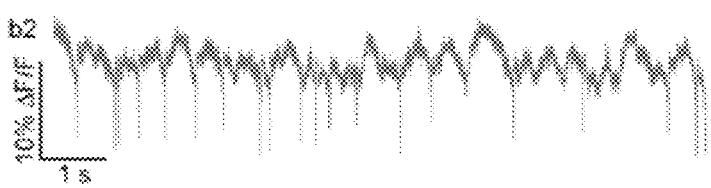
Figure 41C:
FIG. 41C includes pictures of forebrain neurons expressing Voltron-ST labeled with Janelia Fluor 585 (JF585) with an inset schematic drawing showing the location of the image (Panel C1), and fluorescence signal from a neuron labeled with Voltron-ST+JF584 showing spontaneous spiking activity (Panel C2).
Figure 41C:
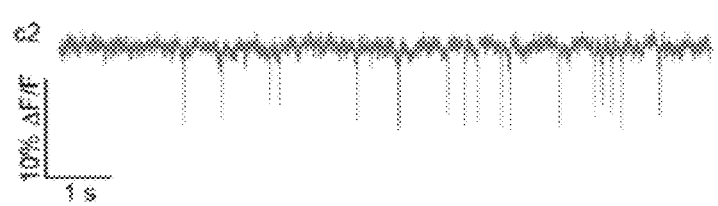
Figure 41D:
FIG. 41D includes pictures of forebrain neurons expressing Voltron-ST labeled with Janelia Fluor 635 (JF635) with an inset schematic drawing showing the location of the image (Panel D1), and fluorescence signal from a neuron labeled with Voltron-ST+JF635 showing spontaneous spiking activity (Panel D2).
Figure 41D:
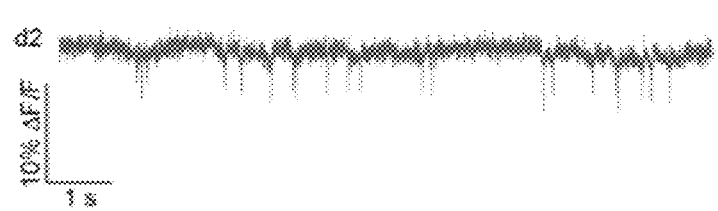

Motion was removed using Fast Fourier transform-based rigid registration in MATLAB. Initial ROIs were manually drawn around each neuron in the field of view. Data was processed in chunks of N=40,000 frames. The same initial ROIs were used for each chunk. For each neuron in each chunk, a region of 50×50 pixels centered on the neuron (the 'context region', C) was selected for further processing (FIG. 29). The data was high-pass filtered (MATLAB filtfilt) in the context region at 0.33 Hz using a $3^{rd}$ order Butterworth filter to correct for photobleaching. The high-pass filtered movie was denoted as $D_{N \times T}$ where N=n(C) is the number of pixels in the context region. The raw data was also high-pass filtered at 60 Hz using a $3^{rd}$ order Butterworth filter; this high-pass filtered movie as was denoted as $D_{N \times T}^h$.

The initial temporal trace $X_0(t)$ was the mean of the 0.33 Hz high-pass filtered video over the pixels in the ROI (R):

$$X_0(t) = \frac{1}{n(R)} \sum_{p \in R} D_{p,t}; t \in \{1, 2, \ldots T\}$$

where H denotes the set of pixels in the ROI, n(R) is the number of pixels in the ROI. $X_0$ and the high-pass filtered videos $D_{N \times T}$ and $D_{N \times T}^h$ were provided as input to the Spike Pursuit algorithm, which consisted of a two-step loop for each iteration (i):

Step 1: Spike Time Estimation

To detect spikes in the initial trace, contributions were subtracted from local background. This is intended to reduce the chance of optical crosstalk producing a false spike detection due to an adjacent neuron overlapping the initial ROI, and was not performed when computing the final trace with the optimized spatial filter. The 'local background' (B) was defined as the all pixels in the context region more than 12 pixels away from any pixel in the ROI, with M=n(B) pixels. The SVD (singular value decomposition) of the background movie was computed $D_{M \times T}^b$:

$$D_{M \times T}^b = U_{M \times M} \Sigma_{M \times T} V_{T \times T}^*$$

Multiple linear regression of the trace $X_{i-1}$ was performed against the top eight background principal components:

$$b_i = (V_8 * V_8)^{-1} V_8 * X_{i-1}$$

where $V_8$ is the first eight columns of V; $b_i$ are the regression coefficients. The trace $X_{i-1}(t)$ was denoised by subtracting the contribution of background pixels:

$$X_i^1 = X_{i-1} - V_8 b_i$$

$X_i^1(t)$ was high-pass filtered at 60 Hz using a third order Butterworth filter. Local minima in the filtered trace below a threshold $s_i$ were selected as an initial estimate of spike times. The threshold was chosen as follows: the distribution of local minima $P_{min,i}(x)$ was calculated by kernel density estimation and its median μ was computed. The distribution of the noise $P_{noise,i}(X)$ was estimated by symmetrizing about the median; i.e. setting.

$$\widetilde{P_{noise,i}}(\mu + x) := \begin{cases} P_{min,i}(\mu + x); & x > 0 \\ P_{min,i}(\mu - x); & x < 0 \end{cases}$$

The distribution of spikes $P_{spike}$ was estimated as:

$$\widetilde{P_{spike,i}}(x) := \max(0, P_{min,i}(x) - \widetilde{P_{noise,i}}(x))$$

The threshold was selected as:

$$s_i = \underset{s \in \mathbb{R}}{\operatorname{argmax}} \left( \sqrt{\int_{-\infty}^{s} \widetilde{P_{spike,i}}(x) dx} - \sqrt{\int_{-\infty}^{s} \widetilde{P_{noise,i}}(x) dx} \right)$$

Thus, the initial estimate of spike times was $$S_i = \{t | X_i^1(t) < s_i, X_i^1(t) < X_i^1(t+1),$$

$$X_i^1(t) < X_i^1(t-1)\}.$$

This approach assumes that spikes only occur in a small proportion of time points, that $P_{noise}(X)$ is symmetric about μ in the absence of spikes, that local minima are uncorrelated to the voltage trace in the absence of spikes, and that no spikes produce local minima larger than μ. These assumptions are only approximately satisfied, but results of this method agree well with manual threshold selection.

Following the first round of spike detection, an action potential template $Z_i(\tau)$ was generated as:

$$Z_i(\tau) = \frac{1}{n(S_i)} \sum_{t \in S_i} X_i^1(t + \tau); \tau \in [-20 \text{ ms}, 20 \text{ ms}]$$

The template $Z_i(\tau)$ was used to perform a whitened matched filter (39) on $X_i^1(t)$, producing the temporally filtered trace $X_i^f(t)$. $X_i^f(t)$ was again adaptively thresholded to obtain the estimated spike times $S_i^f$ for iteration i, and regenerate the action potential template, $Z_i^f(c)$.

Step 2: Spatial Filter Estimation

A target trace $\hat{X}_i(t)$ was produced by convolving the action potential template with the spike time indicator function:

$$\hat{X}_i = Z_i^f * Y_i \text{ where } Y_i(t) = \begin{cases} 1, t \in S_i^f \\ 0, \text{otherwise} \end{cases}$$

A spatial filter wiN×(was estimated by ridge regression of the target trace $\hat{X}_t$ against $D_{N \times T}^h$ (FIG. 29).

$$w_i = (D^{h*} D^h + \lambda (\|D^h\|_F^2) I)^{-1} D^{h*} \hat{X}_t$$

Where $\|D^h\|_F$ is the Frobenius norm of the high pass filtered data. The regularization parameter λ, was selected by cross-validation on one dataset, and fixed for the remaining datasets. The activity trace corresponding to the spatial filter was calculated:

$$X_i = D w_i$$

The Spike Pursuit loop was performed for five iterations. As a final step, the contribution of pixels was removed from a 'global background' (G), defined as the entire field of view excluding all pixels less than 12 pixels away from any ROI, with L=n(G) pixels. The SVD of the global background movie was high pass filtered at 0.3 Hz, $D_{L \times T}^g$:

$$D_{L \times T}^g = U_{L \times L}^g \Sigma_{L \times T}^g V_{T \times T}^{g*}$$

Multiple linear regression of the trace $X_5$ was performed against the top 8 principal components of the global background movie:

$$b_g = (V_8^g * V_8^g)^{-1} V_8^g * X_5$$

$$X_{final} = X_5 - V_8^g b_g$$

Figure 27A:
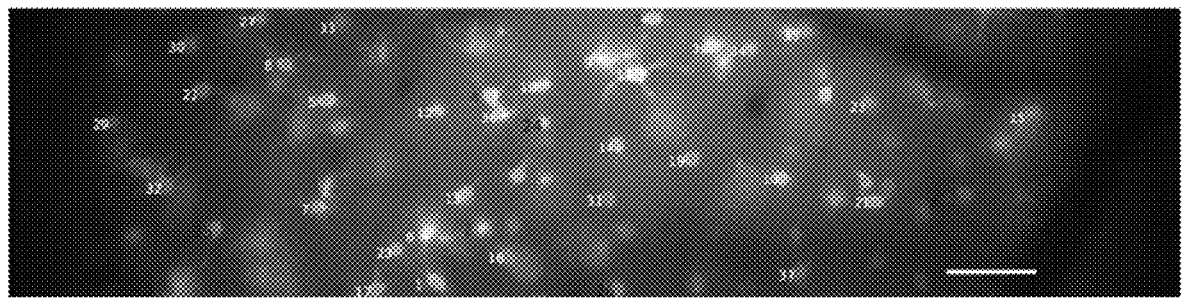
FIG. 27A includes an image showing Layer 1 interneurons expressing Voltron525 (same field of view as in FIG. 3F). Scalebar: 100 μm.
Figure 27B:
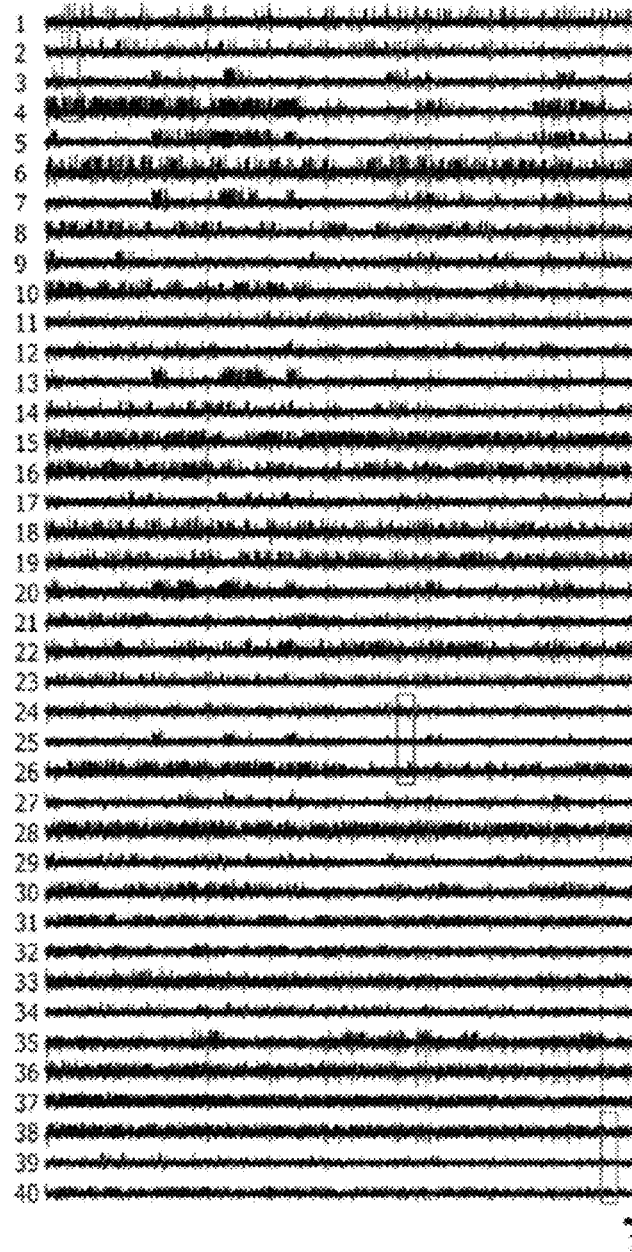
FIG. 27B includes fluorescence traces from neurons labeled in FIG. 27A, in decreasing order of signal to noise ratio. Signals processed as in FIG. 7G but without the last step of global background subtraction.
Figure 27C:
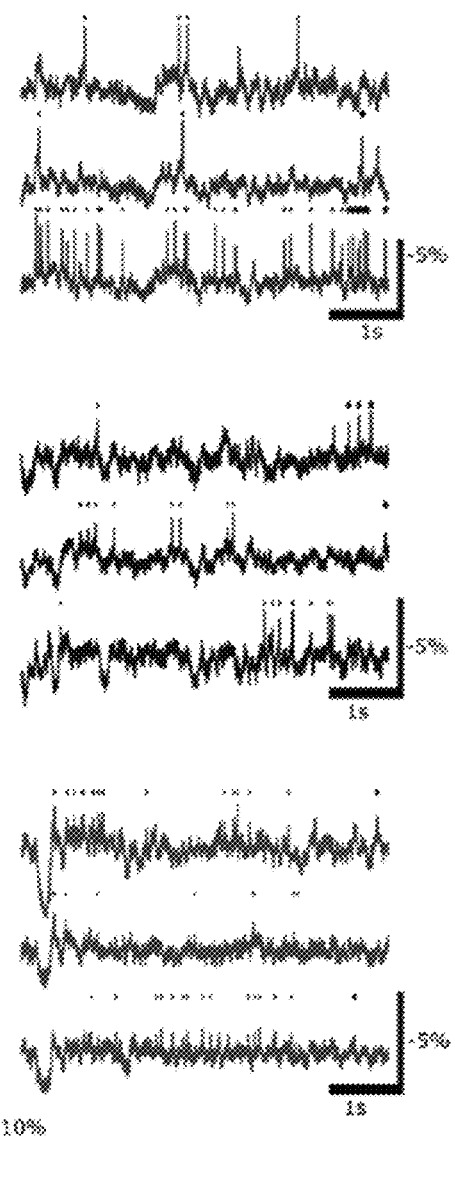
( FIG. 27C includes image zooms of fluorescence traces from color coded regions of FIG. 27A with detected action potentials represented as black dots above, illustrating representative traces with high (top), medium (middle), and low (bottom) SNR.

Global background subtraction removes fluorescence fluctuations that are shared across most pixels of the movie. It remains unclear to what degree these fluctuations reflect shared membrane potential transients versus other sources of shared variability. Traces without global background subtraction ($X_5$) are shown in FIG. 27.

Calculating spike triggered averages for layer 1 interneurons: For each pair of neurons (p, q) the spike triggered average from neuron p to neuron q was calculated as:

$$STA_{p \to q}(\tau) = \frac{1}{n(S_5^p)} \sum_{t \in S_5^p} X_5^q(t+\tau); \tau \in [-200 \text{ ms}, 200 \text{ ms}]$$

Figure 28A:
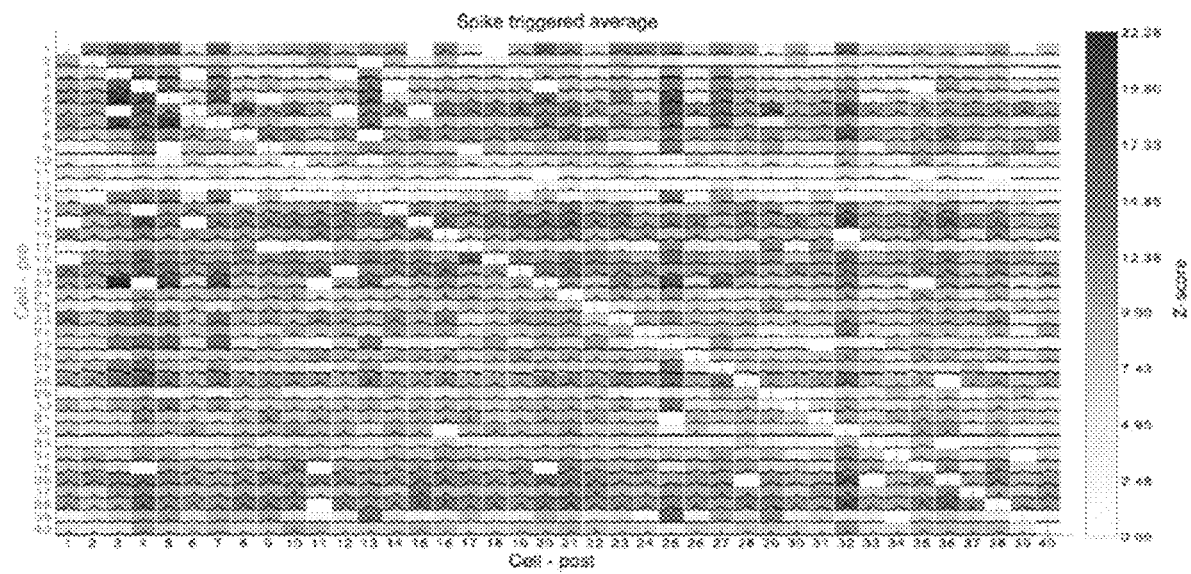
FIG. 28A-28D include spike triggered averages of neuron ensemble.
Figure 28B:
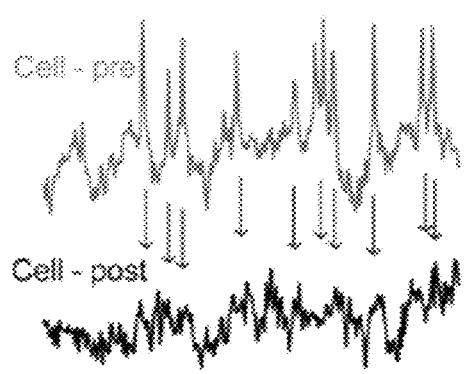
Figure 28C:
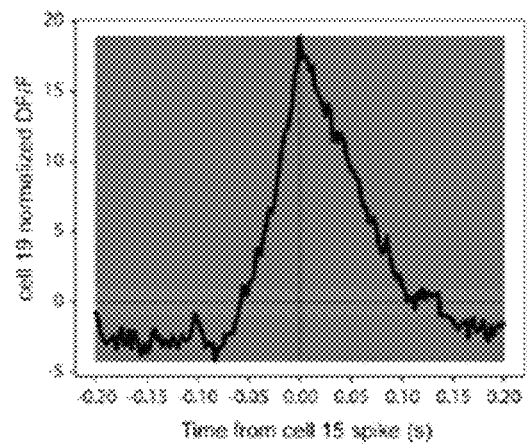
Figure 28D:
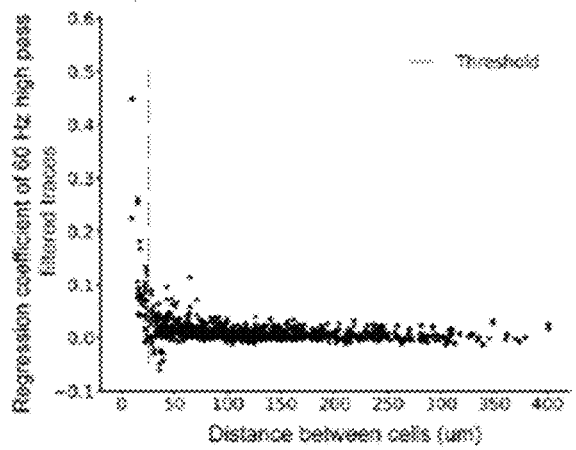

To calculate the shuffled distribution of spike triggered averages, each spike time was shifted by a random amount ranging from 2 s to 4 s (minimum of 2 s chosen based on the typical autocorrelation function of the fluorescence traces). The spike triggered average of each pair was normalized by the standard deviation of the distribution of shuffled spike triggered averages (gray bar in FIG. 28C). The 'modulation' of one neuron was estimated by another as the L2 norm of the spike triggered average. To z-score this norm, a log-normal distribution was fit to its shuffle distribution. The background color in FIG. 28A and FIG. 28C represents this z-score.

Similar results (not shown) were obtained for the spike triggered averages using raw fluorescence traces, calculated as:

$$STA_{p \to q}(\tau) = \frac{1}{n(S_5^p)} \sum_{t \in S_5^p} X_0^q(t+\tau); \tau \in [-200 \text{ ms}, 200 \text{ ms}]$$

Transgenic zebrafish: Transgenic zebrafish which expresses Voltron under UAS promoter were generated as follows. A sequence of Voltron (Ace2-HaloTag) was cloned downstream of a 10×UAS sequence and the E1B minimal promoter (40). This plasmid was injected into 2-cell stage embryos of Casper mutant zebrafish (41) with mRNA of Tol2 transposase (42) to generate founder (F0) transgenic zebrafish.

Figure 15A:
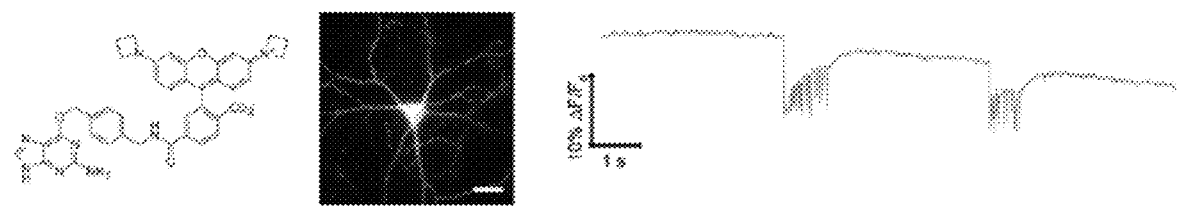
FIG. 15A includes, Left: Chemical structure of JF549-SNAP-tag ligand, Middle: fluorescence image of hippocampal neurons in culture expressing QuasAr2-SNAP-tag labeled with $JF549$. Right: Fluorescence trace over time showing voltage-dependent fluorescence changes resulting from spontaneous action potentials of the neurons.
Figure 15B:
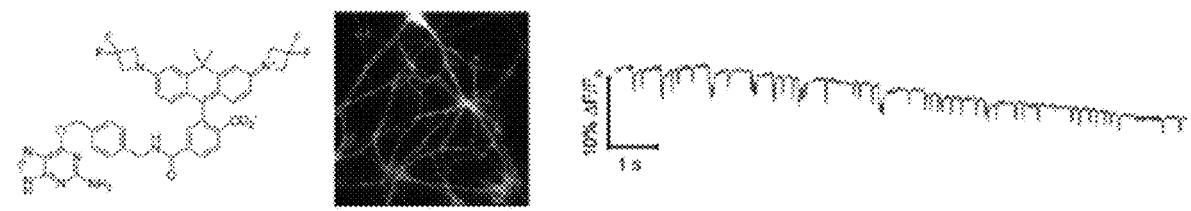
FIG. 15B includes, Left: Chemical structure of JF585-SNAP-tag ligand, Middle: fluorescence image of hippocampal neurons in culture expressing QuasAr2-SNAP-tag labeled with JF585. Right: Fluorescence trace over time showing voltage-dependent fluorescence changes resulting from spontaneous action potentials of the neurons. Scale bar: 20 µm FIG. 16 includes representative fluorescence traces of Voltron525 in response to a series of voltage steps (from −110 mV to +50 mV in 20 mV increments). Image acquisition rate=400 Hz.

Transgenic zebrafish which expresses Voltron under elavl3 promoter for FIG. 15 were generated as follows. A sequence of Voltron (Ace2-HaloTag) and its soma-localized variant (Ace2-HaloTag-SOM2) was cloned downstream of an elavl3 promoter sequence. This plasmid was injected into 2-cell stage embryos of Casper mutant zebrafish (41) with mRNA of Tol2 transposase (42) to generate founder (F0) transgenic zebrafish. Images of the brains of their embryos (F1) were used for FIG. 20.

Experiments described in FIGS. 8 and 42 were performed using embryos generated by crossing the UAS: Voltron F0 founder and vglut2a:Gal4 transgenic zebrafish (43) (a gift from Dr. Shin-ichi Higashijima). To label Voltron-expressing neurons with the accompanying fluorescent dye, 4-day old embryos were incubated in dye solution [3.3 µM $JF_{525}$-HaloTag ligand (17) and 0.3% DMSO] in fish rearing water at room temperature for two hours. After screening for the fluorescence of the JF dye in the brain, the fish were returned to fish rearing water with food until the time of the experiment.

Preparation for zebrafish imaging experiments: Imaging experiments were performed using 5- or 6-day larval zebrafish. The zebrafish was immobilized and mounted to an imaging chamber as described previously (44) with minor modifications. Briefly, the zebrafish were habituated in an artificial cerebrospinal fluid (ACSF) [in mM: 120 NaCl, 2.9 KCl, 2.1 CaCl2, 1.2 MgCl2, 20 NaHCO3, 1.25 NaHPO4, 10 Glucose] bubbled with carbogen gas (95% oxygen, 5% carbon dioxide) for 30 minutes. The muscle of the zebrafish was paralyzed by a short (up to 30 seconds) bath incubation with alpha-bungarotoxin (1 mg/ml, Thermo Fischer Scientific, B1601) dissolved in external solution. After the fish became immobile, heart movement of the zebrafish was stopped by microforceps to prevent the shadowing effect of blood cells in the brain during imaging experiments. The zebrafish showed robust optomotor behavior in ACSF (bubbled with carbogen gas for 30 minutes before the experiment) for several hours after this treatment. The zebrafish was further mounted to a custom-made chamber using 2% agarose (Sigma-Aldrich, A9414) and placed under a light-sheet microscope (45) with a 20× objective lens (Olympus, XLUMPLFLN).

Light-sheet imaging of zebrafish Voltron signals: Imaging was performed in a light-sheet microscope according to a published design (46) with modifications targeted at optimizing Voltron imaging. To increase the fraction of time the imaged cells were exposed to the excitation laser beam, the beam was expanded in the horizontal dimension using a pair of cylindrical lens (LJ1878L1-A (f=10 mm) and LJ1402L1-A (f=40 mm), Thorlabs). Imaging was performed using a 488 nm excitation laser (80 µW) and a 562/40 emission filter (Semrock, FF01-562/40) and with a frame rate of 300 frames/second recorded by a sCMOS camera (Hamamatsu, ORCA Flash4.0 v2). In this setup, the pixel dimension on the camera was 0.293 µm/pixel and the imaged neurons occupied an area of 150-200 pixels on the image.

Simultaneous cell-attached extracellular recordings and voltage imaging in zebrafish: Electrophysiology and imaging of neurons expressing Voltron in Tg(vglut2:Gal4); Tg(UAS: Voltron) transgenic zebrafish were simultaneously performed as described previously (44) with a minor modification. Fire-polished borosilicate glass pipettes (Sutter, BF150-75-7.5) were pulled using a heat puller (Sutter, P1000). The tip of the pipette was further coated by quantum dots (Ocean Nanotech, QSR-600) using a previously reported method (47). The pipette resistance after the quantum dot coating was 10-12 MΩ.

The fish was bathed in an external solution and a small incision on the top of the head was made using a sharp glass needle. The pipette was filled with an external solution and inserted into the cerebellum of the brain using a micromanipulator (Sutter, MPC-200), and extracellular spiking signals were recorded from vGlut2-positive neurons in the dorsal part of the cerebellum using cell-attached extracellular recordings. These neurons are assumed to be eurydendroid neurons in the cerebellum, homologues of neurons in the deep cerebellar nuclei in mammalian brains (48), based on their previously described anatomical locations (49) and their expression of the vglut2 gene (49). Signals from the pipette were amplified by an amplifier (Molecular Devices, AxoClamp 700B) and recorded by custom software written in C# (Microsoft) at 6 KHz. Optical signals from the same neurons were simultaneously imaged as described above.

Behavioral experiments in zebrafish: Recording of fictive swim signals and presentation of visual stimuli were performed as described previously (44, 45). To record swim signals from the axonal bundles of spinal motoneurons in the tail, a pair of large barrel electrodes was attached to the dorsal left and right side of the tail. Signals were amplified by an amplifier (Molecular Devices, AxoClamp 700B) and recorded at 6 KHz using custom software written in C#

(Microsoft). For synchronization between the swimming signals and neural activity imaging, camera trigger signals that initiate the acquisition of individual frames in the light-sheet microscope were recorded simultaneously with the swim signals. During the experiments, red visual stimuli (red/black gratings with bars 2 mm thick) was projected to the bottom of the fish chamber. The speed of the moving the visual stimulus alternated between 0 mm/s (stopped) and 2 mm/s (moving forward) every 10 seconds. Every trial (20 seconds) contained a stop period and a forward-motion period. In a subset of tested fish, the forward moving speed was changed from 2 mm/s to 0.5 mm/s every other trial. Swimming behavior was continuously recorded for a duration ranging from 6 minutes to 12 minutes (18 to 36 trials).

Signals from the electrodes were processed and individual swim events were detected according to a method described previously (44). Briefly, the raw signals were high-pass filtered, squared and smoothed by applying a Gaussian filter ($\sigma=3.3$ milliseconds). The resulting traces were defined to be the swim signal, as shown in FIG. 8. Individual swim bouts were detected by finding the time points at which the swim signal crossed a threshold. This threshold was automatically set to lie just above a noise level based on a histogram of the swim signals (45, 50).

Analysis of imaging dataset: The flow of the data processing is described below and in FIGS. 42B and 42C. Custom Python scripts are provided for this analysis on Github (git.io/vA2Ee).

Step 1. Image Registration

Sequences of recorded images were corrected for horizontal drift during the imaging session at the subpixel level with a phase correlation algorithm (51) using a custom Python script and a GPU computing board.

Step 2. Segmentation of Neurons

Individual neurons in the imaging field were segmented in a semi-automatic way. This was done using a combination of cell recognition by a pre-trained convolutional neural network build with the Python Keras library (keras.io/) and manual correction. This convolutional network discriminates whether a locally darkest point in a circular patch (radius=2.67 µm) is a center of a Voltron-expressing neuron or not. Once the cells are segmented, ring-shaped masks are drawn automatically over the cells ($1^{st}$ pixel weights in FIGS. 42B and 42C). This is achieved by (1) selecting the brightest points on a line (at 0 degrees) from the center of a cell, (2) selecting such points for different angles around the cell (0 to 342 degrees in 18-degree steps), (3) smoothing the line connecting these brightest points by median filtering the distance from the center of the cell to the brightest points, and (4) dilating the resulting line by 1 pixel. Pixels on this dilated line are given an initial weight of 1, and all other pixels an initial weight of 0, to create the mask.

Step 3. Optimization of Pixel Weights for Individual Neurons

Weights on the pixels of the above masks were optimized to maximize the signal-to-noise ratio of the voltage signals in individual neurons (FIG. 42C). This is necessary because the light scattering through the tissue during the imaging experiment mixes to a small extent the optical signals across pixels surrounding the cell. This process optimizes the weights on the pixels over the cell to maximize the objective function J:

$$J = \frac{(E(F_S))^2}{\text{Var}(F)} - \|W\|^2$$

where W is a matrix of weights over pixels, Var(F) is a variance of a weighted mean fluorescence time-series of candidate pixels using W, $E(F_s)$ is the average of the weighted mean fluorescent values at the time of detected spikes, and $\|\mu W\|^2$ is the $L^2$ norm of the pixel weights for regularization. This objective function measures the ratio between the mean heights of the spikes and the noise level of the estimated fluorescence time-series of a cell. Pixel weights W are optimized so that they maximize the objective function J using a gradient ascent method. Spiking events used for this optimization are detected using the fluorescence time series of the $1^{st}$ pixel weights using the same algorithm as described below. The final fluorescence time series is obtained by (1) calculating the weighted average of fluorescence values across pixels using the optimized W, (2) subtracting the camera background (i.e., the pixel value when the camera records dark images), and (3) normalizing the resulting time-series by dividing by its baseline time-series, which is a rolling percentile (80% [since Voltron becomes dimmer with increasing voltage, an upper percentile was used instead of a lower percentile used for calcium imaging data], 500-ms time window) of the time-series.

Step 4. Spike Detection

Lastly, spiking events were detected for individual neurons using an iterative method that first estimates the subthreshold potential and subtracts it from the raw voltage trace, and secondly estimates spiking events on the resulting trace. These three steps were iterated three times:

1. The subthreshold potential was obtained by subtracting the current estimate of the voltage trace attributable to spikes (i.e. the convolution of the estimated spike train s with spike shape k, s*k) from the raw trace followed by low pass filtering to remove the noise. Using a simple Butterworth filter of order 5 with a cutoff at 10 Hz was effective. Subtracting the subthreshold potential yielded the high-frequency component y that consists of voltage transients due to spikes corrupted by noise.
2. Spiking events were detected using a method based on adaptive template matching. First, large spiking events were detected using a high threshold (3.5*rolling standard deviation+rolling median, window size of 3 seconds) to avoid false positives. The neuron's spike shape was constrained to have non-zero values only in a small window around the time of a spike and was calculated using linear regression of y on s.
3. The less clear spike events were detected using this mean spike shape k as a template instead of merely relying on a threshold. Potential spike candidates were detected using a low threshold (2.5*rolling standard deviation+rolling median) to avoid false negatives. Template matching by regressing y on k yielded the sizes of these candidate events. The candidates that were not actual spikes but were merely due to noise had a small size and were iteratively removed with the regression being repeated. After the three outer iterations a reasonable estimate of the spike shape k and the spike times were obtained at frame-rate resolution.

Step 5. Validation of the Authenticity of the Detected Spikes

To minimize the false-positive detection rate of spiking events, the authenticity of the spike shapes were measured throughout the time-series by measuring the gradient of the voltage trace just before the estimated spiking events. This is based on an assumption that spiking events are always preceded with an increase of subthreshold membrane voltage and that non-spike high-frequency noise does not have this preceding component. The gradient of voltage signals from 10 milliseconds to 3.3 milliseconds (3 time points) before the spiking events were quantified for individual spikes. Detected spiking events were binned into contiguous blocks of 50 spiking events. The gradient values for each block of spiking events were tested for its deviation from zero using a Wilcoxon signed rank test. Spiking events in blocks that had significantly positive gradients (p<0.05) are used for subsequent analysis.

Analysis of the relationships between neural activity and behavior: Neurons that were used for analysis in FIG. 8 and FIG. 42 were statistically selected based on their modulation of spiking activity by visual stimuli and behavior. Two criteria were used for this. First, the difference of numbers of spikes in the two task periods (stop, forward visual motion) across multiple trials was tested using Wilcoxon's ranked sum test. Second, the modulation of subthreshold signals at the initiation of swim bouts (−100 ms to 100 ms) was tested across all swim bouts using two-way analysis of variance. Neurons which showed significant differences (p<0.05) for both criteria were used for subsequent analyses. A total of 468 neurons from 81 fish were tested, and 179 neurons from 43 fish were used for subsequent analyses.

Figure 42E:
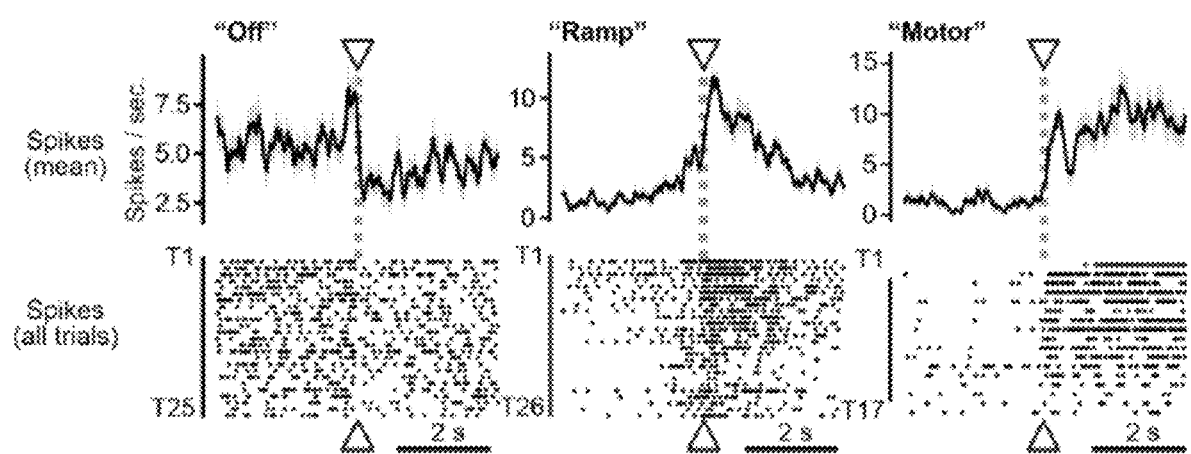

Mean subthreshold signals and firing rates on FIGS. 8E and 42E were smoothed by gamma density causal filters (t*exp(−t/θ) for t>0) with a hyperparameter θ set differently for each panel (3.3 ms for FIG. 8E and 200 ms for FIG. 42E).

For classifying neurons in FIG. 8E, subthreshold voltage signals were first smoothed by a gamma density causal filter (θ=3.3 ms) and then averaged centered at the onset of all swim bouts (−100 to +100 milliseconds, 60 time points). The resulting averaged subthreshold signals were normalized to between 0 and 1 using their minimum and maximum values. Non-negative matrix factorization (NMF) was applied to the pool of these normalized subthreshold signals with a prior number of components set to 3. It was confirmed that three components similar to the ones shown in FIG. 8D ('Off', 'Onset' and 'Late') always appear as NMF components regardless of the initial conditions. Component weights for each of the neurons are further adjusted so that the sum of weights for three components becomes 1, and these adjusted weights are allocated to red, green and blue channels to color neurons.

Widefield imaging of Voltron expressing neurons in zebrafish: Mitfa$^{w2/w2}$ roy$^{a9/a9}$ (Casper) zebrafish were maintained under standard conditions at 28° C. and a 14:10 hr light:dark cycle. Embryos (1-2 cell stage) of Tg(elavl3: Gal4-VP16) were injected with 25 ng/μl DNA plasmid encoding the Voltron-ST indicator under the control of the 10×UAS promoter, and 25 ng/μl Tol2 transposase mRNA diluted in E3 medium.

Subsequently, the injected embryos at three day postfertilization (dpf) were incubated in system water containing JF dye-HaloTag ligands (JF$_{525}$, JF$_{549}$, JF$_{585}$ or JF$_{635}$) at 3 μM for 2 hours and then washed in dye-free system water. Larvae at 5 or 6 dpf were screened for the expression of the Voltron-ST based on the fluorescence from JF dye-HaloTag ligands. They were paralyzed by 5-min bath application of 1 mg/ml α-bungarotoxin (Sigma, 203980) and mounted dorsal-side up with 1.5% low-melting point agarose. Spontaneously active forebrain and olfactory neurons were imaged using a custom widefield microscope. The objective was a 60×1.0 NA water immersion lens (Nikon, MRD07620). Fluorophores were excited with a LED light source (Luminus, CBT-90-W for JF$_{525}$, JF$_{549}$ and JF$_{585}$; Luminus, CBT-90-RX for JF$_{635}$) with a proper filter set (Semrock, FITC-A-Basic-000 for JF$_{525}$; Semrock, Cy3-4040C-000 for $_{JF549}$; Semrock, LED-mCherry-A-000 for JF$_{585}$; Semrock, LF635-C-000 for JF$_{635}$). The images were acquired with sCMOS camera (PCO, pco.edge 4.2) at 400 Hz (2.5 ms exposure time) for 1-2 min. Data were analyzed using MATLAB (Mathworks). Regions of interest (ROIs) corresponding to identifiable cell bodies were selected manually and the mean signal from each ROI was extracted. The baseline was estimated by fitting the raw fluorescence time course with an exponential curve to account for bleaching. The estimated baseline was used to calculate the ΔF/F$_0$.

Simultaneous whole-cell recording and Voltron imaging in zebrafish: Experiments were performed on 6-day old progeny of a cross between Tg(10×UAS:Voltron) and TgBAC(slc17ab:LOXP-mCherry-LOXP-GAL4FF;vsx2: Cre). Fish were loaded with JF525 and then paralyzed as described above. After anesthetizing fish with MS-222, they were head-fixed and prepared for whole-cell recording and imaging of V2a hindbrain neurons. They were secured to a Sylgard-coated glass-bottom dish containing extracellular solution (134 mM NaCl, 2.9 mM KCl, 1.2 mM MgCl$_2$, 2.1 mM CaCl$_2$, 10 mM HEPES, and 10 mM glucose, adjusted to pH 7.8 with NaOH) with etched tungsten wires through the notochord. Then the head was rotated and secured ventral side up with etched tungsten pins placed through the ears and the rostral part of the jaw. The ventral surface of the hindbrain was carefully exposed by removing the notochord using an etched tungsten pin and fine forceps. Whole-cell recordings were guided based on fluorescence image and scanned Dodt gradient contrast image acquired with a custom two-photon microscope equipped with 40×0.8 NA objective lens (Nikon, MRD07420). Borosilicate glass pipettes (Sutter, BF150-86-15) were pulled by a micropipette puller (Sutter, P-1000) and filled with intracellular solution (125 mM potassium gluconate, 2.5 mM MgCl$_2$, 10 mM EGTA, 10 mM HEPES and 4 mM ATP-Na$_2$ adjusted to pH 7.3 with KOH). The resistance of the pipette was 5 to 7 MOhm. Recordings were made using the EPC 10 Quadro amplifier and PatchMaster (HEKA instruments). Voltron signal was acquired as described above but with 40x objective lens. After extracting Voltron signal from the patched cell using the procedure described above, the signal was further denoised using wden function in Wavelet Toolbox in MATLAB (Mathworks) to reveal Voltron signal corresponding to small subthreshold voltage changes.

Simultaneous Voltron imaging and whole-cell patch clamp in live adult flies: Experiments were performed on 2- to 10-day-old heterozygous progeny of a cross between UAS-IVS-syn21-Voltron-p10 and MB058B-Gal4 (52). The cross was kept on standard cornmeal food supplemented with all-trans-retinal (0.2 mM before eclosion and then 0.4 mM). Flies were head-fixed and prepared for imaging and electrophysiology as described previously (53). A small window was opened on the head cuticle, and fat cells and trachea that overlaid the target region were removed. The exposed brain was bathed in a drop (~200 μL) of dye-containing saline (1 μM for JF$_{549}$ and 5 μM for JF$_{525}$) for 1 hr. Saline contains (in mM): NaCl, 103; KCl, 3; CaCl$_2$, 1.5; MgCl$_2$, 4; NaHCO$_3$, 26; N-tris(hydroxymethyl) methyl-2-aminoethane-sulfonic acid, 5; NaH$_2$PO$_4$, 1; trehalose, 10; glucose, 10 (pH 7.3 when bubbled with 95% O2 and 5% CO$_2$, 275 mOsm. The brain was then washed with fresh saline several times, and maintained in the saline for 1 hr.

During the dye application and washout, animals were placed in a moist chamber to avoid dehydration. After that, they were moved to the imaging rig, where superfusion continued at 1-2 mL/min with oxygenated saline. To minimize movement during imaging, the proboscis was fixed with a UV-curable glue (NOA 68T, Norland products) and the frontal pulsatile organ muscle 16 was removed. Imaging was performed on a wide-field fluorescence microscope (SOM, Sutter Instruments) equipped with a 60×, NA 1.0, water-immersion objective (LUMPlanFI/IR; Olympus) and a sCMOS camera (Orca Flash 4.0 V2+, Hamamatsu). Images were acquired at 800 Hz with 4×4 binning through the Hamamatsu imaging software (HCImage Live). Data presented used $_{JF549}$. Illumination was provided by a 530 nm LED (SA-530, Sutter) with an excitation filter (FF01-543/22-25, Semrock); intensity at the sample plane was ~5 mW/mm$^2$ for axons and dendrites, and 8-16 mW/mm$^2$ for soma; emission was separated from excitation light using a dichroic mirror (FF562-Di03-25x36, Semrock) and an emission filter (LP02-568RU-25, Semrock).

Experiments with $JF_{525}$ tended to yield shorter duration imaging sessions (~2 min versus >5 min for $JF_{549}$ in dopamine neurons), likely because of greater phototoxicity with the shorter wavelength light. For $JF_{525}$, illumination was provided by a 506 nm LED (SA-506-1PLUS, Sutter) with an excitation filter (FF01-503/40-25, Semrock); intensity at the sample plane was typically 10-25 mW/mm$^2$; emission was separated from excitation light using a dichroic mirror (Di02-R532-25x36, Semrock) and an emission filter (FF01-562/40-25, Semrock).

Whole-cell recordings (54) were guided by Voltron fluorescence from target cells. The patch pipettes were pulled for a resistance of 5-7 MΩ and filled with pipette solution containing (in mM): L-potassium aspartate, 125; HEPES, 10; EGTA, 1.1; CaCl$_2$, 0.1; Mg-ATP, 4; Na-GTP, 0.5; biocytin hydrazide, 13; with pH adjusted to 7.3 with KOH (265 mOsm). Recordings were made using the Axon MultiClamp 700B amplifier (Molecular Devices). Cells were held at around −60 mV by injecting hyperpolarizing current (<50 pA). Signals were low-pass filtered at 5 kHz and digitized at 10 kHz.

Voltron data were analyzed in MATLAB. Regions of interest (ROIs) corresponding to different neuron compartments were manually selected, and the mean intensity of the ROI was extracted. Median filtering with a 50-ms time window was performed on the raw fluorescence traces to get a filtered trace, and F0 was calculated as the mean over the first 1 s of imaging session. For detecting action potential spikes and quantifying SNR, the filtered trace was subtracted from the raw trace. Spikes were detected by finding local minima with peak amplitude over 3.5 times the standard deviation of the entire subtracted trace, and SNR was quantified as peak amplitude over the standard deviation of the trace excluding the time zone (50 ms) containing spikes. To analyze the axon signals, the ROIs of ipsilateral and contralateral axons were first pooled together to detect spikes. The spikes were then assigned to either the patched cell or its sister cell depending on the relative peak amplitude, i.e. if ipsilateral/contralateral>1, spike is assigned to the patched cell, otherwise it is assigned to the sister cell.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. T. W. Chen et al., Ultrasensitive fluorescent proteins for imaging neuronal activity. Nature. 499, 295-300 (2013).
2. K. Svoboda, W. Denk, D. Kleinfeld, D. W. Tank, In vivo dendritic calcium dynamics in neocortical pyramidal neurons. Nature. 385, 161-165 (1997).
3. V. Emiliani, A. E. Cohen, K. Deisseroth, M. Hausser, All-optical interrogation of neural circuits. J. Neurosci. 35, 13917-13926 (2015).
4. Y. Xu, P. Zou, A. E. Cohen, Voltage imaging with genetically encoded indicators. Curr. Opin. Chem. Biol. 39, 1-10 (2017).
5. M. Z. Lin, M. J. Schnitzer, Genetically encoded indicators of neuronal activity. Nat. Neurosci. 19 (2016), pp. 1142-1153.
6. J. M. Kralj, A. D. Douglass, D. R. Hochbaum, D. Maclaurin, A. E. Cohen, Optical recording of action potentials in mammalian neurons using a microbial rhodopsin. Nat. Methods. 9, 90-95 (2011).
7. D. R. Hochbaum et al., All-optical electrophysiology in mammalian neurons using engineered microbial rhodopsins. Nat. Methods. 11, 825-833 (2014).
8. Y. Adam et al., All-optical electrophysiology reveals brain-state dependent changes in hippocampal subthreshold dynamics and excitability. bioRxiv (2018), doi:10.1101/281618.
9. L. Jin et al., Single action potentials and subthreshold electrical events imaged in neurons with a fluorescent protein voltage probe. Neuron. 75, 779-785 (2012).
10. P. Zou et al., Bright and fast multicoloured voltage reporters via electrochromic FRET. Nat. Commun. 5, 4625 (2014).
11. 4. Y. Gong et al., High-speed recording of neural spikes in awake mice and flies with a fluorescent voltage sensor. Science. 350, 1361-1366 (2015).
12. A. S. Abdelfattah et al., A bright and fast red fluorescent protein voltage indicator that reports neuronal activity in organotypic brain slices. J. Neurosci. 36, 2458-2472 (2016).
13. H. H. H. Yang et al., Subcellular Imaging of Voltage and Calcium Signals Reveals Neural Processing In Vivo. Cell. 166, 245-257 (2016).
14. J. B. Grimm et al., A general method to improve fluorophores for live-cell and single-molecule microscopy. Nat. Methods. 12, 244-250 (2015).
15. G. V. Los et al., HaloTag: A novel protein labeling technology for cell imaging and protein analysis. ACS Chem. Biol. 3, 373-382 (2008).
16. L. P. Encell et al., Development of a dehalogenase-based protein fusion tag capable of rapid, selective and covalent attachment to customizable ligands. Curr. Chem. Genomics. 6, 55-71 (2012).
17. J. B. Grimm et al., A general method to fine-tune fluorophores for live-cell and in vivo imaging. Nat. Methods. 14, 987 (2017).
18. Y. Gong, M. J. Wagner, J. Zhong Li, M. J. Schnitzer, Imaging neural spiking in brain tissue using FRET-opsin protein voltage sensors. Nat. Commun. 5, 3674 (2014).
19. J. M. Kralj, D. R. Hochbaum, A. D. Douglass, A. E. Cohen, Electrical spiking in Escherichia coli probed with a fluorescent voltage-indicating protein. Science (80-.). 333, 345-348 (2011).
20. T. Wada et al., Crystal structure of the eukaryotic light-driven proton-pumping rhodopsin, Acetabularia rhodopsin II, from marine alga. J. Mol. Biol. 411, 986-998 (2011).
21. A. Keppler et al., A general method for the covalent labeling of fusion proteins with small molecules in vivo. Nat. Biotechnol. 21, 86-89 (2003).

22. C. A. Baker, Y. M. Elyada, A. Parra, M. M. L. Bolton, Cellular resolution circuit mapping with temporal-focused excitation of soma-targeted channelrhodopsin. *Elife.* 5, 1-15 (2016).

23. S. T. Lim, D. E. Antonucci, R. H. Scannevin, J. S. Trimmer, A novel targeting signal for proximal clustering of the Kv2.1 K+channel in hippocampal neurons. *Neuron.* 25, 385-397 (2000).

24. S. L. Smith, I. T. Smith, T. Branco, M. Häusser, Dendritic spikes enhance stimulus selectivity in cortical neurons in vivo. *Nature.* 503, 115-120 (2013).

25. B. Tasic et al., Adult mouse cortical cell taxonomy revealed by single cell transcriptomics. *Nat. Neurosci.* 19, 335-346 (2016).

26. M. B. Ahrens et al., Brain-wide neuronal dynamics during motor adaptation in zebrafish. *Nature.* 485, 471-7 (2012).

27. T. Hige, Y. Aso, G. M. Rubin, G. C. Turner, Plasticity-driven individualization of olfactory coding in mushroom body output neurons. *Nature.* 526, 258-262 (2015).

28. A. Wang, J. Feng, Y. Li, P. Zou, Beyond fluorescent proteins: hybrid and bioluminescent indicators for imaging neural activities. *ACS Chem. Neurosci.* 9, 639-650 (2018).

29. L. A. Gross, G. S. Baird, R. C. Hoffman, K. K. Baldridge, R. Y. Tsien, The structure of the chromophore within DsRed, a red fluorescent protein from coral. *Proc. Natl. Acad. Sci.* 97, 11990-11995 (2000).

30. N. C. Shaner, P. A. Steinbach, R. Y. Tsien, A guide to choosing fluorescent proteins. *Nat. Methods.* 2, 905-909 (2005).

31. D. Wüstner, T. Christensen, L. M. Solanko, D. Sage, Photobleaching kinetics and time-integrated emission of fluorescent probes in cellular membranes. *Molecules.* 19, 11096-11130 (2014).

32. J. R. Lakowicz, *Principles of Fluorescence Spectroscopy* (Springer New York, New York, 2006).

33. S. J. Lord et al., DCDHF fluorophores for single-molecule imaging in cells. *ChemPhysChem.* 10, 55-65 (2009).

34. C. Eggeling, A. Volkmer, C. A. M. Seidel, Molecular photobleaching kinetics of Rhodamine 6G by one- and two-photon induced confocal fluorescence microscopy. *ChemPhysChem.* 6, 791-804 (2005).

35. T. J. Wardill et al., A Neuron-Based Screening Platform for Optimizing Genetically-Encoded Calcium Indicators. *PLoS One.* 8, 1-12 (2013).

36. D. A. Dombeck, C. D. Harvey, L. Tian, L. L. Looger, D. W. Tank, Functional imaging of hippocampal place cells at cellular resolution during virtual navigation. *Nat. Neurosci.* 13, 1433-1440 (2010).

37. T. Yardeni, M. Eckhaus, H. D. Morris, M. Huizing, S. Hoogstraten-Miller, Retro-orbital injections in mice. *Lab Anim. (NY).* 40, 155-160 (2011).

38. P. Thévenaz, U. E. Ruttimann, M. Unser, A pyramid approach to subpixel registration based on intensity. *IEEE Trans. Image Process.* 7, 27-41 (1998).

39. F. Franke, R. Quian Quiroga, A. Hierlemann, K. Obermayer, Bayes optimal template matching for spike sorting—combining fisher discriminant analysis with optimal filtering. *J. Comput. Neurosci.* 38, 439-459 (2015).

40. R. W. Köster, S. E. Fraser, Tracing Transgene Expression in Living Zebrafish Embryos. *Dev. Biol.* 233, 329-346 (2001).

41. R. M. White et al., Transparent Adult Zebrafish as a Tool for In Vivo Transplantation Analysis. *Cell Stem Cell.* 2, 183-189 (2008).

42. K. Kawakami et al., A transposon-mediated gene trap approach identifies developmentally regulated genes in zebrafish. *Dev. Cell.* 7, 133-44 (2004).

43. C. Satou et al., Transgenic tools to characterize neuronal properties of discrete populations of zebrafish neurons. *Development.* 140, 3927-31 (2013).

44. T. Kawashima et al., The Serotonergic System Tracks the Outcomes of Actions to Mediate Short-Term Motor Learning. *Cell.* 167, 933-946.e20 (2016).

45. N. Vladimirov et al., Light-sheet functional imaging in fictively behaving zebrafish. *Nat. Methods.* 11, 883-884 (2014).

46. N. Vladimirov et al., Light-sheet functional imaging in fictively behaving zebrafish. *Nat. Methods.* 11, 883-884 (2014).

47. B. K. Andrásfalvy et al., Quantum dot—based multiphoton fluorescent pipettes for targeted neuronal electrophysiology. *Nat. Methods.* 11, 1237-1241 (2014).

48. Y.-K. Bae et al., Anatomy of zebrafish cerebellum and screen for mutations affecting its development. *Dev. Biol.* 330, 406-26 (2009).

49. M. Takeuchi et al., Establishment of Gal4 transgenic zebrafish lines for analysis of development of cerebellar neural circuitry. *Dev. Biol.* 397, 1-17 (2015).

50. M. B. Ahrens et al., Brain-wide neuronal dynamics during motor adaptation in zebrafish. *Nature.* 485, 471-7 (2012).

51. M. Guizar-Sicairos, S. T. Thurman, J. R. Fienup, Efficient subpixel image registration algorithms. *Opt. Lett.* 33, 156 (2008).

52. Y. Aso et al., The neuronal architecture of the mushroom body provides a logic for associative learning. *Elife.* 3, e04577 (2014).

53. M. Murthy, G. Turner, Dissection of the head cuticle and sheath of living flies for whole-cell patch-clamp recordings in the brain. *Cold Spring Harb. Protoc.* 8, 134-139 (2013).

54. R. I. Wilson, G. C. Turner, G. Laurent, Transformation of Olfactory Drosophila Antennal Lobe. *Science (80-.).* 303, 366-370 (2004).

55. F. St-Pierre et al., High-fidelity optical reporting of neuronal electrical activity with an ultrafast fluorescent voltage sensor. *Nat. Neurosci.* 17, 884-889 (2014).

56. O. Randlett et al., Whole-brain activity mapping onto a zebrafish brain atlas. *Nat. Methods.* 12, 1039-1046 (2015).

57. S. Chamberland et al., Fast two-photon imaging of subcellular voltage dynamics in neuronal tissue with genetically encoded indicators. *Elife.* 6, e25690 (2017).

58. Govorunova, E. G., et al., Microbial Rhodopsins: Diversity, Mechanisms, and Optogenetic Applications. *Annu Rev Biochm.* 86, 845-872 (2017).

59. Beja, O., et al. Proteorhodopsin phototrophy in the ocean. *Nature* 411, 786-789 (2001)

60. U.S. Patent Application Publication NO. 2020/0123218 for "OPTOGENETIC PROBES FOR MEASURING MEMBRANE POTENTIAL."

61. U.S. Pat. Nos. 9,933,417, 10,018,624, 10,161,932, and 10,495,632.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of measuring voltage, the method comprising
(a) providing a voltage indicator, comprising:
  (i) a voltage-sensitive microbial rhodopsin domain comprising a polypeptide selected from a group consisting of QuarsAr1, QuarsAr2, Ace2N, and combinations thereof including one, two, three, or four amino acid mutations relative to a wild type polypeptide sequence; and
  (ii) a capture protein that covalently or noncovalently binds a fluorescent dye ligand that is a fluorescent protein; or
  a fluorescent dye, wherein the capture protein is provided together with the voltage-sensitive microbial rhodopsin domain in a fusion protein-;
(b) contacting the voltage indicator and the fluorescent dye ligand with a cell, and
(c) determining changes in fluorescence of the fluorescent dye ligand when the fluorescent dye ligand is captured by the voltage indicator.

2. The method of claim 1, wherein the cell is a neuron.

3. The method of claim 1, and further comprising observing changes in fluorescence with a microscope.

4. The method of claim 1, wherein the voltage indicator further comprises a linker between the voltage-sensitive domain and the capture protein.

5. The method of claim 1, further comprising modifying a length of a linker.

6. The method of claim 1, wherein an increase in membrane potential lead to an increase in fluorescence.

7. The method of claim 1, wherein the voltage-sensitive microbial rhodopsin domain comprises Ace2N.

8. The method of claim 7, wherein Ace2N includes an amino acid mutation at one or more of residue 81, 92, and 199.

9. The method of claim 1, wherein the capture protein is selected from a group consisting of biotin-avidin, a self-labeling protein tag, or a combination thereof.

10. The method of claim 1, wherein the capture protein is a self-labeling protein tag.

11. The method of claim 1, wherein 1, 2, 3, 4, 5, 6, 7, 8, 9, or 10 amino acids are removed from the junction between the rhodopsin domain and the capture protein.

12. The method of claim 1, and further comprising a targeting sequence.

13. The method of claim 12, wherein the targeting sequence is a soma targeting sequence.

14. The method of claim 12, wherein the capture protein is positioned at the c-terminal end of the voltage-sensitive microbial rhodopsin domain.

15. The method of claim 1, wherein the fluorescent dye ligand is an azetidine-containing fluorescent dye.

16. The method of claim 1, wherein the fluorescent dye ligand is a fluorescent protein.

17. A voltage indicator, comprising:
  a voltage-sensitive microbial rhodopsin domain comprising a polypeptide selected from the group consisting of QuarsAr1, QuarsAr2, Ace2N, and combinations thereof including one, two, three, or four amino acid mutations relative to a wild type polypeptide sequence; and
  a capture protein that covalently or noncovalently binds a fluorescent dye ligand that is
    a fluorescent protein; or
    a fluorescent dye, wherein the capture protein is provided together with the voltage-sensitive microbial rhodopsin domain in a fusion protein.

18. The voltage indicator of claim 17, wherein the voltage-sensitive microbial rhodopsin domain comprises Ace2N.

19. The voltage indicator of claim 17, wherein Ace2N includes an amino acid mutation at one or more of residue 81, 92, and 199.

20. The voltage indicator of claim 17, wherein the capture protein is a self-labeling protein tag.

* * * * *

SEQUENCE LISTING

```
Sequence total quantity: 40
SEQ ID NO: 1              moltype = DNA   length = 1659
FEATURE                   Location/Qualifiers
misc_feature              1..1659
                          note = Synthetic
source                    1..1659
                          mol_type = other DNA
                          organism = synthetic construct
SEQUENCE: 1
atggctgacg tggaaaccga gaccggcatg attgcacagt ggattgtctt tgctattatg    60
gctgctgctg ctattgcttt tggagtggct gtgcactttc ggccttcaga gctgaagagc   120
gcatactata tcaacattgc catctgcact atcgccgcta ccgcttacta tgcaatggcc   180
gtgaactacc aggacctgac aatgaatggt gaaaggcagg tggtctacgc aagatatatt   240
aactgggtgc tgaccacacc actgctcctg ctcaacctca tcgtcatgac caagatgggc   300
ggagtgatga tttcttgggt catcggcgca gacattttca tgatcgtgtt tggtattctg   360
ggcgccttcg aggatgaaca caagttcaaa tgggtgtact tatcgctgg atgtgtgatg   420
caggcagtcc tgcatacggg gatgtataac gccacttgga aagacgatct gaagaaaagc   480
cccgagtacc atagctccta tgtcagtctg ctcgtcttcc tgtcaatcct ctgggtgttt   540
tatcctgtcg tgtgggcttt cgggtctggt agtggcgtgc tgtccgtcga caatgaggcc   600
attctcatgg gaatcctgga tgtgctcgct aagccactgt ttggaatggg gtgcctcatt   660
gcccatgaga ctatcttcaa gatcggtact ggctttccat cgaccccca ttatgtggaa    720
gtcctgggcg agcgcatgca ctacgtcgat gttggtccgc gcgatggcac ccctgtgctg   780
ttcctgcacg gtaacccgac ctcctcctac gtgtggcgca acatcatccc gcatgttgca   840
ccgacccatc gctgcattgc tccagacctg atcggtatgg gcaaatccga caaaccagac   900
ctgggttatt tcttcgacga ccacgtccgc ttcatggatg ccttcatcga agccctgggt   960
ctggaagagg tcgtcctggt cattcacgac tggggctccg ctctgggttt ccactgggcc  1020
aagcgcaatc cagagcgcgt caaaggtatt gcatttatgg agttcatccg ccctatcccg  1080
acctggacg aatggccaga atttgcccgc gagaccttcc aggccttccg caccaccgac  1140
gtcggccgca agctgatcat cgatcagaac gtttttatcg agggtacgct gccgatgggt  1200
gtcgtccgcc cgctgactga agtcgagatg gaccattacc gcgagccgtt cctgaatcct  1260
gttgaccgcg agccactgtg gcgcttccca aacgagctgc caatcgccgg tgagccagcg  1320
aacatcgtcg cgctggtcga agaatacatg gactggctgc accagtcccc tgtcccgaag  1380
ctgctgttct ggggcacccc aggcgttctg atcccaccgg ccgaagccgc tcgcctggcc  1440
aaaagcctgc ctaactgcaa ggctgtggac atcggcccgg tctgaatct gctgcaagaa  1500
gacaaccccg aacctgatcg gcagcgagatc gcgcgctggc tgtcgacgct cgagatttcc  1560
ggcgagccaa ccactaagag caggatcacc agcgagggcg agtacatccc cctggaccag  1620
atcgacatca acgtgttctg ctacgagaac gaggtgtaa                         1659

SEQ ID NO: 2              moltype = AA    length = 552
FEATURE                   Location/Qualifiers
REGION                    1..552
                          note = Synthetic
source                    1..552
                          mol_type = protein
                          organism = synthetic construct
SEQUENCE: 2
MADVETETGM IAQWIVFAIM AAAAIAFGVA VHFRPSELKS AYYINIAICT IAATAYYAMA    60
VNYQDLTMNG ERQVVYARYI NWVLTTPLLL LNLIVMTKMG GVMISWVIGA DIFMIVFGIL   120
GAFEDEHKFK WVYFIAGCVM QAVLTYGMYN ATWKDDLKKS PEYHSSYVSL LVFLSILWVF   180
YPVVWAFGSG SGVLSVDNEA ILMGILDVLA KPLFGMGCLI AHETIFKIGT GFPFDPHYVE   240
VLGERMHYVD VGPRDGTPVL FLHGNPTSSY VWRNIIPHVA PTHRCIAPDL IGMGKSDKPD   300
LGYFFDDHVR FMDAFIEALG LEEVVLVIHD WGSALGFHWA KRNPERVKGI AFMEFIRPIP   360
TWDEWPEFAR ETFQAFRTTD VGRKLIIDQN VFIEGTLPMG VVRPLTEVEM DHYREPFLNP   420
VDREPLWRFP NELPIAGEPA NIVALVEEYM DWLHQSPVPK LLFWGTPGVL IPPAEAARLA   480
KSLPNCKAVD IGPGLNLLQE DNPDLIGSEI ARWLSTLEIS GEPTTKSRIT SEGEYIPLDQ   540
IDINVFCYEN EV                                                      552

SEQ ID NO: 3              moltype = DNA   length = 1659
FEATURE                   Location/Qualifiers
misc_feature              1..1659
                          note = Synthetic
source                    1..1659
                          mol_type = other DNA
                          organism = synthetic construct
SEQUENCE: 3
atggctgacg tggaaaccga gaccggcatg attgcacagt ggattgtctt tgctattatg    60
gctgctgctg ctattgcttt tggagtggct gtgcactttc ggccttcaga gctgaagagc   120
gcatactata tcaacattgc catctgcact atcgccgcta ccgcttacta tgcaatggcc   180
gtgaactacc aggacctgac aatgaatggt gaaaggcagg tggtctacgc aagatatatt   240
gactgggtgc tgaccacacc actgctcctg ctcaacctca tcgtcatgac caagatgggc   300
ggagtgatga tttcttgggt catcggcgca gacattttca tgatcgtgtt tggtattctg   360
ggcgccttcg aggatgaaca caagttcaaa tgggtgtact tatcgctgg atgtgtgatg   420
caggcagtcc tgcatacggg gatgtataac gccacttgga aagacgatct gaagaaaagc   480
cccgagtacc atagctccta tgtcagtctg ctcgtcttcc tgtcaatcct ctgggtgttt   540
tatcctgtcg tgtgggcttt cgggtctggt agtggcgtgc tgtccgtcga caatgaggcc   600
attctcatgg gaatcctgga tgtgctcgct aagccactgt ttggaatggg gtgcctcatt   660
gcccatgaga ctatcttcaa gatcggtact ggctttccat cgaccccca ttatgtggaa    720
gtcctgggcg agcgcatgca ctacgtcgat gttggtccgc gcgatggcac ccctgtgctg   780
```

```
ttcctgcacg gtaacccgac ctcctcctac gtgtggcgca acatcatccc gcatgttgca    840
ccgacccatc gctgcattgc tccagacctg atcggtatgg gcaaatccga caaaccagac    900
ctgggttatt tcttcgacga ccacgtccgc ttcatggatg ccttcatcga agccctgggt    960
ctggaagagg tcgtcctggt cattcacgac tggggctccg ctctgggttt ccactgggca   1020
aagcgcaatc cagagcgcgt caaaggtatt gcatttatgg agttcatccg ccctatcccg   1080
acctgggacg aatggccaga atttgcccgc gagaccttcc aggccttccg caccaccgac   1140
gtcggccgca agctgatcat cgatcagaac gtttttatcg agggtacgct gccgatgggt   1200
gtcgtccgcc cgctgactga agtcgagatg gaccattacc gcgagccgtt cctgaatcct   1260
gttgaccgcg agccactgtg gcgcttccca aacgagctgc caatcgcggg tgagccagcg   1320
aacatcgtcg cgctggtcga agaatacatg gactggctgc accagtcccc tgtcccgaag   1380
ctgctgttct ggggcacccc aggcgttctg atcccaccgg ccgaagccgc tcgcctggcc   1440
aaaagcctgc ctaactgcaa ggctgtggac atcggcccgg gtctgaatct gctgcaagaa   1500
gacaacccgg acctgatcgg cagcgagatc gcgcgctggc tgtcgacgct cgagatttcc   1560
ggcgagccaa ccactaagag caggatcacc agcgagggcg agtacatccc cctggaccag   1620
atcgacatca acgtgttctg ctacgagaac gaggtgtaa                          1659

SEQ ID NO: 4           moltype = AA  length = 552
FEATURE                Location/Qualifiers
REGION                 1..552
                       note = Synthetic
source                 1..552
                       mol_type = protein
                       organism = synthetic construct
SEQUENCE: 4
MADVETETGM IAQWIVFAIM AAAAIAFGVA VHFRPSELKS AYYINIAICT IAATAYYAMA    60
VNYQDLTMNG ERQVVYARYI DWVLTTPLLL LNLIVMTKMG GVMISWVIGA DIFMIVFGIL   120
GAFEDEHKFK WVYFIAGCVM QAVLTYGMYN ATWKDDLKKS PEYHSSYVSL LVFLSILWVF   180
YPVVWAFGSG SGVLSVDNEA ILMGILDVLA KPLFGMGCLI AHETIFKIGT GPFDPHYVE    240
VLGERMHYVD VGPRDGTPVL FLHGNPTSSY VWRNIIPHVA PTHRCIAPDL IGMGKSDKPD   300
LGYFFDDHVR FMDAFIEALG LEEVVLVIHD WGSALGFHWA KRNPERVKGI APMEFIRPIP   360
TWDEWPEFAR ETFQAFRTTD VGRKLIIDQN VFIEGTLPMG VVRPLTEVEM DHYREPFLNP   420
VDREPLWRFP NELPIAGEPA NIVALVEEYM DWLHQSPVPK LLFWGTPGVL IPPAEAARLA   480
KSLPNCKAVD IGPGLNLLQE DNPDLIGSEI ARWLSTLEIS GEPTTKSRIT SEGEYIPLDQ   540
IDINVFCYEN EV                                                       552

SEQ ID NO: 5           moltype = DNA  length = 1659
FEATURE                Location/Qualifiers
misc_feature           1..1659
                       note = Synthetic
source                 1..1659
                       mol_type = other DNA
                       organism = synthetic construct
SEQUENCE: 5
atggctgacg tggaaaccga gaccggcatg attgcacagt ggattgtctt tgctattatg     60
gctgctgctg ctattgcttt tggagtggct gtgcactttc ggccttcaga gctgaagagc   120
gcatactata tcaacattgc catctgcact atcgccgcta ccgcttacta tgcaatggcc   180
gtgaactacc aggacctgac aatgaatggt gaaaggcagg tggtctacgc aagatatatt   240
gactgggtgc tgaccacacc actgctcctg ctcaacctca tcgtcatgac caagatgggc   300
ggagtgatga tttcttgggt catcggcgca gacattttca tgatcgtgtt tggtattctg   360
ggcgccttcg aggatgaaca caagttcaaa tgggtgtact tatcgctgg atgtgtgatg   420
caggcagtcc tgacatacgg gatgtataac gccacttgga aagcgatct gaagaaaagc   480
cccgagtacc atagctccta tgtcagtctg ctcgtcttcc tgtcaatcct ctgggtgttt   540
tatcctgtcg tgtgggcttt cgggtctggt agtggcgtgc tgtccgtcga caatgtggcc   600
attctcatgg gaatcctgga tgtgctcgct aagccactgt ttggaatggg gtgcctcatt   660
gcccatgaga ctatcttcaa gatcggtact ggctttcat tcgaccccca ttatgtggaa   720
gtcctgggcg agcgcatgca ctacgtcgat gttggtccgc gcgatggcac ccctgtgctg   780
ttcctgcacg gtaacccgac ctcctcctac gtgtggcgca acatcatccc gcatgttgca   840
ccgacccatc gctgcattgc tccagacctg atcggtatgg gcaaatccga caaaccagac   900
ctgggttatt tcttcgacga ccacgtccgc ttcatggatg ccttcatcga agccctgggt   960
ctggaagagg tcgtcctggt cattcacgac tggggctccg ctctgggttt ccactgggca  1020
aagcgcaatc cagagcgcgt caaaggtatt gcatttatgg agttcatccg ccctatcccg  1080
acctgggacg aatggccaga atttgcccgc gagaccttcc aggccttccg caccaccgac  1140
gtcggccgca agctgatcat cgatcagaac gtttttatcg agggtacgct gccgatgggt  1200
gtcgtccgcc cgctgactga agtcgagatg gaccattacc gcgagccgtt cctgaatcct  1260
gttgaccgcg agccactgtg gcgcttccca aacgagctgc caatcgcggg tgagccagcg  1320
aacatcgtcg cgctggtcga agaatacatg gactggctgc accagtcccc tgtcccgaag  1380
ctgctgttct ggggcacccc aggcgttctg atcccaccgg ccgaagccgc tcgcctggcc  1440
aaaagcctgc ctaactgcaa ggctgtggac atcggcccgg gtctgaatct gctgcaagaa  1500
gacaacccgg acctgatcgg cagcgagatc gcgcgctggc tgtcgacgct cgagatttcc  1560
ggcgagccaa ccactaagag caggatcacc agcgagggcg agtacatccc cctggaccag  1620
atcgacatca acgtgttctg ctacgagaac gaggtgtaa                         1659

SEQ ID NO: 6           moltype = AA  length = 552
FEATURE                Location/Qualifiers
REGION                 1..552
                       note = Synthetic
source                 1..552
                       mol_type = protein
                       organism = synthetic construct
```

```
SEQUENCE: 6
MADVETETGM IAQWIVFAIM AAAAIAFGVA VHFRPSELKS AYYINIAICT IAATAYYAMA      60
VNYQDLTMNG ERQVVYARYI DWVLTTPLLL LNLIVMTKMG GVMISWVIGA DIFMIVFGIL     120
GAFEDEHKFK WVYFIAGCVM QAVLTYGMYN ATWKDDLKKS PEYHSSYVSL LVFLSILWVF     180
YPVVWAFGSG SGVLSVDNVA ILMGILDVLA KPLFGMGCLI AHETIFKIGT GPFDPHYVE      240
VLGERMHYVD VGPRDGTPVL FLHGNPTSSY VWRNIIPHVA PTHRCIAPDL IGMGKSDKPD     300
LGYFFDDHVR FMDAFIEALG LEEVVLVIHD WGSALGFHWA KRNPERVKGI AFMEFIRPIP     360
TWDEWPEFAR ETFQAFRTTD VGRKLIIDQN VFIEGTLPMG VVRPLTEVEM DHYREPFLNP     420
VDREPLWRFP NELPIAGEPA NIVALVEEYM DWLHQSPVPK LLFWGTPGVL IPPAEAARLA     480
KSLPNCKAVD IGPGLNLLQE DNPDLIGSEI ARWLSTLEIS GEPTTKSRIT SEGEYIPLDQ     540
IDINVFCYEN EV                                                         552

SEQ ID NO: 7            moltype = DNA   length = 1452
FEATURE                 Location/Qualifiers
misc_feature            1..1452
                        note = Synthetic
source                  1..1452
                        mol_type = other DNA
                        organism = synthetic construct
SEQUENCE: 7
atggctgacg tggaaaccga gaccggcatg attgcacagt ggattgtctt tgctattatg      60
gctgctgctg ctattgcttt tggagtggct gtgcacttc ggcttcaga gctgaagagc      120
gcatactata tcaacattgc catctgcact atcgccgcta ccgcttacta caatggcc       180
gtgaactacc aggacctgac aatgaatggt gaaaggcagg tggtctacgc aagatatatt    240
gactgggtgc tgaccacacc actgctcctg ctcaacctca tcgtcatgac caagatgggc    300
ggagtgatga tttcttgggt catcggcgca gacattttca tgatcgtgtt tggtattctg    360
ggcgccttcg aggatgaaca caagttcaaa tgggtgtact ttatcgctgg atgtgtgatg    420
caggcagtcc tgacatacgg gatgtataac gccacttgga agacgatct gaagaaaagc     480
cccgagtacc atagctccta tgtcagtctg ctcgtcttcc tgtcaatcct ctgggtgttt    540
tatcctgtc tgtgggcttt cgggtctggt agtggcgtgc tgtccgtcga caatgaggcc    600
attctcatgg gaatcctgga tgtgctcgct aagccactgt ttggaatggg gtgcctcatt    660
gcccatgaga ctatcttcaa gaagatgctg aggtctctcc cagcgacaca tgagttacac    720
atctttggct ccatcaacgg tgtggacttt gacatggtgg tcagggcac ggcaatcca     780
aatgatggtt atgaggagtt aaacctgaag tccaccaagg tgacctcac gttctcccca     840
tggattctgg tccctcatat cgggtatggc ttccatcagt acctgcccta ccctgacgug    900
atgtcgcctt tccaggccgc catggtagat ggctccggat accaagtcca tcgcacaatg    960
cagtttgaag atggtgcctc ccttactgtt aactaccgct acacctacga gggaagccac   1020
atcaaaggag aggcccaggt gaaggggact ggtttcccctg ctgacggtcc tgtgatgacc   1080
aactctacga ccgctgcgga ctggtgcagg tcgaagaaga cttaccccaa cgacaaaacc   1140
atcatcagta cctttaagtg gagttacacc actggaaatg gcaagcgcta caggagcact   1200
gcgcggacca cctacacctt tgccaagcca atggcggcta actatctgaa gaaccagccg   1260
atgtacgtgt tccgtaagac ggagctcaag cactccaaga ccgagctcaa cttcaaggag   1320
tggcaaaagg cctttaccga tgtgatgggc atggacgagc tgtacaagaa gagcaggatc   1380
accagcgagg gcgagtacat ccccctggac cagatcgaca tcaacgtgtt ctgctacgag   1440
aacgaggtgt aa                                                        1452

SEQ ID NO: 8            moltype = AA   length = 483
FEATURE                 Location/Qualifiers
REGION                  1..483
                        note = Synthetic
source                  1..483
                        mol_type = protein
                        organism = synthetic construct
SEQUENCE: 8
MADVETETGM IAQWIVFAIM AAAAIAFGVA VHFRPSELKS AYYINIAICT IAATAYYAMA      60
VNYQDLTMNG ERQVVYARYI DWVLTTPLLL LNLIVMTKMG GVMISWVIGA DIFMIVFGIL     120
GAFEDEHKFK WVYFIAGCVM QAVLTYGMYN ATWKDDLKKS PEYHSSYVSL LVFLSILWVF     180
YPVVWAFGSG SGVLSVDNEA ILMGILDVLA KPLFGMGCLI AHETIFKKML RSLPATHELH    240
IFGSINGVDF DMVGQGTGNP NDGYEELNLK STKGDLQFSP WILVPHIGYG FHQYLPYPDG    300
MSPFQAAMVD GSGYQVHRTM QFEDGASLTV NYRYTYEGSH IKGEAQVKGT GFPADGPVMT    360
NSLTAADWCR SKKTYPNDKT IISTFKWSYT TGNGKRYRST ARTTYTFAKP MAANYLKNQP    420
MYVFRKTELK HSKTELNFKE WQKAFTDVMG MDELYKKSRI TSEGEYIPLD QIDINVFCYE    480
NEV                                                                   483

SEQ ID NO: 9            moltype = AA   length = 227
FEATURE                 Location/Qualifiers
REGION                  1..227
                        note = Synthetic
source                  1..227
                        mol_type = protein
                        organism = synthetic construct
SEQUENCE: 9
MADVETETGM IAQWIVFAIM AAAAIAFGVA VHFRPSELKS AYYINIAICT IAATAYYAMA      60
VNYQDLTMNG ERQVVYARYI NWVLTTPLLL LDLIVMTKMG GVMISWVIGA DIFMIVFGIL     120
GAFEDEHKFK WVYFIAGCVM QAVLTYGMYN ATWKDDLKKS PEYHSSYVSL LVFLSILWVF     180
YPVVWAFGSG SGVLSVDNEA ILMGILDVLA KPLFGMGCLI AHETIFK                   227

SEQ ID NO: 10           moltype = AA   length = 298
FEATURE                 Location/Qualifiers
```

```
REGION                          1..298
                                note = Synthetic
source                          1..298
                                mol_type = protein
                                organism = synthetic construct
SEQUENCE: 10
IGTGFPFDPH YVEVLGERMH YVDVGPRDGT PVLFLHGNPT SSYVWRNIIP HVAPTHRCIA     60
PDLIGMGKSD KPDLGYFFDD HVRFMDAFIE ALGLEEVVLV IHDWGSALGF HWAKRNPERV    120
KGIAFMEFIR PIPTWDEWPE FARETFQAFR TTDVGRKLII DQNVFIEGTL PMGVVRPLTE    180
VEMDHYREPF LNPVDREPLW RFPNELPIAG EPANIVALVE EYMDWLHQSP VPKLLFWGTP    240
GVLIPPAEAA RLAKSLPNCK AVDIGPGLNL LQEDNPDLIG SEIARWLSTL EISGEPTT      298

SEQ ID NO: 11                   moltype = AA   length = 229
FEATURE                         Location/Qualifiers
REGION                          1..229
                                note = Synthetic
source                          1..229
                                mol_type = protein
                                organism = synthetic construct
SEQUENCE: 11
KMLRSLPATH ELHIFGSING VDFDMVGQGT GNPNDGYEEL NLKSTKGDLQ FSPWILVPHI     60
GYGFHQYLPY PDGMSPFQAA MVDGSGYQVH RTMQFEDGAS LTVNYRYTYE GSHIKGEAQV   120
KGTGFPADGP VMTNSLTAAD WCRSKKTYPN DKTIISTFKW SYTTGNGKRY RSTARTTYTF   180
AKPMAANYLK NQPMYVFRKT ELKHSKTELN FKEWQKAFTD VMGMDELYK                229

SEQ ID NO: 12                   moltype = AA   length = 27
FEATURE                         Location/Qualifiers
REGION                          1..27
                                note = Synthetic
source                          1..27
                                mol_type = protein
                                organism = synthetic construct
SEQUENCE: 12
KSRITSEGEY IPLDQIDINV FCYENEV                                        27

SEQ ID NO: 13                   moltype = AA   length = 7
FEATURE                         Location/Qualifiers
REGION                          1..7
                                note = Synthetic
source                          1..7
                                mol_type = protein
                                organism = synthetic construct
SEQUENCE: 13
FCYENEV                                                              7

SEQ ID NO: 14                   moltype = AA   length = 65
FEATURE                         Location/Qualifiers
REGION                          1..65
                                note = Synthetic
source                          1..65
                                mol_type = protein
                                organism = synthetic construct
SEQUENCE: 14
QSQPILNTKE MAPQSKPPEE LEMSSMPSPV APLPARTEGV IDMRSMSSID SFISCATDFP    60
EATRF                                                                65

SEQ ID NO: 15                   moltype = AA   length = 254
FEATURE                         Location/Qualifiers
REGION                          1..254
                                note = Synthetic
source                          1..254
                                mol_type = protein
                                organism = synthetic construct
SEQUENCE: 15
IALQAGYDLL GDGRPETLWL GIGTLLMLIG TFYFLVRGWG VTDKDAREYY AVTILVSGIA    60
SAAYLSMFFG IGLTEVSVGG EMLDIYYARY AHWLFTTLLL LHLALLAKVD RVTIGTLVGV   120
DALMIVTGLI GALSHTAIAR YSWWLFSTIC MIVVLYVLAT SLRSAAKERG PEVASTFNTL   180
TALVLVLWTA YPILWIIGTE GAGVVGLGIE TLLFMVLDVT AKVGFGFILL RSRAILGDTE   240
APEPSAGADV SAAD                                                      254

SEQ ID NO: 16                   moltype = AA   length = 255
FEATURE                         Location/Qualifiers
REGION                          1..255
                                note = Synthetic
source                          1..255
                                mol_type = protein
                                organism = synthetic construct
SEQUENCE: 16
IALQAGYDLL GDGRPETLWL GIGTLLMLIG TFYFLVRGWG VTDKDAREYY AVTILVSGIA    60
```

```
SAAYLSMFFG IGLTEVSVGG EMLDIYYARY AQWLFTTPLL LLHLALLAKV DRVTIGTLVG    120
VDALMIVTGL IGALSHTAIA RYSWWLFSTI CMIVVLYVLA TSLRSAAKER GPEVASTFNT    180
LTALVLVLWT AYPILWIIGT EGAGVVGLGI ETLLFMVLDV TAKVGFGFIL LRSRAILGDT    240
EAPEPSAGAD VSAAD                                                    255

SEQ ID NO: 17              moltype = AA   length = 241
FEATURE                    Location/Qualifiers
REGION                     1..241
                           note = Synthetic
source                     1..241
                           mol_type = protein
                           organism = synthetic construct
SEQUENCE: 17
IALQAGYDLL GDGRPETLWL GIGTLLMLIG TFYFLVRGWG VTDKDAREYY AVTILVSGIA     60
SAAYLSMFFG IGLTEVSVGG EMLDIYYARY AQWLFTTPLL LLHLALLAKV DRVTIGTLVG    120
VDALMIVTGL IGALSHTAIA RYSWWLFSTI CMIVVLYVLA TSLRSAAKER GPEVASTFNT    180
LTALVLVLWT AYPILWIIGT EGAGVVGLGI ETLLFMVLDV TAKVGFGFIL LRSRAILGDT    240
E                                                                   241

SEQ ID NO: 18              moltype = AA   length = 181
FEATURE                    Location/Qualifiers
REGION                     1..181
                           note = Synthetic
source                     1..181
                           mol_type = protein
                           organism = synthetic construct
SEQUENCE: 18
DKDCEMKRTT LDSPLGKLEL SGCEQGLHRI IFLGKGTSAA DAVEVPAPAA VLGGPEPLMQ     60
ATAWLNAYFH QPEAIEEFPV PALHHPVFQQ ESFTRQVLWK LLKVVKFGEV ISYSHLAALA    120
GNPAATAAVK TALSGNPVPI LIPCHRVVQG DLDVGGYEGG LAVKEWLLAH EGHRLGKPGL    180
G                                                                   181

SEQ ID NO: 19              moltype = DNA   length = 1854
FEATURE                    Location/Qualifiers
misc_feature               1..1854
                           note = Synthetic
source                     1..1854
                           mol_type = other DNA
                           organism = synthetic construct
SEQUENCE: 19
atggctgacg tggaaaccga gaccggcatg attgcacagt ggattgtctt tgctattatg     60
gctgctgctg ctattgcttt tggagtggct gtgcactttc ggccttcaga gctgaagagc    120
gcatactata tcaacattgc catctgcact atcgccgcta ccgcttacta tgcaatggcc    180
gtgaactacc aggacctgac aatgaatggt gaaaggcagg tggtctacgc aagatatatt    240
aactgggtgc tgaccacacc actgctcctg ctcgatctca tcgtcatgac caagatgggc    300
ggagtgatga tttcttgggt catcggcgca gacattttca tgatcgtgtt tggtattctg    360
ggcgccttcg aggatgaaca caagttcaaa tgggtgtact ttatcgctgg atgtgtgatg    420
caggcagtcc tgacatacgg gatgtataac gccacttgga aagacgatct gaagaaaagc    480
cccgagtacc atagctccta tgtcagtctg ctcgtcttcc tgtcaatcct ctgggtgttt    540
tatcctgtcg tgtgggcttt cgggtctggt agtggcgtgc tgtccgtcga caatgaggcc    600
attctcatgg aatcctgga tgtgctcgct aagccactgt ttggaatggg gtgcctcatt    660
gcccatgaga ctatcttcaa gatcggtact ggctttccat tcgaccccca ttatgtggaa    720
gtcctgggcg agcgcatgca ctacgtcgat gttggtccgc gcgatggcac ccctgtgctg    780
ttcctgcacg gtaacccgac ctcctcctac gtgtggcgca acatcatccc gcatgttgca    840
ccgacccatc gctgcattgc tccagacctg atcggtatgg gcaaatccag caaaccagac    900
ctgggttatt tcttcgacga ccacgtccgc ttcatggatg ccttcatcga agccctgggt    960
ctggaagagg tcgtcctggt cattcacgac tgggctccg ctctgggttt ccactgggcc   1020
aagcgcaatc cagagcgcgt caaaggtatt gcatttatgg agttcatccg ccctatcccg   1080
acctgggacg aatggccaga atttgcccgc gagaccttcc aggccttccg caccaccgac   1140
gtcggccgca agctgatcat cgatcagaac gtttttatcg agggtacgcc gccgatgggt   1200
gtcgtccgcc cgctgactga agtcgagatg gaccattacc gcgagccgtt cctgaatcct   1260
gttgaccgcg agccactgtg gcgcttccca aacgagctgc caatcgccgg tgagccagcg   1320
aacatcgtcg cgctggtcga agaatacatg gactggctgc caccagtcccc tgtcccgaag   1380
ctgctgttct gggggacccc aggcgttctg atcccaccgg ccgaagccgg tctgctggcc   1440
aaaagcctgc taactgcaa ggctgtggac atcggcccgg tctgaatct gctgcaagaa    1500
gacaacccgg acctgatcgg cagcgagatc gcgcgctggc tgtcgacgct cgagatttcc   1560
ggcgagccaa ccactaagag caggatcacc agcgagggcg agtacatccc cctggaccag   1620
atcgacatca acgtgttctg ctacgagaac gaggtgcaaa gtcagcctat cctgaacaca   1680
aaggaaatgg ctccacagtc taagcctccc gaagagcttg agatgtccag tatgccaagt   1740
cccgtggctc ccctcctgc caggactgaa ggagtgattg acatgaggag tatgtcatct   1800
attgatagct tcatctcttg cgcaacagat ttccccgagg ctactcgatt ctaa         1854

SEQ ID NO: 20              moltype = AA   length = 617
FEATURE                    Location/Qualifiers
REGION                     1..617
                           note = Synthetic
source                     1..617
                           mol_type = protein
                           organism = synthetic construct
```

SEQUENCE: 20
```
MADVETETGM IAQWIVFAIM AAAAIAFGVA VHFRPSELKS AYYINIAICT IAATAYYAMA    60
VNYQDLTMNG ERQVVYARYI NWVLTTPLLL LDLIVMTKMG GVMISWVIGA DIFMIVFGIL   120
GAFEDEHKFK WVYFIAGCVM QAVLTYGMYN ATWKDDLKKS PEYHSSYVSL LVFLSILWVF   180
YPVVWAFGSG SGVLSVDNEA ILMGILDVLA KPLFGMGCLI AHETIFKIGT GPFFDPHYVE   240
VLGERMHYVD VGPRDGTPVL FLHGNPTSSY VWRNIIPHVA PTHRCIAPDL IGMGKSDKPD   300
LGYFFDDHVR FMDAFIEALG LEEVVLVIHD WGSALGFHWA KRNPERVKGI AFMEFIRPIP   360
TWDEWPEFAR ETFQAFRTTD VGRKLIIDQN VFIEGTLPMG VVRPLTEVEM DHYREPFLNP   420
VDREPLWRFP NELPIAGEPA NIVALVEEYM DWLHQSPVPK LLFWGTPGVL IPPAEAARLA   480
KSLPNCKAVD IGPGLNLLQE DNPDLIGSEI ARWLSTLEIS GEPTTKSRIT SEGEYIPLDQ   540
IDINVFCYEN EVQSQPILNT KEMAPQSKPP EELEMSSMPS PVAPLPARTE GVIDMRSMSS   600
IDSFISCATD FPEATRF                                                 617
```

```
SEQ ID NO: 21           moltype = DNA   length = 1767
FEATURE                 Location/Qualifiers
misc_feature            1..1767
                        note = Synthetic
source                  1..1767
                        mol_type = other DNA
                        organism = Synthetic construct
```
SEQUENCE: 21
```
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg gaatattacg ctgtgactat cctggtgtcc   180
ggaatcgcat ccgccgcata tctgtctatg ttctttggta tcgggcttac tgaggtgtcc   240
gtcgggtccg aaatgttgga tatctattat gccaggtacg cccagtggct gtttaccacc   300
ccacttctgc tgctgcacct ggcccttctc gctaaggtgg atcgggtgac catcggcacc   360
ctggtgggtg tggacgccct gatgatcgtc actggcctca tcgcaggcct gagccacacg   420
gccatagcca gatacagttg gtggttgttc tctacaattt gcatgatagt ggtgctctat   480
gttctggcta catccctgcg atctgctgca aaggagcggg gccccgaggt ggcatcctcc   540
tttaacaccc tgacagctct ggtcttggtg ctgtggaccg cttaccctat cctgtggatc   600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcgacaccg aggcaccaga acccagtgcc ggtgccgatg tcagtgccgc cgacatggcg   780
gaaatcggta ctggctttcc attcgacccc cattatgtgg aagtcctggg cgagcgcatg   840
cactacgtcg atgttggtcc gcgcgatggc acccctgtgc tgttcctgca cggtaacccg   900
acctcctcct acgtgtggcg caacatcatc ccgcatgttg caccgaccca tcgctgcatt   960
gctccagacc tgatcggtat gggcaaatcc gacaaaccag acctgggtta tttcttcgac  1020
gaccacgtcc gcttcatgga tgccttcatc gaagccctgg gtctggaaga ggtcgtcctg  1080
gtcattcacg actggggctc cgctctgggt ttccactggg ccaagcgcaa tccagagcgc  1140
gtcaaaggta ttgcatttat ggagttcatc cgccctatcc cgacctggga cgaatggcca  1200
gaatttgccc gcgagacctt ccaggccttc cgcaccaccg acgtcggccg caagctgatc  1260
atcgatcaga acgttttat cgaggtacg ctgccgatgg gtcgtcctg cccgctgact  1320
gaagtcgaga tggaccatta ccgcgagccg ttcctgaatc ctgttgaccg cgagccactg  1380
tggcgcttcc caaacgagct gccaatcgcc ggtgagccag cgaacatcgt cgcgctggtc  1440
gaagaataca tggactggct gcaccagtcc cctgtcccga gctgctgtt ctggggcacc  1500
ccaggcgttc tgatccccac cggccgaagc gctcgcctgg ccaaaagcct gcctaactgc  1560
aaggctgtgg acatcggccc gggtctgaat ctgctgcaag aagacaaccc ggacctgatc  1620
ggcagcgaga tcgcgcgctg gctgtcgacg ctcgagattc ccggcgagcc aaccactaag  1680
agtagaatca caagcgaagg cgagtacatc ccctggatc aaatagacat aaatgtaggt  1740
ggattttgtt atgagaatga agtataa                                     1767
```

```
SEQ ID NO: 22           moltype = AA   length = 588
FEATURE                 Location/Qualifiers
REGION                  1..588
                        note = Synthetic
source                  1..588
                        mol_type = protein
                        organism = synthetic construct
```
SEQUENCE: 22
```
MVSIALQAGY DLLGDRPET LWLGIGTLLM LIGTFYFLVR GWGVTDKDAR EYYAVTILVS    60
GIASAAYLSM FFGIGLTEVS VGGEMLDIYY ARYAQWLFTT PLLLLHLALL AKVDRVTIGT   120
LVGVDALMIV TGLIGALSHT AIARYSWWLF STICMIVLYV VLATSLRSAA KERGPEVAST   180
FNTLTALVLV LWTAYPILWI IGTEGAGVVG LGIETLLFMV LDTAVKVGFG FILLRSRAIL   240
GDTEAPEPSA GADVSAADMA EIGTGFPFDP HYVEVLGERM HYDVGPRDG TPVLFLHGNP   300
TSSYVWRNII PHVAPTHRCI APDLIGMGKS DKPDLGYFFD DHVRFMDAFI EALGLEEVVL   360
VIHDWGSALG FHWAKRNPER VKGIAFMEFI RPIPTWDEWP EFARETFQAF RTTDVGRKLI   420
IDQNVFIEGT LPMGVVRPLT EVEMDHYREP FLNPVDREPL WRFPNELPIA GEPANIVALV   480
EEYMDWLHQS PVPKLLFWGT PGVLIPPAEA ARLAKSLPNC KAVDIGPGLN LLQEDNPDLI   540
GSEIARWLST LEISGEPTTK SRITSEGEYI PLDQIDINVG GFCYENEV                588
```

```
SEQ ID NO: 23           moltype = DNA   length = 1365
FEATURE                 Location/Qualifiers
misc_feature            1..1365
                        note = Synthetic
source                  1..1365
                        mol_type = other DNA
                        organism = synthetic construct
```
SEQUENCE: 23

```
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg gaatattacg ctgtgactat cctggtgtcc   180
ggaatcgcat ccgccgcata tctgtctatg ttctttggta tcgggcttac tgaggtgtcc   240
gtcggggggcg aaatgttgga tatctattat gccaggtacg cccagtggct gtttaccacc   300
ccacttctgc tgctgcacct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gttctggcta catccctgcg atctgctgca aaggagcggg gccccgaggt ggcatctacc   540
tttaacaccc tgacagtctc ggtcttggtg ctgtggaccg cttaccctat cctgtggatc   600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcgacaccg aggacaaaga ctgcgaaatg aagcgcacca cctgatag   ccctctgggc   780
aagctggaac tgtctgggtg cgaacagggc ctgcaccgta tcatcttcct gggcaaagga   840
acatctgccg ccgacgccgt ggaagtgcct gccccagccg ccgtgctggg cggaccagag   900
ccactgatgc aggccaccgc ctggctcaac gcctactttc accagcctga ggccatcgag   960
gagttccctg tgccagccct gcaccaccca gtgttccagc aggagagctt tacccgccag  1020
gtgctgtgga aactgctgaa agtggtgaag ttcggagagg tcatcagcta cagccacctg  1080
gccgccctgg ccggcaatcc cgccgccacc gccgccgtga aaccgccct   gagcggaaat  1140
cccgtgccca ttctgatccc ctgccaccgg gtggtgcagg gcgacctgga cgtggggggc  1200
tacgagggcg ggctcgccgt gaaagagtgg ctgctggccc acgagggcca cagactgggc  1260
aagcctgggc tgggtaagag tagaatcaca agcgaaggcg agtacatccc cctggatcaa  1320
atagacataa atgtaggtgg attttgttat gagaatgaag tataa               1365

SEQ ID NO: 24          moltype = AA  length = 454
FEATURE                Location/Qualifiers
REGION                 1..454
                       note = Synthetic
source                 1..454
                       mol_type = protein
                       organism = synthetic construct
SEQUENCE: 24
MVSIALQAGY DLLGDGRPET LWLGIGTLLM LIGTFYFLVR GWGVTDKDAR EYYAVTILVS    60
GIASAAYLSM FFGIGLTEVS VGGEMLDIYY ARYAQWLFTT PLLLLHLALL AKVDRVTIGT   120
LVGVDALMIV TGLIGALSHT AIARYSWWLF STICMIVVLY VLATSLRSAA KERGPEVAST   180
FNTLTALVLV LWTAYPILWI IGTEGAGVVG LGIETLLFMV LDVTAKVGFG FILLRSRAIL   240
GDTEDKDCEM KRTTLDSPLG KLELSGCEQG LHRIIFLGKG TSAADAVEVP APAAVLGGPE   300
PLMQATAWLN AYFHQPEAIE EFPVPALHHP VFQQESFTRQ VLWKLLKVVK FGEVISYSHL   360
AALAGNPAAT AAVKTALSGN PVPILIPCHR VVQGDLDVGG YEGGLAVKEW LLAHEGHRLG   420
KPGLGKSRIT SEGEYIPLDQ IDINVGGFCY ENEV                              454

SEQ ID NO: 25          moltype = DNA  length = 1767
FEATURE                Location/Qualifiers
misc_feature           1..1767
                       note = Synthetic
source                 1..1767
                       mol_type = other DNA
                       organism = synthetic construct
SEQUENCE: 25
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg gaatattacg ctgtgactat cctggtgtcc   180
ggaatcgcat ccgccgcata tctgtctatg ttctttggta tcgggcttac tgaggtgtcc   240
gtcggggggcg aaatgttgga tatctattat gccaggtacg cccagtggct gtttaccacc   300
ccacttctgc tgctgcacct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gttctggcta catccctgcg atctgctgca aaggagcggg gccccgaggt ggcatctacc   540
tttaacaccc tgacagtctc ggtcttggtg ctgtggaccg cttaccctat cctgtggatc   600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcgacaccg aggcaccaga acccagtgcc ggtgccgatg tcagtgccgc cgacatggca   780
gaaatcggta ctggctttcc attcgacccc cattatgtgg aagtcctggg cgagcgcatg   840
cactacgtcg atgttggtcc gcgcgatggc accccgtccg tgttcctgca cggtaaccgg   900
acctcctcct acgtgtggcg caacatcatc ccgcatgttg caccgaccca tcgctgcatt   960
gctccagacc tgatcggtat gggcaaatcc gacaaaccag acctgggtta tttcttcgac  1020
gaccacgtcc gcttcatgga tgccttcatc gaagccctgg gtctggaaga ggtcgtcctg  1080
gtcattcacg actgggggctc cgctctgggt ttccactggg ccaagcgcaa tccagagcgc  1140
gtcaaaggta ttgcatttat ggagttcatc cgccctatcc cgacctggga cgaattgccc  1200
gaatttgccc gcgagacctt ccaggccttc cgcaccaccg acgtcggccg caagctgatc  1260
atcgatcaga acgtttttat cgagggtacg ctgccgatgg tgtcgtccg cccgctgact  1320
gaagtcgaga tggaccatta ccgcgagccg ttcctgaatc ctgttgaccg cgagccactg  1380
tggcgcttcc caaacgagct gccaatcgcc ggtgagccag cgaacatcgt cgcgctggtc  1440
gaagaataca tgactggct gcaccagtcc cctgtcccga agctgctgtt ctggggcgtc  1500
ccaggcgttc tgatcccacc ggccgaagcc gctcgcctgg ccaaaagcct gcctaactga  1560
aaggctgtgg acatcggccc gggtctgaat ctgctgcaag aagacaaccc ggaccctgatc  1620
ggcagcgaga tcgcgcgctg gctgtcgacg ctcgagattt ccggcgagcc aaccactaag  1680
agtagaatca caagcgaagg cgagtacatc cccctggatc aaatagacat aaatgtaggt  1740
ggattttgtt atgagaatga agtataa                                      1767
```

```
SEQ ID NO: 26             moltype = AA   length = 588
FEATURE                   Location/Qualifiers
REGION                    1..588
                          note = Synthetic
source                    1..588
                          mol_type = protein
                          organism = synthetic construct
SEQUENCE: 26
MVSIALQAGY DLLGDGRPET LWLGIGTLLM LIGTFYFLVR GWGVTDKDAR EYYAVTILVS   60
GIASAAYLSM FFGIGLTEVS VGGEMLDIYY ARYAQWLFTT PLLLLHLALL AKVDRVTIGT  120
LVGVDALMIV TGLIGALSHT AIARYSWWLF STICMIVVLY VLATSLRSAA KERGPEVAST  180
FNTLTALVLV LWTAYPILWI IGTEGAGVVG LGIETLLFMV LDVTAKVGFG FILLRSRAIL  240
GDTEAPEPSA GADVSAADMA EIGTGFPFDP HYVEVLGERM HYVDVGPRDG TPVLFLHGNP  300
TSSYVWRNII PHVAPTHRCI APDLIGMGKS DKPDLGYFFD DHVRFMDAFI EALGLEEVVL  360
VIHDWGSALG FHWAKRNPER VKGIAFMEFI RPIPTWDEWP EFARETFQAF RTTDVGRKLI  420
IDQNVFIEGT LPMGVVRPLT EVEMDHYREP FLNPVDREPL WRFPNELPIA GEPANIVALV  480
EEYMDWLHQS PVPKLLFWGT PGVLIPPAEA ARLAKSLPNC KAVDIGPGLN LLQEDNPDLI  540
GSEIARWLST LEISGEPTTK SRITSEGEYI PLDQIDINVG GFCYENEV              588

SEQ ID NO: 27             moltype = DNA   length = 1755
FEATURE                   Location/Qualifiers
misc_feature              1..1755
                          note = Sythentic
source                    1..1755
                          mol_type = other DNA
                          organism = synthetic construct
SEQUENCE: 27
atggtaagta tcgctctgca ggctggttac gacctactgg gtgacggcag acctgaaacc   60
ctgtggctgg gcatcggcac tctgctgatg ctgattggaa ccttctactt tctggtcgtc  120
ggatggggag tcaccgataa ggatgcccgg gaatattacg ctgtgactat cctggtgtcc  180
ggaatcgcat ccgccgcata tctgtctatg ttctttggta tcgggcttac tgaggtgtcc  240
gtcggggggcg aaatgttgga tatctattat gccaggtacg cccagtggct gtttaccacc  300
ccacttctgc tgctgcacct ggcccttctc gctaaggtgg atcgggtgac catcggcacg  360
ctggtgggtg tggacgccct gatgatcgtc actgggctca tcggagcctt gagccacacg  420
gccatagcca gatacagttg gtggttgttc tctacaattt gcatgatagt ggtgctctat  480
gttctggcta catccctgcg atctgctgca aggagcgggc cccgaggtgg catctacc   540
tttaacaccc tgacagctct ggtcttggtg ctgtggaccg cttacccat cctgtggatc  600
ataggcactg agggcgctgg cgtggtgggc ctgggaatcg aaactctgct gtttatgtg  660
ttggacgtga ctgccaaggt cggctttggc tttatcctgt tgagatcccg ggctattctg  720
ggcgacaccg aggcaccaga acccagtgcc ggtgccgatg tcatggcaga aatcggtact  780
ggcttccat tcgaccccca ttatgtggaa gtcctgggcg agcgcatgca ctacgtcgat  840
gttggtccgc gcgatggcac ccctgtgctg ttcctgcacg gtaaccgac ctcctcctac  900
gtgtggcgca acatcatccc gcatgttgca ccgacccatc gctgcattgc tccagacctg  960
atcggtatgg gcaaatccga caaaccgacg ctggttatt tcttcgacga ccacgtccgc 1020
ttcatggatg ccttcatcga agccctgggt ctggaagagg tcgtcctggt cattcacgac 1080
tgggggtccg ctctgggttt ccactgggcc aagcgcaatc cagagcgcgt caaaggtatt 1140
gcatttatgg agttcatccg ccctatcccg acctgggacg aatggccaga atttgcccgc 1200
gagaccttcc aggcctttcg caccaccgac gtcggccgca agctgatcat cgatcagaac 1260
gttttttatc agggtacgct gccgatgggt gtcgtccgcc cgctgactga agtcgagatg 1320
gaccattacc gcgagccgtt cctgaatcct gttgaccgcg agccactgtg gcgcttccca 1380
aacgagctgc caatcgccgg tgagccagcg aacatcgtcg cgctggtcga agaatacatg 1440
gactggctgc accagtcccc tgtcccgaag ctgctgtctct gggcaccccc aggcgttctg 1500
atcccaccgg ccgaagccgc tcgcctgccc aaaagcctgc ctaactgcaa ggctgtggac 1560
atcgggcccgg gtctgaatct gctgcaagaa gacaacccgg acctgatcgg cagcgagatc 1620
gcgcgctggc tgtcgacgct cgagatttcc ggcgagccaa ccactaagag tagaatcaca 1680
agcgaaggcg agtacatccc cctggatcaa atagacataa atgtaggtgg attttgttat 1740
gagaatgaag tataa                                                  1755

SEQ ID NO: 28             moltype = AA   length = 584
FEATURE                   Location/Qualifiers
REGION                    1..584
                          note = Synthetic
source                    1..584
                          mol_type = protein
                          organism = synthetic construct
SEQUENCE: 28
MVSIALQAGY DLLGDGRPET LWLGIGTLLM LIGTFYFLVR GWGVTDKDAR EYYAVTILVS   60
GIASAAYLSM FFGIGLTEVS VGGEMLDIYY ARYAQWLFTT PLLLLHLALL AKVDRVTIGT  120
LVGVDALMIV TGLIGALSHT AIARYSWWLF STICMIVVLY VLATSLRSAA KERGPEVAST  180
FNTLTALVLV LWTAYPILWI IGTEGAGVVG LGIETLLFMV LDVTAKVGFG FILLRSRAIL  240
GDTEAPEPSA GADVMAEIGT GFPFDPHYVE VLGERMHYVD VGPRDGTPVL FLHGNPTSSY  300
VWRNIIPHVA PTHRCIAPDL IGMGKSDKPD LGYFFDDHVR FMDAFIEALG LEEVVLVIHD  360
WGSALGFHWA KRNPERVKGI AFMEFIRPIP TWDEWPEFAR ETFQAFRTTD VGRKLIIDQN  420
VFIEGTLPMG VVRPLTEVEM DHYREPFLNP VDREPLWRFP NELPIAGEPA NIVALVEEYM  480
DWLHQSPVPK LLFWGTPGVL IPPAEAARLA KSLPNCKAVD IGPGLNLLQE DNPDLIGSEI  540
ARWLSTLEIS GEPTTKSRIT SEGEYIPLDQ IDINVGGFCY ENEV                  584

SEQ ID NO: 29             moltype = DNA   length = 1743
```

```
FEATURE                 Location/Qualifiers
misc_feature            1..1743
                        note = Sythentic
source                  1..1743
                        mol_type = other DNA
                        organism = synthetic construct
SEQUENCE: 29
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg aatattacg ctgtgactat cctggtgtcc    180
ggaatcgcat ccgccgcata tctgtctatg ttctttggta tcgggcttac tgaggtgtcc   240
gtcgggggcg aaatgttgga tatctattat gccaggtacg cccagtggct gtttaccacc   300
ccacttctgc tgctgcacct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gttctggcta catccctgcg atctgctgca aggagcggg ccccgaggt ggcatctacc     540
tttaacaccc tgacagctct ggtcttggtg ctgtggaccg cttacccat cctgtggatc    600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcgacaccg aggcaccaga acccagtgcc atggcagaaa tcggtactgg ctttccattc   780
gacccccatt atgtggaagt cctgggcgag cgcatgcact acgtcgatgt tggtccgcgc   840
gatggcaccc ctgtgctgtt cctgcacggt aacccgacct cctcctacgt gtggcgcaac   900
atcatcccgc atgttgcacc gacccatcgc tgcattgctc cagacctgat cggtatgggc   960
aaaatccgaca aaccagacct gggttatttc ttcgacgacc acgtccgctt catggatgcc  1020
ttcatcgaag ccctgggtct ggaagaggtc gtcctggtca ttcacgactg gggctccgct  1080
ctgggttttc actgggccaa cgcaatcca gagcgcgtca aaggtattgc atttatggag   1140
ttcatccgcc ctatcccgac ctgggacgaa tggccagaat tgcccgcgca gaccttccag  1200
gccttccgca ccaccgacgt cggccgcaag ctgatcatcg atcagaacgt ttttatcgag  1260
ggtacgctgc cgatgggtgt cgtccgcccg ctgactgaag tcgagatgga ccattaccgc  1320
gagccgttcc tgaatcctgt tgaccgcgag ccactgtggc gcttcccaaa cgagctgcca  1380
atcgccggtg agccagcgaa catcgtcgcg ctggtcgaag aatacatgga ctggctgcac  1440
cagtcccctg tcccgaagct gctgttctgg ggcaccccag cgttctgat cccaccggcc   1500
gaagccgctc gcctggccaa aagcctgcct aactgcaagg ctgtggacat cggcccgggt  1560
ctgaatctgc tgcaagaaga caacccggac ctgatcggca gcgagatcgc gcgctggctg  1620
tcgacgctcg agatttccgg cgagccaacc actaagagta gaatcacaag cgaaggcgag  1680
tacatccccc tggatcaaat agacataaat gtaggtggat tttgttatga gaatgaagta  1740
taa                                                                1743

SEQ ID NO: 30           moltype = AA   length = 580
FEATURE                 Location/Qualifiers
REGION                  1..580
                        note = Synthetic
source                  1..580
                        mol_type = protein
                        organism = synthetic construct
SEQUENCE: 30
MVSIALQAGY DLLGDGRPET LWLGIGTLLM LIGTFYFLVR GWGVTDKDAR EYYAVTILVS    60
GIASAAYLSM FFGIGLTEVS VGGEMLDIYY ARYAQWLFTT PLLLLHLALL AKVDRVTIGT   120
LVGVDALMIV TGLIGALSHT AIARYSWWLF STICMVVLY VLATSLRSAA KERGPEVAST    180
FNTLTALVLV LWTAYPILWI IGTEGAGVVG LGIETLLFMV LDVTAKVGFG FILLRSRAIL   240
GDTEAPEPSA MAEIGTGFPF DPHYVEVLGE RMHYVDVGPR DGTPVLFLHG NPTSSYVWRN   300
IIPHVAPTHR CIAPDLIGMG KSDKPDLGYF FDDHVRFMDA FIEALGLEEV VLVIHDWGSA   360
LGFHWAKRNP ERVKGIAFME FIRPIPTWDE WPEFARETFQ AFRTTDVGRK LIIDQNVFIE   420
GTLPMGVVRP LTEVEMDHYR EPFLNPVDRE PLWRFPNELP IAGEPANIVA LVEEYMDWLH   480
QSPVPKLLFW GTPGVLIPPA EAARLAKSLP NCKAVDIGPG LNLLQEDNPD LIGSEIARWL   540
STLEISGEPT TKSRITSEGE YIPLDQIDIN VGGFCYENEV                         580

SEQ ID NO: 31           moltype = DNA   length = 1731
FEATURE                 Location/Qualifiers
misc_feature            1..1731
                        note = Synthetic
source                  1..1731
                        mol_type = other DNA
                        organism = synthetic construct
SEQUENCE: 31
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg aatattacg ctgtgactat cctggtgtcc    180
ggaatcgcat ccgccgcata tctgtctatg ttctttggta tcgggcttac tgaggtgtcc   240
gtcgggggcg aaatgttgga tatctattat gccaggtacg cccagtggct gtttaccacc   300
ccacttctgc tgctgcacct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gttctggcta catccctgcg atctgctgca aggagcgggg ccccgaggt ggcatctacc    540
tttaacaccc tgacagctct ggtcttggtg ctgtggaccg cttacccat cctgtggatc    600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcgacaccg aggcaccaat ggcagaaatc ggtactggct tccattcga ccccattat    780
gtggaagtcc tgggcgagcg catgcactac gtcgatgttg gtccgcgcga tggcacccct   840
```

```
gtgctgttcc tgcacggtaa cccgacctcc tcctacgtgt ggcgcaacat catcccgcat  900
gttgcaccga cccatcgctg cattgctcca gacctgatcg gtatgggcaa atccgacaaa  960
ccagacctgg gttatttctt cgacgaccac gtccgcttca tggatgcctt catcgaagcc 1020
ctgggtctga agaggtcgt cctggtcatt cacgactggg gctccgctct gggtttccac 1080
tgggccaagc gcaatccaga gcgcgtcaaa ggtattgcat ttatggagtt catccgccct 1140
atcccgacct gggacgaatg gccagaattt gcccgcgaga ccttccaggc cttccgcacc 1200
accgacgtcg gccgcaagct gatcatcgat cagaacgttt ttatcgaggg tacgctgccg 1260
atgggtgtct ccgcccgct gactgaagtc gagatggacc attaccgcga gccgttcctg 1320
aatcctgttg accgcgagcc actgtggcgc ttcccaaacg agctgccaat cgccggtgag 1380
ccagcgaaca tcgtcgcgct ggtcgaagaa tacatggact ggctgcacca gtcccctgtc 1440
ccgaagctgc tgttctgggg caccccaggc gttctgatcc caccggccga agccgctcgc 1500
ctggccaaaa gcctgcctaa ctgcaaggct gtggacatcg gcccgggtct gaatctgctg 1560
caagaagaca acccggacct gatcggcagc gagatcgcgc gctggctgtc gacgctcgag 1620
atttccggcg agccaaccac taagtagtaga atcacaagcg aaggcgagta catccccctg 1680
gatcaaatag acataaatgt aggtggattt tgttatgaga atgaagtata a            1731

SEQ ID NO: 32       moltype = AA  length = 576
FEATURE             Location/Qualifiers
REGION              1..576
                    note = Synthetic
source              1..576
                    mol_type = protein
                    organism = synthetic construct
SEQUENCE: 32
MVSIALQAGY DLLGDGRPET LWLGIGTLLM LIGTFYFLVR GWGVTDKDAR EYYAVTILVS  60
GIASAAYLSM FFGIGLTEVS VGGEMLDIYY ARYAQWLFTT PLLLLHLALL AKVDRVTIGT 120
LVGVDALMIV TGLIGALSHT AIARYSWWLF STICMIVVLY VLATSLRSAA KERGPEVAST 180
FNTLTALVLV LWTAYPILWI IGTEGAGVVG LGIETLLFMV LDVTAKVGFG FILLRSRAIL 240
GDTEAPMAEI GTGFPFDPHY VEVLGERMHY VDVGPRDGTP VLFLHGNPTS SYVWRNIIPH 300
VAPTHRCIAP DLIGMGKSDK PDLGYFFDDH VRFMDAFIEA LGLEEVVLVI HDWGSALGFH 360
WAKRNPERVK GIAFMEFIRP IPTWDEWPEF ARETFQAFRT TDVGRKLIID QNVFIEGTLP 420
MGVVRPLTEV EMDHYREPFL NPVDREPLWR FPNELPIAGE PANIVALVEE YMDWLHQSPV 480
PKLLFWGTPG VLIPPAEAAR LAKSLPNCKA VDIGPGLNLL QEDNPDLIGS EIARWLSTLE 540
ISGEPTTKSR ITSEGEYIPL DQIDINVGGF CYENEV                            576

SEQ ID NO: 33       moltype = DNA  length = 1719
FEATURE             Location/Qualifiers
misc_feature        1..1719
                    note = Synthetic
source              1..1719
                    mol_type = other DNA
                    organism = synthetic construct
SEQUENCE: 33
atggtaagta tcgctctgca ggctggttac gacctactgg gtgacggcag acctgaaacc  60
ctgtggctgg gcatcggcac tctgctgatg ctgattggaa cctttactt tctggtccgc 120
ggatggggag tcaccgataa ggatgcccgg gaatattacg ctgtgactat cctggtgtcc 180
ggaatcgcat ccgccgcata tctgtctatg ttctttgtta tcgggcttac tgaggtgtcc 240
gtcggggcg aaatgttgga tatctattat gccaggtacg cccagtggct gtttaccacc 300
ccacttctgc tgctgcacct ggcccttctc gctaaggtgg atcgggtgac catcggcacc 360
ctggtgggtg tggacgccct gatgatcgtc actggcctca tcggagcctt gagccacacg 420
gccatagcca gatacagttg gtggttgttc tctacaattt gcatgatagt ggtgctctat 480
gttctggcta catccctgcg atctgctgca aaggagcggg ccccgaggt ggcatctacc 540
tttaacaccc tgacagctct ggtcttggtg ctgtggaccg cttacccat cctgtggatc 600
ataggcactg agggcgctgg cgtggtgggc ctgggcatcg aaactctgct gtttatggtg 660
ttggacgtga ctgccaaggt cggctttggc tttatcctgt tgagatcccg ggctattctg 720
ggcgacaccg aggaaatcgg tactggcttt ccattcgacc ccattatgt ggaagtcctg 780
ggcgagcgca tgcactacgt cgatgttggt ccgcgcgatg gcacccctgt gctgttcctg 840
cacggtaacc cgacctcctc ctacgtgtgg cgcaacatca tcccgcatgt tgcaccgacc 900
catcgctgca ttgctccaga cctgatcggt atgggcaaat gacaaaacc gacctgggt 960
tatttcttcg acgaccacgt ccgcttcatg gatgccttca tcgaagcct gggtctggaa 1020
gaggtcgtcc tggtcattca cgactggggc tccgctctgg gtttccactg gccaagcgc 1080
aatccagagc gcgtcaaagg tattgcattt atggagttca tccgccctat cccgacctgg 1140
gacgaatggc cagaatttgc ccgcgagacc ttccaggcct tccgcaccac cgacgtcggc 1200
cgcaagctga tcatcgatca gaacgttttt atcgagggta cgctgccgat gggtgtctc 1260
cgcccgctga ctgaagtcga gatggaccat taccgcgagc cgttcctgaa tcctgttgac 1320
cgcgagccac tgtggcgctt cccaaacgag ctgccaatcg ccggtgagcc agcgaacatc 1380
gtcgcgctg tcgaagaata catggactgg ctgcaccagt cccctgtccc gaagctgctg 1440
ttctggggca ccccaggcgt tctgatccca ccggccgaag ccgctcgcct ggccaaaagc 1500
ctgcctaact gcaaggctgt ggacatcggc ccgggtctga atctgctgca agaagacaac 1560
ccggacctga tcggcagcga gatcgcgcgc tggctgtcga cgctcgagat ttccggcgag 1620
ccaaccacta gagtagaat cacaagcgaa ggcgagtaca tccccctgga tcaaatagac 1680
ataaatgtag gtggattttg ttatgagaat gaagtataa                        1719

SEQ ID NO: 34       moltype = AA  length = 572
FEATURE             Location/Qualifiers
REGION              1..572
                    note = Synthetic
source              1..572
                    mol_type = protein
```

```
                        organism = synthetic construct
SEQUENCE: 34
MVSIALQAGY DLLGDGRPET LWLGIGTLLM LIGTFYFLVR GWGVTDKDAR EYYAVTILVS    60
GIASAAYLSM FFGIGLTEVS VGGEMLDIYY ARYAQWLFTT PLLLLHLALL AKVDRVTIGT   120
LVGVDALMIV TGLIGALSHT AIARYSWWLF STICMIVVLY VLATSLRSAA KERGPEVAST   180
FNTLTALVLV LWTAYPILWI IGTEGAGVVG LGIETLLFMV LDVTAKVGFG FILLRSRAIL   240
GDTEEIGTGF PFDPHYVEVL GERMHYVDVG PRDGTPVLFL HGNPTSSYVW RNIIPHVAPT   300
HRCIAPDLIG MGKSDKPDLG YFFDDHVRFM DAFIEALGLE EVVLVIHDWG SALGFHWAKR   360
NPERVKGIAF MEFIRPIPTW DEWPEFARET FQAFRTTDVG RKLIIDQNVF IEGTLPMGVV   420
RPLTEVEMDH YREPFLNPVD REPLWRFPNE LPIAGEPANI VALVEEYMDW LHQSPVPKLL   480
FWGTPGVLIP PAEAARLAKS LPNCKAVDIG PGLNLLQEDN PDLIGSEIAR WLSTLEISGE   540
PTTKSRITSE GEYIPLDQID INVGGFCYEN EV                                572

SEQ ID NO: 35           moltype = DNA  length = 1713
FEATURE                 Location/Qualifiers
misc_feature            1..1713
                        note = Synthetic
source                  1..1713
                        mol_type = other DNA
                        organism = synthetic construct
SEQUENCE: 35
atggtaagta tcgctctgca ggctggttac gacctactgg gtgacggcag acctgaaacc    60
ctgtggctgg gcatcggcac tctgctgatg ctgattggaa ccttctactt tctggtccgc   120
ggatggggag tcaccgataa ggatgcccgg gaatattacg ctgtgactat cctggtgtcc   180
ggaatcgcat ccgccgcata tctgtctatg ttctttggta tcgggcttac tgaggtgtcc   240
gtcggggcg aaatgttgga tatctattat gccaggtacg cccagtggct gttttaccacc   300
ccacttctgc tgctgcacct ggcccttctc gctaaggtgg atcgggtgac catcggcacc   360
ctggtgggtg tggacgccct gatgatcgtc actggcctca tcggagcctt gagccacacg   420
gccatagcca gatacagttg gtggttgttc tctacaattt gcatgatagt ggtgctctat   480
gttctggcta catccctgcg atctgctgca aaggagcggg ccccgaggt ggcatctacc   540
tttaacaccc tgacagctct ggtcttggtg ctgtgggaccg cttaccctat cctgtgggatc   600
ataggcactg agggcgctgg cgtggtgggc ctgggcatcg aaactctgct gtttatggtg   660
ttggacgtga ctgccaaggt cggctttggc tttatcctgt tgagatcccg ggctattctg   720
ggcacacca tcggtactgg cttttccattc gaccccatt atgtggaagt cctgggcgag   780
cgcatgcact acgtcgatgt tggtccgcgc gatggcaccc ctgtgctgtt cctgcacgtt   840
aacccgacct cctcctacgt gtggcgcaac atcatcccgc atgttgcacc gacccatcgc   900
tgcattgctc cagacctgat cggtatgggc aaatccgaca accagacct gggttatttc   960
ttcgacgacc acgtccgctt catggatgcc ttcatcgaag ccctgggtct ggaagaggtc  1020
gtcctggtca ttcacgactg gggctccgct ctgggtttcc actgggccaa gcgcaatcca  1080
gagcgcgtca aaggtattgc atttatggag ttcatccgcc ctatcccgac ctgggacgaa  1140
tggccagaat ttgcccgcga gaccttccag gccttccgca ccaccgacgt cggccgcaag  1200
ctgatcatcg atcagaacgt ttttatcgag ggtacgctgc cgatgggtgt cgtccgcccg  1260
ctgactgaag tcgagatgga ccattaccgc gagccgttcc tgaatcctga tgaccgcgag  1320
ccactgtggc gcttcccaaa cgagctgcca atcgccggtg agccagcgaa catcgtcgcg  1380
ctggtcgaag aatacatgga ctggctcac cagtcccctg tcccgaagct gctgttctgg  1440
ggcaccccag gcgttctgat cccaccggcc gaagccgctc gcctggccaa aagcctgcct  1500
aactgcaagg tcgtggacat cggcccgggt ctgaatctgc tgcaagaaga caacccggac  1560
ctgatcggca gcgagatcgc gcgctggctg tcgacgctcg agatttccgg cgagccaacc  1620
actaagagta gaatcacaag cgaaggcgag tacatccccc tggatcaaat agacataaat  1680
gtaggtggat tttgttatga gaatgaagta taa                                1713

SEQ ID NO: 36           moltype = AA  length = 570
FEATURE                 Location/Qualifiers
REGION                  1..570
                        note = Synthetic
source                  1..570
                        mol_type = protein
                        organism = synthetic construct
SEQUENCE: 36
MVSIALQAGY DLLGDGRPET LWLGIGTLLM LIGTFYFLVR GWGVTDKDAR EYYAVTILVS    60
GIASAAYLSM FFGIGLTEVS VGGEMLDIYY ARYAQWLFTT PLLLLHLALL AKVDRVTIGT   120
LVGVDALMIV TGLIGALSHT AIARYSWWLF STICMIVVLY VLATSLRSAA KERGPEVAST   180
FNTLTALVLV LWTAYPILWI IGTEGAGVVG LGIETLLFMV LDVTAKVGFG FILLRSRAIL   240
GDTIGTGFPF DPHYVEVLGE RMHYVDVGPR DGTPVLFLHG NPTSSYVWRN IIPHVAPTHR   300
CIAPDLIGMG KSDKPDLGYF FDDHVRFMDA FIEALGLEEV VLVIHDWGSA LGFHWAKRNP   360
ERVKGIAFME FIRPIPTWDE WPEFARETFQ AFRTTDVGRK LIIDQNVFIE GTLPMGVVRP   420
LTEVEMDHYR EPFLNPVDRE PLWRFPNELP IAGEPANIVA LVEEYMDWLH QSPVPKLLFW   480
GTPGVLIPPA EAARLAKSLP NCKAVDIGPG LNLLQEDNPD LIGSEIARWL STLEISGEPT   540
TKSRITSEGE YIPLDQIDIN VGGFCYENEV                                    570

SEQ ID NO: 37           moltype = DNA  length = 1707
FEATURE                 Location/Qualifiers
misc_feature            1..1707
                        note = Synthetic
source                  1..1707
                        mol_type = other DNA
                        organism = synthetic construct
SEQUENCE: 37
atggtaagta tcgctctgca ggctggttac gacctactgg gtgacggcag acctgaaacc    60
```

```
ctgtggctgg gcatcggcac tctgctgatg ctgattggaa ccttctactt tctggtccgc    120
ggatggggag tcaccgataa ggatgcccgg gaatattacg ctgtgactat cctggtgtcc    180
ggaatcgcat ccgccgcata tctgtctatg ttctttggta tcgggcttac tgaggtgtcc    240
gtcggggcg  aaatgttgga tatctattat gccaggtacg cccagtggct gtttaccacc    300
ccacttctgc tgctgcacct ggcccttctc gctaaggtgg atcgggtgac catcggcacc    360
ctggtgggtg tggacgccct gatgatcgtc actggcctca tcggagcctt gagccacacg    420
gccatagcca gatacagttg gtggttgttc tctacaattt gcatgatagt ggtgctctat    480
gttctggcta catccctgcg atctgctgca aaggagcggg cccccgaggt ggcatctacc    540
tttaacaccc tgacagctct ggtcttgtgt ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacacca ctggctttcc attcgacccc cattatgtgg aagtcctggg cgagcgcatg    780
cactacgtcg atgttggtcc gcgcgatggc acccctgtgc tgttcctgca cggtaacccg    840
acctcctcct acgtgtggcg caacatcatc cgcatgttgc accgaccca tcgctgcatt    900
gctccagacc tgatcggtat gggcaaatcc gacaaaccag acctgggtta tttcttcgac    960
gaccacgtcc gcttcatgga tgccttcatc gaagccctgg tctgaaga ggtcgtcctg    1020
gtcattcacg actgggctc cgctctgggt ttccactggg ccaagcgcaa tccagagcgc    1080
gtcaaaggta ttgcatttat ggagttcatc cgccctatc cgaccctggga gaatggcca    1140
gaatttgccc gcgagacctt ccaggccttc cgcaccaccg acgtcggccg caagctgatc    1200
atcgatcaga acgttttttat cgagggtacg ctgccgatgg tgtcgtccg cccgctgact    1260
gaagtcgaga tggaccatta ccgcgagccg ttcctgaatc ctgttgaccg cgagccactg    1320
tggcgcttcc caaacgagct gccaatcgcc ggtgagccag cgaacatcgc cgctgttc    1380
gaagaataca tggactggct gcaccagtcc cctgtcccga agctgctgtt ctgggggcacc    1440
ccaggcgttc tgatcccacc ggccgaagcc gctcgcctgg ccaaaagcct gcctaactgc    1500
aaggctgtgg acatcggccc gggtctgaat ctgctgcaag aagacaaccc ggacctgatc    1560
ggcagcgaga tcgcgcgctg gctgtcgacg ctcgagattt ccggcgagcc aaccactaag    1620
agtagaatca caagcgaagg cgagtacatc cccctggatc aaatagacat aaatgtaggt    1680
ggatttttgtt atgagaatga agtataa                                       1707

SEQ ID NO: 38          moltype = AA   length = 568
FEATURE                Location/Qualifiers
REGION                 1..568
                       note = Synthetic
source                 1..568
                       mol_type = protein
                       organism = synthetic construct
SEQUENCE: 38
MVSIALQAGY DLLGDGRPET LWLGIGTLLM LIGTFYFLVR GWGVTDKDAR EYYAVTILVS     60
GIASAAYLSM FFGIGLTEVS VGGEMLDIYY ARYAQWLFTT PLLLLHLALL AKVDRVTIGT    120
LVGVDALMIV TGLIGALSHT AIARYSWWLF STICMIVVLY VLATSLRSAA KERGPEVAST    180
FNTLTALVLV LWTAYPILWI IGTEGAGVVG LGIETLLFMV LDVTAKVGFG FILLRSRAIL    240
GDTTGFPFDP HYVEVLGERM HYVDVGPRDG TPVLFLHGNP TSSYVWRNII PHVAPTHRCI    300
APDLIGMGKS DKPDLGYFFD DHVRFMDAFI EALGLEEVVL VIHDWGSALG FHWAKRNPER    360
VKGIAFMEFI RPIPTWDEWP EFARETFQAF RTTDVGRKLI IDQNVFIEGT LPMGVVRPLT    420
EVEMDHYREP FLNPVDREPL WRFPNELPIA GEPANIVALV EEYMDWLHQS PVPKLLFWGT    480
PGVLIPPAEA ARLAKSLPNC KAVDIGPGLN LLQEDNPDLI GSEIARWLST LEISGEPTTK    540
SRITSEGEYI PLDQIDINVG GFCYENEV                                      568

SEQ ID NO: 39          moltype = DNA   length = 1701
FEATURE                Location/Qualifiers
misc_feature           1..1701
                       note = Synthetic
source                 1..1701
                       mol_type = other DNA
                       organism = synthetic construct
SEQUENCE: 39
atggtaagta tcgctctgca ggctggttac gacctactgg gtgacggcag acctgaaacc     60
ctgtggctgg gcatcggcac tctgctgatg ctgattggaa ccttctactt tctggtccgc    120
ggatggggag tcaccgataa ggatgcccgg gaatattacg ctgtgactat cctggtgtcc    180
ggaatcgcat ccgccgcata tctgtctatg ttctttggta tcgggcttac tgaggtgtcc    240
gtcggggcg  aaatgttgga tatctattat gccaggtacg cccagtggct gtttaccacc    300
ccacttctgc tgctgcacct ggcccttctc gctaaggtgg atcgggtgac catcggcacc    360
ctggtgggtg tggacgccct gatgatcgtc actggcctca tcggagcctt gagccacacg    420
gccatagcca gatacagttg gtggttgttc tctacaattt gcatgatagt ggtgctctat    480
gttctggcta catccctgcg atctgctgca aaggagcggg cccccgaggt ggcatctacc    540
tttaacaccc tgacagctct ggtcttgtgt ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacacct ttggctttcc attcgac ccccattat gtggaagtcc tgggcgagcg catgcactac    780
gtcgatgttg tccgcgcgcga tggcacccct gtgctgttcc tgcacggtaa cccgacctcc    840
tcctacgtgt ggcgcaacat catccgcat gttgcaccga cccatcgctg cattgctcca    900
gacctgatcg gtatgggcaa atccgacaaa ccagacctgg ttatttcttc gacgaccac    960
gtccgcttca tggatgcctt catcgaagcc ctgggtctga agaggtcgt cctggtcatt   1020
cacgactggg gctccgctct gggtttccac tgggccaagc gcaatccaga gcgctac    1080
ggtattgcat ttatggagtt catccgccct atcccgacct gggacgaatg gccagaattt    1140
gcccgcgaga ccttccaggc cttccgcacc accgacgtcg gccgcaagct gatcatcgat    1200
cagaacgttt ttatcgaggg tacgctgccg atgggtgtcg tccgcccgct gactgaagtc    1260
gagatggacc attaccgcga gccgttcctg aatcctgttg accgcgagcc actgtggcgc    1320
ttcccaaaac gagctgccaat cgccggtgag ccagcgaaca tcgtcgcgct ggtcgaagaa    1380
```

```
tacatggact ggctgcacca gtcccctgtc ccgaagctgc tgttctgggg cacccaggc   1440
gttctgatcc caccggccga agccgctcgc ctggccaaaa gcctgcctaa ctgcaaggct  1500
gtggacatcg gcccgggtct gaatctgctg caagaagaca acccggacct gatcggcagc  1560
gagatcgcgc gctggctgtc gacgctcgag atttccggcg agccaaccac taagagtaga  1620
atcacaagcg aaggcgagta catcccctg gatcaaatag acataaatgt aggtggattt   1680
tgttatgaga atgaagtata a                                            1701

SEQ ID NO: 40           moltype = AA  length = 566
FEATURE                 Location/Qualifiers
REGION                  1..566
                        note = Synthetic
source                  1..566
                        mol_type = protein
                        organism = synthetic construct
SEQUENCE: 40
MVSIALQAGY DLLGDGRPET LWLGIGTLLM LIGTFYFLVR GWGVTDKDAR EYYAVTILVS   60
GIASAAYLSM FFGIGLTEVS VGGEMLDIYY ARYAQWLFTT PLLLLHLALL AKVDRVTIGT  120
LVGVDALMIV TGLIGALSHT AIARYSWWLF STICMIVVLY VLATSLRSAA KERGPEVAST  180
FNTLTALVLV LWTAYPILWI IGTEGAGVVG LGIETLLFMV LDVTAKVGFG FILLRSRAIL  240
GDTFPFDPHY VEVLGERMHY VDVGPRDGTP VLFLHGNPTS SYVWRNIIPH VAPTHRCIAP  300
DLIGMGKSDK PDLGYFFDDH VRFMDAFIEA LGLEEVVLVI HDWGSALGFH WAKRNPERVK  360
GIAFMEFIRP IPTWDEWPEF ARETFQAFRT TDVGRKLIID QNVFIEGTLP MGVVRPLTEV  420
EMDHYREPFL NPVDREPLWR FPNELPIAGE PANIVALVEE YMDWLHQSPV PKLLFWGTPG  480
VLIPPAEAAR LAKSLPNCKA VDIGPGLNLL QEDNPDLIGS EIARWLSTLE ISGEPTTKSR  540
ITSEGEYIPL DQIDINVGGF CYENEV                                      566
```